US010588320B2

(12) United States Patent
Bywater-Ekegard et al.

(10) Patent No.: US 10,588,320 B2
(45) Date of Patent: Mar. 17, 2020

(54) CELL FREE SUPERNATANT COMPOSITION OF MICROBIAL CULTURE FOR AGRICULTURAL USE

(71) Applicant: CONCENTRIC AG CORPORATION, Centennial, CO (US)

(72) Inventors: Margaret Bywater-Ekegard, Lac Brome (CA); Ananda Fitzsimmons, Frelighsburg (CA)

(73) Assignee: CONCENTRIC AG CORPORATION, Centennial, CO (US)

( * ) Notice: Subject to any disclaimer, the term of this patent is extended or adjusted under 35 U.S.C. 154(b) by 0 days.

(21) Appl. No.: 14/849,485

(22) Filed: Sep. 9, 2015

(65) Prior Publication Data
US 2016/0100587 A1   Apr. 14, 2016

Related U.S. Application Data

(60) Provisional application No. 62/048,256, filed on Sep. 9, 2014.

(51) Int. Cl.
| A01N 63/02 | (2006.01) |
| A01N 63/04 | (2006.01) |
| C05B 17/00 | (2006.01) |
| C05D 1/00 | (2006.01) |
| C05D 3/00 | (2006.01) |
| C05D 5/00 | (2006.01) |
| C05D 9/02 | (2006.01) |
| C05F 11/00 | (2006.01) |
| C05F 11/08 | (2006.01) |
| C05F 11/10 | (2006.01) |
| C05G 3/02 | (2006.01) |

(52) U.S. Cl.
CPC .............. *A01N 63/02* (2013.01); *A01N 63/04* (2013.01); *C05B 17/00* (2013.01); *C05D 1/00* (2013.01); *C05D 3/00* (2013.01); *C05D 5/00* (2013.01); *C05D 9/02* (2013.01); *C05F 11/00* (2013.01); *C05F 11/08* (2013.01); *C05F 11/10* (2013.01); *C05G 3/02* (2013.01)

(58) Field of Classification Search
CPC .......... A01N 63/02; A01N 63/04; C05D 5/00; C05D 1/00; C05B 17/00; C05F 11/00; C05F 11/08
See application file for complete search history.

(56) References Cited

U.S. PATENT DOCUMENTS

| 5,578,486 A | 11/1996 | Zhang |
| 5,667,779 A | 9/1997 | Kubo |
| 5,716,523 A | 2/1998 | Powlen |
| 6,025,187 A | 2/2000 | Penaud |
| 6,326,016 B2 | 12/2001 | Moesinger |
| 6,905,288 B2 | 6/2005 | Miyazaki |
| 7,811,353 B2 | 10/2010 | Blais |
| 9,175,258 B2 | 11/2015 | Bywater-Ekegard et al. |
| 2001/0014324 A1 | 8/2001 | Moesinger |
| 2008/0032382 A1 | 2/2008 | Schnoor et al. |
| 2009/0011491 A1 | 1/2009 | Barnabe et al. |
| 2010/0209988 A1 | 8/2010 | Hutchings et al. |
| 2012/0015806 A1 | 1/2012 | Paikray et al. |
| 2012/0031157 A1 | 2/2012 | Paikray |
| 2013/0205849 A1* | 8/2013 | Kloepper ............ A01G 9/1086 71/6 |
| 2014/0120601 A1 | 5/2014 | Bywater-Ekegard et al. |
| 2016/0100587 A1 | 4/2016 | Bywater-Ekegard et al. |

FOREIGN PATENT DOCUMENTS

| CN | 1721345 A | 1/2006 |
| CN | 101186879 A | 5/2008 |
| CN | 101591679 A | 12/2009 |
| CN | 101698539 A | 4/2010 |
| EP | 1 150 577 B1 | 10/2006 |
| JP | S5319673 A | 2/1978 |
| KR | 20040006045 A | 1/2004 |
| RU | 2322061 C2 | 4/2008 |
| WO | WO 2007/150052 A1 | 12/2007 |
| WO | WO 2011157747 A2 | 12/2011 |
| WO | WO 2012/101528 * | 8/2012 |
| WO | WO2016/038460 A2 | 3/2016 |

OTHER PUBLICATIONS

Adam et al., (2014) PLoS ONE 9(2): e90402. Published Feb. 28, 2014.*
Garbaye et al., New Phytol. ( 1994), 128, 197-210.*
Harwood CS, et al. (1986) Uptake of Benzoate by Rhodopseudomonas palustris Grown Anaerobically in Light. J. Bacteriology, 165(2): 504-509.
First Examination Report issued by the Australian Patent Office dated Mar. 18, 2015 for Australian Application No. 2012210260 filed on Jan. 12, 2012 (Inventor—Bywater Ekegärd; Applicant—Inocucor).
First Office Action issued by the State Intellectual Property Office of the People's Republic of China dated Sep. 3, 2014 for Chinese Application No. 201280009159.9 filed on Jan. 12, 2012, which was published as 103649303A dated Mar. 9, 2014 (Inventor—Bywater Ekegärd; Applicant—Inocucor).
Ying, Liu, et al., Review on Degradation and Conversion of Environmental Pollutants by Mycorrhizal Fungi. Shanghai Environmental Sciences, vol. 17, No. 2, pp. 127-131.
Second Office Action issued by the State Intellectual Property Office of the People's Republic of China dated Jul. 14, 2015 for Chinese Application No. 201280009159.9, filed on Jan. 12, 2012, and published as 103649303A dated Mar. 9, 2014 (Inventor—Bywater Ekegärd; Applicant—Inocucor Tech., Inc.) (Translation—7 pages).

(Continued)

*Primary Examiner* — Kade Ariani
(74) *Attorney, Agent, or Firm* — Goodwin Procter LLP

(57) ABSTRACT

The present disclosure comprises compositions and methods for biostimulation, such as seed germination and plant growth. For example, the present disclosure comprises compositions and methods for affecting, enhancing, modulating, stimulating, or aiding plant growth. This abstract is intended as a scanning tool for purposes of searching in the particular art and is not intended to be limiting of the present disclosure.

12 Claims, 35 Drawing Sheets

Specification includes a Sequence Listing.

(56) References Cited

OTHER PUBLICATIONS

Bankar AV, et al. (2009) Environmental and industrial applications of Yarrowia lipolytica. Applied Microbiology and Biotechnology, 84(5): 847:865.
Bankar AV, et al. (2009) Removal of chromium (VI) ions from aqueous solution by absorption into two marine isolates of Yarrowia lipolytica. Journal of Harzardous Materials, 170(1): 487-494.
Fickers P., et al. (2005) Hydrophobic substrate utilisation by the yeast Yarrowia lipoytica, and its potential applications. FEMS Yeast Research, 5(6-7): 527-543.
Harwood CS, et al. (1999) Anaerobic metabolism of aromatic compounds via the benzoyl-CoA pathway. FEMS microbiology Reviews, 22: 439-458.
Harwood CS, et al. (1986) Uptake of benzoate by Rhodopseudomonas palustris grown anaerobically in light. J. Bacterial, 165(2): 504-509.
Nam, et al. (2003) A novel catabolic activity of Pseudomonas veronii in biotransformation of pentachlorophenol. Applied microbiology and Biotechnology, 62(2-3): 284-290.
Onaca, et al. (2007) Degradation of alkyl; methyl ketones by Pseudomonas vernil. Journal of Bacteriology, 189(10): 3759-3767.
Jain MR, et al. (2004) 2,4,6-trinitrotoluene transformation by a tropical marine yeast, Yarrowia liplytica NCIM 3589. Marine Pollution Bulletin, 49(9-10): 783-788.
Rokas A. (2009) The effect of domestication on the fungal proteome. Trends in Genetics: TIG, 25(2): 60-63.
Schennen U, et al. (1985) Anaerobic degradation of 2 fluorobenzoate by benzoate-degrading, denitrifying bateria. J. Bacteriol., 161(1): 321-325.
Taher DM, et al. (2009) Comparison of normal composting with composting using effective microorganisms for poultry carcasses disposal in disposal in poultry farms. Iraqi Journal of Veterinary Sciences, 23(2): 1607-3994.
International Preliminary Report on Patentability issued by the International Searching Authority dated Jul. 27, 2013 for PCT/IB2012/000833 filed Jan. 12, 2012 and published as WO 2012/101528 dated Aug. 2, 2012 (Applicants—Inocucor; Inventors—Bywater-Ekegard, et al.) (9 pages).
International Search Report issued by the International Searching Authority dated Aug. 10, 2012 for PCT/IB2012/000833 filed Jan. 12, 2012 and published as WO 2012/101528 dated Aug. 2, 2012 (Applicants—Inocucor; Inventors—Bywater-Ekegard, et al.) (3 pages).
Written Opinion issued by the International Searching Authority dated Aug. 10, 2012 for PCT/IB2012/000833 filed Jan. 12, 2012 and published as WO 2012/101528 dated Aug. 2, 2012 (Applicants—Inocucor; Inventors—Bywater-Ekegard, et al.) (8 pages).
Non-Final Office Action dated Mar. 12, 2015 for U.S. Appl. No. 13/979,419, filed Jan. 6, 2014 (Margaret Bywater-Ekegard—inventors) (18 pages).
Non-Final Office Action dated Nov. 14, 2014 for U.S. Appl. No. 13/979,419, filed Jan. 6, 2014 (Margaret Bywater-Ekegard—inventors) (11 pages).
Abbasi, P., et al., "Detection of High Concentrations of Organic Acids in Fish Emulsion and Their Role in Pathogen or Disease Suppression," Phytopathology, 2009, pp. 274-281, vol. 99, No. 3.
Conn, K., et al., "Liquid Swine Manure Can Kill Verticillium dahliae Microsclerotia in Soil by Volatile Fatty Acid, Nitrous Acid, and Ammonia Toxicity," Phytopathology, 2005, pp. 28-35, vol. 95, No. 1.
Cook, K.L., "Optimizing Culturing Conditions for Bacillus Subtilis," South African Avocado Growers' Association Yearbook 1996, vol. 19, pp. 54-58.
McKellar, M., et al., "Compost-Induced Suppression of Pythium Damping-Off Is Mediated by Fatty-Acid-Metabolizing Seed-Colonizing Microbial Communities," Applied and Environmental Microbiology, Jan. 2003, pp. 452-460, vol. 69, No. 1.
Tenuta, M., et al., "Volatile Fatty Acids in Liquid Swine Manure Can Kill Microsclerotia of Verticillium dahliae," Phytopathology, 2002, pp. 548-552, vol. 92, No. 5.
Widmer, T.L., et al., "Composted Municipal Waste Reduces Infection of Citrus Seedlings by Phytophthora nicotianae," Plant Disease, Jun. 1998, pp. 683-683, vol. 82, No. 6.
Adam, M. Et al., "Bacterial Antagonists of Fungal Pathogens Also Control Root-Knot Nematodes by Induced Systemic Resistance of Tomato Plants," PLOS ONE, Feb. 28, 2014, vol. 9, No. 2, eight pages.
ATCC, "Availability of Deposits," 2016, two pages. [Online] [Retrieved from the internet] Retrieved on Apr. 24, 2018, URL: <https://www.Igcstandards-atcc.org/en/Services/Deposits_Services/Patent_Depository/Additional_Information/Availibility_of_Deposits.aaspx>.
Bay, J.C., "The Spore-Forming Species of the Genus *Saccharomyces*", The American Naturalist, Aug. 1893, pp. 685-696, vol. 27.
Canadian Intellectual Property Office, Office Action, Canadian Patent Application No. 8,839,383, dated May 30, 2018, four pages.
Communication pursuant to Article 94(3) EPC for European Patent Application No. EP 12739612.5, dated Jan. 12, 2017, 5 Pages.
Communication pursuant to Article 94(3) EPC for European Patent Application No. EP 12739612.5, dated Nov. 30, 2017, 5 Pages.
De Muynck, C. et al., "Potential of Selected Lactic Acid Bacteria to Produce Food Compatible Antifungal Metabolites," Microbiological Research 159, 2004, pp. 339-346.
El-Kholy et al., "Autolysis and intracellular enzyme release from cheese related dairy lactobacilli", Lait 1998, vol. 78, pp. 439-452.
European Patent Office, Partial Supplementary European Search Report, EP Patent Application No. 15839890.9, dated Jun. 1, 2018, 13 pages.
European Patent Office, Summons to Attend Oral Proceedings Pursuant to Rule 115(1) EPC, EP Patent Application No. 12739612.5, May 31, 2018, six pages.
Examination Report No. 1 for Australian Patent Application No. AU-2016204301, dated Sep. 20, 2016, 3 Pages.
Examination Report No. 2 for Australian Patent Application No. AU-2016204301, dated May 10, 2017, 3 Pages.
Examiner's Report No. 1 for Canadian Patent Application No. CA-2,839,383, dated Jul. 25, 2017, 5 Pages.
Extended European Search Report for European Patent Application No. EP 12739612.5, dated Jan. 20, 2016, 11 Pages.
Garcia-Kirchner, O., et al., "Mixed Submerged Fermentation with Two Filamentous Fungi for Cellulolytic Andxylanolytic Enzyme Production," Applied Biochemistry and Biotechnology, vol. 98-100, 2002, pp. 1105-1114.
Gutierrez Manero, F. et al., "Effects of Culture Filtrates of Rhizobacteria Isolated from Wild Lupine on Germination, Growth and Biological Nitrogen Fixation of Lupine Seedlinds," Journal of Plant Nutrition, vol. 26, No. 5, 2003, pp. 1101-1115.
Intellectual Property India, Examination Report under Sections 12 & 13 of the Patents Act, Indian Patent Application No. 7161/DELNP/2013, dated Jul. 4, 2018, eight pages.
Intellectual Property Office of Singapore, Written Opinion, Singapore Patent Application No. 11201701820V, dated Jan. 10, 2018, seven pages.
Kumar, S.K., et al., "Continuous hydrolysis of raffinose family oligosaccharides in soymilk by fluidized bed reactor", LWT—Food Science and Technology, 2010, pp. 220-225, vol. 43, No. 2.
Laitila, A. et al., "Antifungal Activites of Two Lactobacillus Plantarum Strains against Fusarium Moulds in vitro and in Malting of Barley," Journal of Applied Microbiology, 93, 2002, pp. 566-576.
Lee et al., "Unique Properties of Four Lactobacilli in Amino Acid Production and Symbiotic Mixed Culture for Lactic Acid Biosynthesis", Current Microbiology 2001, vol. 43, pp. 383-390.
Mukherjee, AK. et al., "Bioremediation and reclamation of soil contaminated with petroleum oil hydrocarbons by exogenously seeded bacterial consortium: a pilot-scale study", Environmental Science and Pollution Research, Sep. 2010, vol. 18, pp. 471-478.
PCT International Search Report & Written Opinion, International Application No. PCT/1B2016/000675, dated Sep. 8, 2016, 11 Pages.
Piggot, P., "Spore development in Bacillus subtilis", Current Opinion in Genetics & Development, Nov. 1996, pp. 531-537, vol. 6, No. 5.

(56) References Cited

OTHER PUBLICATIONS

Shim, Y. H., et al., "Evaluation of Multi-Microbial Probiotics Produced by Submerged Liquid and Solid Substrate Fermentation Methods in Broilers," Asian Australas. J. Anim. Sci., vol. 23, No. 4, Apr. 2010, pp. 521-529.

Third Office Action for Chinese Application No. CN 201280009159.9, dated Apr. 6, 2016, 8 Pages.

Wang, C., et al., "Microorganisms in Daqu: a Starter Culture of Chinese Maotai-flavor Liquor," World Journal of Microbiology and Biotechnology, Kluwer Academic Publishers, DO, vol. 24, No. 10, Mar. 24, 2008, pp. 2183-2190.

Keersmaecker, S.C.J. et al., "Strong antimicrobial activity of Lactobacillus rhamnosus GG against *Salmonella typimurium* is due to accumulation of lactic acid," FEMS Microbiology Letters, Jun. 1, 2006, vol. 259, No. 1, pp. 89-96.

Nunkaew, T. et al., "Effects of 5-aminolevulinic acid (ALA)-containing supernatants from selected Rhodopseudomonas palustris strains on rice growth under NaCl stress, with mediating effects on chlorophyll, photosynthetic electron transport and antioxidative enzymes," EJB Electronic Journal of Biotechnology, Jan. 1, 2014, vol. 17, No. 1, pp. 19-26.

Park, S.C. et al., "Isolation and Characterization of an Extracellular Antimicrobial Protein from Aspergillus oryzae," Journal of Agricultural and Food Chemistry, Oct. 22, 2008, Vo. 56, No. 20, pp. 9647-9652.

Pfeiffer, P. et al., "Purification and Characterization of Extracellular and Intracellular Killer Toxin of *Saccharomyces cerevisiae* Strain 28," Journal of General Microbiology, Nov. 1, 1982, pp. 2699-2706.

Stein, T., "Bacillus subtilis antibiotics: structures, syntheses and specific functions," Molecular Microbiology, May 1, 2005, vol. 56, No. 4, pp. 845-857.

Walker, G.M. et al., "Interaction Between Killer Yeasts and Pathogenic Fungi," FEBS Letters, Apr. 1, 1995, vol. 127, No. 3, pp. 213-222.

Wang, H. et al., "Production and characterization of antifungal compounds produced by Lactobacillus plantarum IMAU10014," PLOS ONE, Jan. 19, 2012, vol. 7, No. 1, p. e29452-1.

\* cited by examiner

Treatment

Treatment

Treatment

Treatment

Treatment

Treatment

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
caggcctaac acatgcaagt c                                            21

<210> SEQ ID NO 2
<211> LENGTH: 18
<212> TYPE: DNA
```

```
<213> ORGANISM: Artificial Sequence
<220> FEATURE:
<223> OTHER INFORMATION: Synthetic

<400> SEQUENCE: 2
acgggcggtg tgtacaag                                              18

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tccgtaggtg aaccttgcgg                                            20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
tcctccgctt attgatatgc                                            20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
agagtttgat cctggctcag                                            20

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
ggttaccttg ttacgactt                                             19
```

CELL FREE SUPERNATANT COMPOSITION OF MICROBIAL CULTURE FOR AGRICULTURAL USE

CROSS-REFERENCE TO RELATED APPLICATIONS

This application claims the benefit of U.S. Provisional Application No. 62/048,256, filed on Sep. 9, 2014, which is incorporated herein by reference in its entirety.

REFERENCE TO A SEQUENCE LISTING SUBMITTED AS A TEXT FILE VIA EFS-WEB

The Sequence Listing submitted Sep. 9, 2015 as a text file named "26148_0002U2_Seq_ST25.txt," created on Sep. 9, 2015, and having a size of 1,382 bytes is hereby incorporated by reference pursuant to 37 C.F.R. § 1.52(e)(5).

TECHNICAL FIELD

The present disclosure to compositions and methods for effectively improving plant growth responses, including, for example, germination rate, early plant growth, plant yield, and biomass by application of a disclosed composition.

BACKGROUND OF THE DISCLOSURE

Plant biostimulants are components other than fertilizers that affect plant growth and/or metabolism upon foliar application and/or when added to soil. Plant biostimulants include, but are not limited to, hormone-containing products, amino acid-containing products, and humic acid-containing products. Exemplary plant biostimulants include compositions based on seaweed extract, humic acid, amino acids, salicylic acid, bio-solids, hydrolyzed proteins, silicate, and/or synthetic compounds. Plant biostimulants are used to treat crops in a commercial setting, in part, due to their ability increase growth rates, decrease pest plant growth, increase stress tolerance, increase photosynthetic rate, and increase disease tolerance. Although the precise mechanism by which plant biostimulants exert their effect on plants, one hypothesis is that they operate by up-regulating or down-regulating plant hormones.

Despite advances in agricultural compositions and methods, there remains a need for compositions and methods that can perform plant biostimulation, i.e., improving plant growth responses and development, while reducing the use of chemical fertilizers. Methods and compositions disclosed herein may address these needs and others.

SUMMARY

In accordance with the disclosure herein, as embodied and broadly described herein, the disclosure, in one aspect, relates to compositions and methods for plant biostimulation. In various aspects, disclosed herein are compositions comprising a cell-free supernatant of a microbial culture comprising a mixture of microorganisms, which may comprise one or more of bacteria, fungi, algae, and/or microorganisms. Methods of the present disclosure comprise using compositions disclosed herein to enhance the growth of plants.

Disclosed are compositions comprising a cell-free supernatant of a microbial culture inoculated with an isolated microorganism, wherein the microorganism comprises one or more of *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof.

Also disclosed are methods of enhancing plant growth comprising providing the disclosed cell-free supernatant composition to a seed, to a plant, or to a plant at a particular growth stage, or combinations thereof, thereby enhancing plant growth. Growth is enhanced when a plant treated with a composition disclosed herein has growth characteristics that are different from, such as improved, compared to a plant grown under the same conditions that is not treated with the composition.

Also disclosed are methods of making an article comprising a cell-free supernatant comprising providing the disclosed cell-free supernatant composition to a surface of an article.

Also disclosed are methods for preparing a cell-free supernatant composition comprising the steps of: (a) inoculating a fermentation broth with one or more of an isolated microorganism, wherein the microorganism comprises *Aspergillus* spp., *Bacillus* spp., *Rhodopseudomonas* spp., *Candida* spp., *Lactobacillus* spp., *Pseudomonas* spp., *Saccharomyces* spp., or *Streptococcus* spp.; or combinations thereof; (b) incubating the inoculated fermentation broth for at least five hours; and (c) centrifuging the culture after step (b) for at least 10 minutes at a centrifugal force of 10,000×g; thereby providing the cell-free supernatant.

Also disclosed are cell-free supernatant compositions prepared by disclosed methods.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

FIG. 1A shows the effect of concentration of IN-M1 batch EA100510 cell-free supernatant (CFS) on percent difference in germination stimulation compared to control seeds treated with distilled water. FIG. 1B shows the data of FIG. 1A re-plotted to show the dilution of the CFS at which there is a prolonged effect versus time.

FIG. 2A shows the effect of concentration of IN-M1 batch EA110310 broth on percent difference in germination stimulation compared to control seeds treated with distilled water.

FIG. 2B shows the data of FIG. 2A re-plotted to show the dilution of the CFS at which there is a prolonged effect versus time.

FIG. 3A shows the effect of concentration of IN-M1 batch EA110310 broth on percent difference in germination stimulation compared to control seeds treated with distilled water. The number below each grouping of bars shows that time in hours at which germination was determined. FIG. 3B shows the data of FIG. 3A re-plotted to show the dilution of the CFS at which there is a prolonged effect versus time.

Figure 1A:
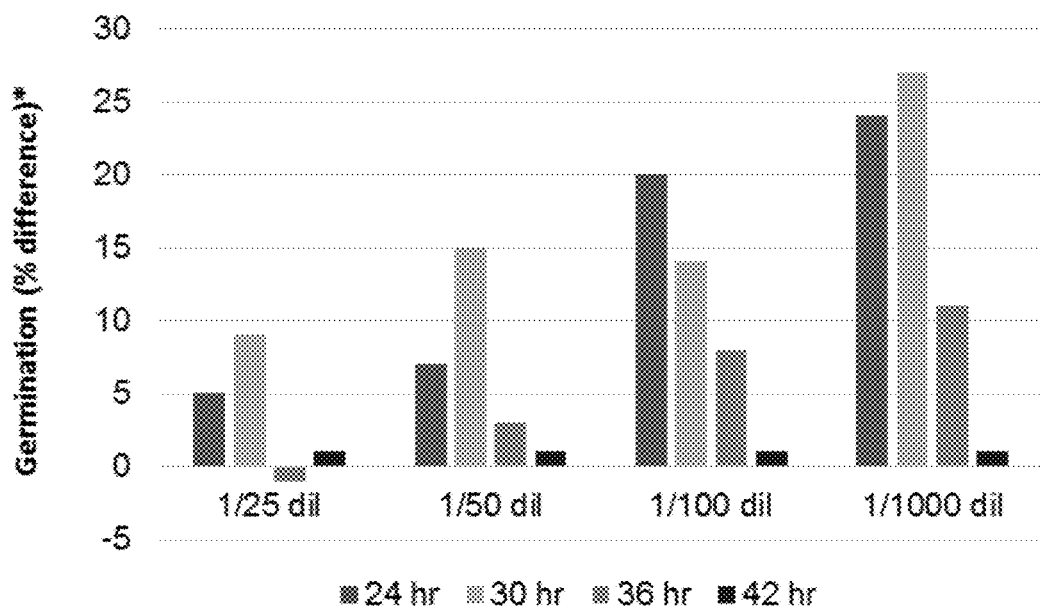
FIGS. 1A and 1B show representative data pertaining to the effect of disclosed compositions on germination.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein. Although any methods and materials similar or equivalent to those described herein can be used in the practice or testing of the present disclosure, example methods and materials are now described.

The terminology used herein is for the purpose of describing particular aspects only and is not intended to be limiting. In this specification and in the claims which follow, reference will be made to a number of terms which shall be defined to have the following meanings:

As used in the specification and the appended claims, the singular forms "a," "an," and "the" include plural referents unless the context clearly dictates otherwise. Thus, for example, reference to "a agronomically acceptable carrier" includes mixtures of two or more such carriers, and the like.

The word "or" as used herein means any one member of a particular list and also includes any combination of members of that list.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

As used herein, the term "gluconolactone(s)" is intended to include all isomer, solvate, hydrate, polymorphic, crystalline form, non-crystalline form, and salt variations of the following gluconolactone structure:

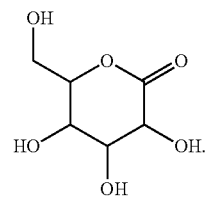

As used herein, the term "isomer(s)" is intended to include all stereoisomers of the compounds and/or molecules referred to herein (e.g., gluconolactones, LCOs, COs, chitinous compounds, flavonoids, jasmonic acid or derivatives thereof, linoleic acid or derivatives thereof, linolenic acid or derivatives thereof, kerrikins, etc.), including enantiomers, diastereomers, as well as all conformers, rotamers, and tautomers, unless otherwise indicated. The compounds and/or molecules disclosed herein include all enantiomers in either substantially pure levorotatory or dextrorotatory form, or in a racemic mixture, or in any ratio of enantiomers. Where aspects disclose a (D)-enantiomer, that aspect also includes the (L)-enantiomer; where aspects disclose a (L)-enantiomer, that aspect also includes the (D)-enantiomer. Where aspects disclose a (+)-enantiomer, that aspect also includes the (−)-enantiomer; where aspects disclose a (−)-enantiomer, that aspect also includes the (+)-enantiomer. Where aspects disclose a (S)-enantiomer, that aspect also includes the (R)-enantiomer; where aspects disclose a (R)-enantiomer, that aspect also includes the (S)-enantiomer. Aspects are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers, and tautomers of compounds and/or molecules depicted.

As used herein, the terms "effective amount", "effective concentration", or "effective dosage" is intended to mean the amount, concentration, or dosage of a biostimulant composition to cause enhanced plant growth. The actual effective dosage in absolute value depends on factors including, but not limited to, the size (e.g., the area, the total acreage, etc.) of the land for application with the biostimulant composition. The "effective amount", "effective concentration", or "effective dosage" of a biostimulant composition may be determined, e.g., by a routine dose response experiment.

As used herein, the term "carrier" is intended to include an "agronomically acceptable carrier." An "agronomically acceptable carrier" is intended to refer to any material which can be used to deliver a biostimulant composition as described herein, alone or in combination with one or more agriculturally beneficial ingredient(s), and/or biologically active ingredient(s), etc.) to a plant, a plant part (e.g., a seed), or a soil, and preferably a carrier can be added (to the plant, plant part (e.g., seed), or soil) without having an adverse effect on plant growth, soil structure, soil drainage or the like.

As used herein, the term "seed-compatible carrier" is intended to refer to any material which can be used to deliver a biostimulant composition as described herein, alone or in combination with one or more agriculturally beneficial ingredient(s), and/or biologically active ingredient(s), etc.) which can be added or applied to a seed without causing/having an adverse effect on the seed, the plant that grows from the seed, seed germination, or the like.

As used herein, the term "soil-compatible carrier" is intended to refer to any material which can be used to deliver a biostimulant composition as described herein, alone or in combination with one or more agriculturally beneficial ingredient(s), and/or biologically active ingredient(s), etc.) which can be added or applied to a soil without causing/having an adverse effect on plant growth, soil structure, soil drainage, or the like.

As used herein, the term "foliar-compatible carrier" is intended to refer to any material which can be used to deliver a biostimulant composition as described herein, alone or in combination with one or more agriculturally beneficial ingredient(s), and/or biologically active ingredient(s), etc.) which can be added to a plant or plant part without causing/having an adverse effect on the plant, plant part, plant growth, plant health, or the like.

As used herein, the term "micronutrient(s)" is intended to refer to nutrients which are beneficial for plant growth, plant health, and/or plant development.

As used herein, the term "herbicide(s)" is intended to refer to any agent or combination of agents capable of killing plants, such as weeds and/or inhibiting the growth of weeds (the inhibition being reversible under certain conditions).

As used herein, the term "fungicide(s)" is intended to refer to any agent or combination of agents capable of killing fungi and/or inhibiting fungal growth.

As used herein, the term "insecticide(s)" is intended to refer to any agent or combination of agents capable of killing one or more insects and/or inhibiting the growth of one or more insects.

As used herein, the term "agriculturally beneficial ingredient(s)" is intended to mean any agent or combination of agents capable of causing or providing a beneficial and/or useful effect in plant growth, production, soil, water, and plant agriculture in general.

As used herein, "biologically active ingredient" is intended to mean biologically active ingredients (e.g., signal molecules, other microorganisms, etc.) other than the one or more bacterial isolates described herein.

As used herein, the term "determining" can refer to measuring or ascertaining a quantity or an amount or a change in activity. For example, determining the characteristics of microorganisms or growing cultures as used herein can refer to the steps that the skilled person would take to measure or ascertain some quantifiable value in a sample. The art is familiar with the ways to measure characteristics in a sample. The term sample is used in its common meaning of a portion from a larger solution, from a site, from a culture, or other larger entity from which a portion, the sample, can be removed and optionally acted upon.

The term "biostimulation," as used herein, refers to the enhancement of metabolic and/or physiological processes within plants and/or soils. In a particular context, biostimulation refers to processes that stimulate the growth of plants, e.g., plants to which a biostimulant is applied.

As used herein, the term "biostimulant(s)" is intended to refer to any composition capable of enhancing metabolic or physiological processes within plants and soils. Unless clearly stated otherwise, a biostimulant may be comprised of a single ingredient or a combination of several different ingredients, and the enhanced plant metabolism and/or physiological processes may be attributed to one or more of the ingredients, either acting independently or in combination.

The term, "environment" as used herein, is an area as defined by the situation and includes the biotic and abiotic elements, and the patterns of the interrelationships between the biotic elements, and between the biotic and abiotic elements which are found in the defined area. All three physical states, solids, liquids and gases, are included in the elements which make up the environment.

As used herein, the term "microorganism" includes, but is not limited to, bacteria, viruses, fungi, algae, yeasts, protozoa, worms, spirochetes, single-celled, and multi-celled organisms that are included in classification schema as prokaryotes, eukaryotes, Archea, and Bacteria, and those that are known to those skilled in the art.

As used herein, term "enhanced plant growth" is intended to refer to increased plant yield (e.g., increased biomass, increased fruit number, or a combination thereof as measured by commonly used agricultural measurements, such as bushels per acre), increased root number, increased root mass, increased root volume, increased leaf area, increased plant stand, increased plant vigor, or combinations thereof.

As used herein, the terms "plant(s)" and "plant part(s)" are intended to refer to all plants and plant populations such as desired and undesired wild plants or crop plants (including naturally occurring crop plants). Crop plants can be plants, which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as seeds, shoot, leaf, flower and root, examples which may be mentioned being leaves, needles, stalks, stems, flowers, fruit bodies, fruits, seeds, roots, tubers and rhizomes. The plant parts also include harvested material and vegetative and generative propagation material (e.g., cuttings, tubers, rhizomes, off-shoots and seeds, etc.).

As used herein, the terms "microorganism" or "microbial" cover any generally unicellular organism, which can be propagated and manipulated in a laboratory. In the present disclosure, the terms preferably relate to bacteria and/or yeast and/or fungi. In the present disclosure, the term microorganism typically denotes a live microorganism, i.e., capable of propagation and/or having metabolic activity.

As used herein, the term "strain" refers in general to a closed population of organisms of the same species. Accordingly, the term "strain of lactic acid bacteria" generally refers to a strain of a species of lactic acid bacteria. More particularly, the term "strain" refers to members of a microbial species, wherein such members, i.e. strains, have different genotypes and/or phenotypes. Herein, the term "genotype" encompasses both the genomic and the recombinant DNA content of a microorganism. Herein, the term "phenotype" refers to observable physical characteristics dependent upon the genetic constitution of a microorganism. As one skilled in the art would recognize, microbial strains are thus composed of individual microbial cells having a common genotype and/or phenotype. Further, individual microbial cells may have specific characteristics (e.g., a specific rep-PCR pattern) which may identify them as belonging to their particular strain. A microbial strain can comprise one or more isolates of a microorganism.

As used herein, the term "inoculum" is intended to mean any form of microbial cells, or spores, which is capable of propagating in a culture medium.

The term "microbial composition or culture" intends to refer to a composition of microorganisms as disclosed herein, and used in methods as described herein. A microbial culture or microbial composition is made by inoculating a culture medium with microorganisms disclosed herein and allowing the microorganisms to grow, reproduce, etc. for a determined time period. Cell-free supernatant compositions disclosed and claimed herein result from and are made by removing the microorganisms from a microbial culture or microbial composition.

As used herein, the term "isolate" refers to cultured microorganisms grown from a single colony taken from a primary isolation plate. An isolate is presumed to be derived from a single microorganism.

As used herein, the term "isolated" as applied to a microorganism refers to a microorganism which has been removed and/or purified from an environment in which it naturally occurs. As such, an "isolated strain" of a microbe as used herein is a strain that has been removed and/or purified from its natural milieu. Thus, an "isolated microorganism" does not include one residing in an environment in which it naturally occurs. Further, the term "isolated" does not necessarily reflect the extent to which the microbe has been purified. Note that a strain associated with other strains, or with compounds or materials that it is not normally found with in nature, is still defined as "isolated."

As used herein, the term "substantially pure culture" refers to a strain or culture which contains substantially no other microbes than the desired strain or strains of microbe. In other words, a substantially pure culture of a strain of microbe is substantially free of other contaminants, which can include microbial contaminants as well as undesirable chemical contaminants.

As used herein, the term "biologically pure culture" is intended to mean a culture essentially free from biological contamination and having a genetic uniformity such that different subcultures taken therefrom will display substantially identical genotypes and phenotypes (e.g., cultures have a purity of at least 60%, of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, up to 100% pure). Further, as used herein, a "biologically pure" strain is intended to mean the strain separated from materials with which it is normally associated in nature.

"Culture medium" as used herein is defined as a mixture which supports the growth of microbial cells, which mixture may comprise, but is not limited to, ingredients such as carbohydrate or cellular energy sources, amino acid sources, peptone, soy peptone, and yeast extract powder. An aspect of the medium is its ability to support growth of the isolated microorganisms of the present disclosure.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

Compositions

In an aspect, disclosed compositions, referred to herein as a cell-free supernatant composition, comprise a cell-free supernatant of a microbial culture inoculated with one or more of an isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof. In an aspect, a cell-free supernatant composition is prepared by a disclosed method.

A composition comprising a cell-free supernatant of a microbial culture inoculated with one or more isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof. A composition comprising a cell-free supernatant of a microbial culture inoculated with a mixed culture, IN-M1, deposited with the ATCC Patent Depository under the Budapest Treaty (10801 University Blvd, Manassas, VA 20110), on Jan. 11, 2012, with the ATCC Patent Deposit Designation No. PTA-12383. A composition comprising a cell-free supernatant of a microbial culture inoculated with a mixed culture, IN-M2, deposited with the ATCC Patent Depository under the Budapest Treaty (10801 University Blvd, Manassas, VA 20110), on Sep. 4, 2014, with the designation IN-M2, under Account No. 200139, with the ATCC Patent Deposit Designation No. PTA-121556. Compositions disclosed herein wherein the cell-free supernatant is filter-sterilized. A cell-free supernatant composition disclosed further comprising an herbicide. A cell-free supernatant composition disclosed further comprising a pesticide. A cell-free supernatant composition disclosed further comprising a fungicide. A cell-free supernatant composition disclosed further comprising a liquid nutrient solution. A cell-free supernatant composition comprising IN-M1 and/or INM2, further comprising an herbicide, a pesticide, a fungicide, a liquid nutrient solution or combinations thereof.

A disclosed cell-free supernatant composition from a microbial culture wherein the *Aspergillus* spp. is *Aspergillus oryzae*, or wherein the *Aspergillus* spp. is *Aspergillus oryzae*, IN-AO1, deposited with the ATCC Patent Depository under the Budapest Treaty (10801 University Blvd, Manassas, VA 20110), on Sep. 4, 2014, with the designation IN-AO1, under Account No. 200139, with the ATCC Patent Deposit Designation No. PTA-121551. A disclosed cell-free supernatant composition from a microbial culture wherein the *Bacillus* spp. is *Bacillus subtilis* or wherein the *Bacillus* spp. is *Bacillus subtilis*, IN-BS1, deposited with the ATCC Patent Depository under the Budapest Treaty (10801 University Blvd, Manassas, VA 20110), on Jan. 11, 2012, with the ATCC Patent Deposit Designation No. PTA-12385. A disclosed cell-free supernatant composition from a microbial culture wherein the *Rhodopseudomonas* spp. is *Rhodopseudomonas palustris*, or wherein the *Rhodopseudomonas* spp. is *Rhodopseudomonas palustris*, IN-RP1, deposited with the ATCC Patent Depository under the Budapest Treaty (10801 University Blvd, Manassas, VA 20110), on Jan. 11, 2012, with the ATCC Patent Deposit Designation No, PTA-12387. A disclosed cell-free supernatant composition from a microbial culture wherein the *Candida* spp. is *Candida utilis* or wherein the *Candida* spp. is *Candida utilis*, IN-CU1, deposited with the ATCC Patent Depository under the Budapest Treaty (10801 University Blvd, Manassas, VA 20110), on Sep. 4, 2014, with the designation IN-CU1, under Account No. 200139, with the ATCC Patent Deposit Designation No. PTA-121550. A disclosed cell-free supernatant composition from a microbial culture wherein the *Lactobacillus* spp. is *Lactobacillus casei, Lactobacillus helveticus, Lactobacillus lactis, Lactobaccillus rhamnosus*, or *Lactobacillus plantarum*, or combinations thereof. A disclosed cell-free supernatant composition from a microbial culture wherein the *Lactobacillus* spp. is *Lactobacillus helveticus*, IN-LH1, deposited with the ATCC Patent Depository under the Budapest Treaty (10801 University Blvd, Manassas, VA 20110), on Jan. 11, 2012, with the ATCC Patent Deposit Designation No. PTA-12386. A disclosed cell-free supernatant composition from a microbial culture wherein the *Lactobacillus* spp. is *Lactobacillis casei*, referred to herein as IN-LC1, which was deposited with the ATCC Patent Depository under the Budapest Treaty (10801 University Blvd, Manassas, VA 20110), with the designation IN-LC1, on Sep. 4, 2014, under Account No. 200139, with the ATCC Patent Deposit Designation No. PTA-121549. A disclosed cell-free supernatant composition from a microbial culture wherein the *Lactobacillus* spp. is *Lactobacillis lactis*, referred to herein as IN-LL1, which was deposited with the ATCC Patent Depository under the Budapest Treaty (10801 University Blvd, Manassas, VA 20110), with the designation IN-LL1, on Sep. 4, 2014, under Account No. 200139, with the ATCC Patent Deposit Designation No. PTA-121552. A disclosed cell-free supernatant composition from a microbial culture wherein the *Lactobacillus* spp. is *Lactobacillus plantarum*, IN-LP1, deposited with the ATCC Patent Depository under the Budapest Treaty (10801 University Blvd, Manassas, VA 20110), on Sep. 4, 2014, with the designation IN-LP1, under Account No. 200139, with the ATCC Patent Deposit Designation No. PTA-121555. A disclosed com cell-free supernatant composition from a microbial culture position wherein the *Lactobacillus* spp. is *Lactobacillus rhamnosus*, IN-LR1, deposited with the ATCC Patent Depository under the Budapest Treaty (10801 University Blvd, Manassas, VA 20110), on Sep. 4, 2014, with the designation IN-LR1, under Account No. 200139, with the ATCC Patent Deposit Designation No. PTA-121554. A disclosed cell-free supernatant composition from a microbial culture wherein the *Pseudomonas* spp. is *Pseudomonas aeruginosa*. A disclosed cell-free supernatant composition from a microbial culture wherein the *Rhodopseudomonas* spp. is *Rhodopseudomonas palustris*. A disclosed cell-free supernatant composition from a microbial culture wherein the *Rhodopseudomonas* spp. is *Rhodopseudomonas palustris*, IN-RP1, deposited with the ATCC Patent Depository under the Budapest Treaty (10801 University Blvd, Manassas, VA 20110), on Jan. 11, 2012, with the ATCC Patent Deposit Designation No. PTA 12387. A disclosed cell-free supernatant composition from a microbial culture wherein the *Rhodopseudomonas* spp. is *Rhodopseudomonas palustris*, IN-RP2, deposited with the ATCC Patent Depository under the Budapest Treaty (10801 University Blvd, Manassas, VA 20110), on Sep. 4, 2014, with the designation IN-RP2, under Account No. 200139, with the ATCC Patent Deposit Designation No. PTA-121553. A disclosed cell-free supernatant composition from a microbial culture wherein the *Saccharomyces* spp. is *Saccharomyces cerevisiae*. A disclosed cell-free supernatant composition from a microbial culture wherein the *Saccharomyces* spp. is *Saccharomyces cerevisiae*, IN-SC1, deposited with the ATCC Patent Depository under the Budapest Treaty (10801 University Blvd, Manassas, VA 20110), on Jan. 11, 2012, with the ATCC Patent Deposit Designation No. PTA-12384. A disclosed cell-free supernatant composition from a microbial culture wherein the *Streptococcus* spp. is *Streptococcus lactis*. A disclosed cell-free supernatant composition from a microbial culture further comprising at least one isolated micorrhyzal fungus. A disclosed cell-free supernatant composition from a microbial culture wherein the microbial culture is inoculated with of at least two of *Aspergillus* spp., *Bacillus* spp., *Rhodopseudomonas* spp., *Candida* spp., *Lactobacillus* spp., *Pseudomonas* spp., *Saccharomyces* spp., or *Streptococcus* spp. A disclosed cell-free supernatant composition from a microbial culture wherein the microbial culture is inoculated with *Aspergillus oryzae, Bacillus subtilis, Lactobacillus helveticus, Lactobacillus casei, Rhodopseudomonas palustris*, and *Saccharomyces cervisiase*.

In an aspect, a cell-free supernatant composition is filter-sterilized. In an aspect, a cell-free supernatant composition may further comprise one or more of an herbicide, a pesticide, a fungicide, a liquid nutrient composition, or other compounds or compositions that may aid the growth of the desired plants or inhibit the growth of undesired plants, insects, nematodes or other plant pests.

In various aspects, a cell-free supernatant composition can be in the form of a liquid, a gel, a slurry, a solid, or a powder (wettable powder or dry powder). In further aspects, a cell-free supernatant composition can be in the form of a seed coating. Compositions in liquid, slurry, or powder (e.g., wettable powder) form can be suitable for coating seeds. When used to coat seeds, a cell-free supernatant composition can be applied to the seeds and allowed to dry. In various aspects, a cell-free supernatant composition can be formulated as a powder (e.g., a wettable powder), a liquid, such as water, can be added to the powder before application to a seed.

A cell-free supernatant composition disclosed herein may optionally include one or more biologically active ingredients as described herein, other than the one or more gluconolactones described herein. Non-limiting examples of biologically active ingredients include plant signal molecules (e.g., lipo-chitooligosaccharides (LCO), chitooligosaccharides (CO), chitinous compounds, flavonoids, jasmonic acid or derivatives thereof, linoleic acid or derivatives thereof, linolenic acid or derivatives thereof, karrikins, etc.) and one or more beneficial microorganisms (e.g., *Rhizobium* spp., *Bradyrhizobium* spp., *Sinorhizobium* spp., *Azorhizobium* spp., *Glomus* spp., *Gigaspora* spp., *Hymenoscyphous* spp., *Oidiodendron* spp., *Laccaria* spp., *Pisolithus* spp., *Rhizopogon* spp., *Scleroderma* spp., *Rhizoctonia* spp., *Acinetobacter* spp., *Arthrobacter* spp, *Arthrobotrys* spp., *Aspergillus* spp., *Azospirillum* spp, *Bacillus* spp, *Burkholderia* spp., *Candida* spp., *Chryseomonas* spp., *Enterobacter* spp., *Eupenicillium* spp., *Exiguobacterium* spp., *Klebsiella* spp., *Kluyvera* spp., *Microbacterium* spp., *Mucor* spp., *Paecilomyces* spp., *Paenibacillus* spp., *Penicillium* spp., *Pseudomonas* spp., *Serratia* spp., *Stenotrophomonas* spp., *Streptomyces* spp., *Streptosporangium* spp., *Swaminathania* spp., *Thiobacillus* spp., *Torulospora* spp., *Vibrio* spp., *Xanthobacter* spp., *Xanthomonas* spp., etc.).

In an aspect, a cell-free supernatant composition may comprise a liquid nutrient solution. As used herein, the term "liquid nutrient solution" refers to a liquid which contains nutrients, including, but not limited to, energy source molecules (e.g., glucose), amino acids, vitamins, minerals, cofactors for plant metabolism, in the solution or in the mixture. A liquid nutrient solution is intended to comprise any liquid which enables plant growth including oxygenated or aerated water mixtures which may or may not contain added nutrients.

In an aspect, a cell-free supernatant composition can comprise one or more beneficial micronutrients. Non-limiting examples of micronutrients for use in the compositions described herein include vitamins, (e.g., vitamin A, vitamin B complex (i.e., vitamin B1, vitamin B2, vitamin B3, vitamin B5, vitamin B6, vitamin B7, vitamin B8, vitamin B9, vitamin B12, choline) vitamin C, vitamin D, vitamin E, vitamin K, carotenoids (α-carotene, β-carotene, cryptoxanthin, lutein, lycopene, zeaxanthin, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), organic acids (e.g., acetic acid, citric acid, lactic acid, malic aclid, taurine, etc.), and combinations thereof. In an aspect, a composition may comprise phosphorous, boron, chlorine, copper, iron, manganese, molybdenum, zinc or combinations thereof.

In certain aspects, where compositions described herein may comprise phosphorous, it is envisioned that any suitable source of phosphorous may be provided. In one aspect, the phosphorus may be derived from a source. In another aspect, suitable sources of phosphorous include phosphorous sources capable of solubilization by one or more microorganisms (e.g., *Penicillium bilaiae*, etc.). In an aspect, the phosphorus may be derived from a rock phosphate source. In another aspect the phosphorous may be derived from fertilizers comprising one or more phosphorous sources. Commercially available manufactured phosphate fertilizers are of many types. Some common ones are those containing rock phosphate, monoammonium phosphate, diammonium phosphate, monocalcium phosphate, super phosphate, triple super phosphate, and/or ammonium polyphosphate. All of these fertilizers are produced by chemical processing of insoluble natural rock phosphates in large scale fertilizer-manufacturing facilities and the product is expensive. By means of the present disclosure it is possible to reduce the amount of these fertilizers applied to the soil while still maintaining the same amount of phosphorus uptake from the soil.

In still another aspect, the phosphorous may be derived from an organic phosphorous source. In a further particular aspect, the source of phosphorus may include an organic fertilizer. An organic fertilizer refers to a soil amendment derived from natural sources that provide, at least, some percentages of nitrogen, phosphate, and/or potash. Non-limiting examples of organic fertilizers include plant and animal by-products, rock powders, seaweed, inoculants, and conditioners. These are often available at garden centers and through horticultural supply companies. Sources of phosphorus may from bone meal, meat meal, animal manure, compost, sewage sludge, or guano, or combinations thereof.

In an aspect, the phosphorous may be derived from a combination of phosphorous sources including, but not limited to, rock phosphate, fertilizers comprising one or more phosphorous sources (e.g., monoammonium phosphate, diammonium phosphate, monocalcium phosphate, super phosphate, triple super phosphate, ammonium polyphosphate, etc.) one or more organic phosphorous sources, and combinations thereof.

In an aspect, a cell-free supernatant composition may comprise one or more beneficial biostimulants. Biostimulants may enhance metabolic or physiological processes such as respiration, photosynthesis, nucleic acid uptake, ion uptake, nutrient delivery, or a combination thereof. Non-limiting examples of biostimulants include seaweed extracts (e.g., ascophyllum nodosum), humic acids (e.g., potassium humate), fulvic acids, myo-inositol, glycine, and combinations thereof. In an aspect, compositions may comprise seaweed extracts, humic acids, fulvic acids, myo-inositol, glycine, or combinations thereof.

In an aspect, a cell-free supernatant composition may comprise one or more plant signal molecules. In an aspect, the one or more plant signal molecules are one or more LCOs. In an aspect, the one or more plant signal molecules are one or more COs. In an aspect, the one or more plant signal molecules are one or more chitinous compounds. In an aspect, the one or more plant signal molecules are one or more flavonoids or derivatives thereof. In an aspect, the one or more plant signal molecules are one or more non-flavonoid nod gene inducers (e.g., jasmonic acid, linoleic acid, linolenic acid, and derivatives thereof). In an aspect, the one or more plant signal molecules are one or more karrikins or derivatives thereof. In an aspect, the one or more plant signal molecules are one or more LCOs, one or more COs, one or more chitinous compounds, one or more flavonoids and derivatives thereof, one or more non-flavonoid nod gene inducers and derivatives thereof, one or more karrikins and derivatives thereof, or any signal molecule combinations thereof.

Lipo-chitooligosaccharide compounds (LCOs), also known as symbiotic Nod signals or Nod factors, consist of an oligosaccharide backbone of β-I,4-linked N-acetyl-D-glucosamine ("GlcNAc") residues with an N-linked fatty acyl chain condensed at the non-reducing end. LCO's differ in the number of GlcNAc residues in the backbone, in the length and degree of saturation of the fatty acyl chain, and in the substitutions of reducing and non-reducing sugar residues. LCOs are intended to include all LCOs as well as isomers, salts, and solvates thereof. LCOs may be obtained (isolated and/or purified) from bacteria such as *Rhizobia*, e.g., *Rhizobium* spp., *Bradyrhizobium* spp., *Sinorhizobium* spp. and *Azorhizobium* spp. LCO structure is characteristic for each such bacterial species, and each strain may produce multiple LCO's with different structures.

LCOs from *Bradyrhizobium japonicum* are described in U.S. Pat. Nos. 5,175,149 and 5,321,011. Broadly, they are pentasaccharide phytohormones comprising methylfucose. A number of these *B. japonicum*-derived LCOs are described: BjNod-V (C18:1); BjNod-V (AC, C18:1), BjNod-V (C16:1); and BjNod-V (AC, C16:0), with "V" indicating the presence of five N-acetylglucosamines; "Ac" an acetylation; the number following the "C" indicating the number of carbons in the fatty acid side chain; and the number following the ":" the number of double bonds.

LCOs used in compositions of the disclosure may be obtained (i.e., isolated and/or purified) from bacterial strains that produce LCO's, such as strains of *Azorhizobium, Bradyrhizobium* (including *B. japonicum*), *Mesorhizobium, Rhizobium* (including *R. leguminosarum*), *Sinorhizobium* (including *S. meliloti*), and bacterial strains genetically engineered to produce LCO's.

Also encompassed by the present disclosure are compositions using LCOs obtained (i.e., isolated and/or purified) from a mycorrhizal fungus, such as fungi of the group Glomerocycota, e.g., *Glomus intraradicus*. The structures of representative LCOs obtained from these fungi are described in WO 2010/049751 and WO 2010/049751 (the LCOs described therein also referred to as "Myc factors").

Compositions of the present disclosure may comprise synthetic LCO compounds, such as those described in WO 2005/063784, and recombinant LCO's produced through genetic engineering. The basic, naturally occurring LCO structure may contain modifications or substitutions found in naturally occurring LCOs, such as those described in Spaink, Crit. Rev. Plant Sci. 54:257-288 (2000) and D'Haeze, et al., Glycobiology 12:79R-105R (2002). Precursor oligosaccharide molecules (COs, which as described below, are also useful as plant signal molecules in the present disclosure) for the construction of LCOs may also be synthesized by genetically engineered organisms, e.g., as in Samain, et al., Carb. Res. 302:35-42 (1997); Samain, et al., J. Biotechnol. 72:33-47 (1999).

LCOs may be utilized in various forms of purity and may be used alone or in the form of a culture of LCO-producing bacteria or fungi. Methods to provide substantially pure LCOs include removing the microbial cells from a mixture of LCOs and microbial cells, or further steps to isolate and purify the LCO molecules through LCO solvent phase separation followed by HPLC chromatography as described, for example, in U.S. Pat. No. 5,549,718. Purification can be enhanced by repeated HPLC, and the purified LCO molecules can be freeze-dried for long-term storage.

Chitooligosaccharides (COs) are known in the art as β-1-4 linked N-actylglucosamine structures identified as chitin oligomers, also as N-acetylchitooligosaccharides. COs have unique and different side chain decorations which make them different from chitin molecules [(C8H13N05)n, CAS No. 1398-61-4], and chitosan molecules [(C5H11NO4)n, CAS No. 9012-76-4]. Representative literature describing the structure and production of COs is as follows: Van der Hoist, et al., Current Opinion in Structural Biology, 11:608-616 (2001); Robina, et al., Tetrahedron 58:521-530 (2002); Hanel, et al., Planta 232:787-806 (2010); Rouge, et al. Chapter 27, "The Molecular Immunology of Complex Carbohydrates" in Advances in Experimental Medicine and Biology, Springer Science; Wan, et al., Plant Cell 21:1053-69 (2009); PCT/F100/00803 (Sep. 21, 2000); and Demont-Caulet, et al., Plant Physiol. 120(1):83-92 (1999). The COs may be synthetic or recombinant. Methods for preparation of recombinant COs are known in the art. See, e.g., Samain, et al. (supra.); Cottaz, et al., Meth. Eng. 7(4):311-7 (2005) and Samain, et al., J. Biotechnol. 72:33-47 (1999). COs are intended to include isomers, salts, and solvates thereof.

Chitins and chitosans, which are major components of the cell walls of fungi and the exoskeletons of insects and crustaceans, are also composed of GlcNAc residues. Chitinous compounds include chitin, (IUPAC: N-[5-[[3-acetylamino-4,5-dihydroxy-6-(hydroxymethyl)oxan-2yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), chitosan, (IUPAC: 5-amino-6-[5-amino-6-[5-amino-4,6-dihydroxy-2(hydroxymethyl) oxan-3-yl]oxy-4-hydroxy-2-(hydroxymethyl)oxan-3-yl] oxy-2(hydroxymethyl)oxane-3,4-diol), and isomers, salts, and solvates thereof.

These compounds may be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells), Pochanavanich, et al., Lett. Appl. Microbiol. 35:17-21 (2002) (preparation from fungal cell walls), and U.S. Pat. No. 5,965,545 (preparation from crab shells and hydrolysis of commercial chitosan). Deacetylated chitins and chitosans may be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are also commercially available. Commercial products include, for example, ELEXA® (Plant Defense Boosters, Inc.) and BEYOND™ (Agrihouse, Inc.).

Flavonoids are phenolic compounds having the general structure of two aromatic rings connected by a three-carbon bridge. Flavonoids are produced by plants and have many functions, e.g., as beneficial signaling molecules, and as protection against insects, animals, fungi and bacteria. Classes of flavonoids include chalcones, anthocyanidins, coumarins, flavones, flavanols, flavonols, flavanones, and isoflavones. See, Jain, et al., J. Plant Biochem. & Biotechnol. 11:1-10 (2002); Shaw, et al., Environmental Microbiol. 11:1867-80 (2006).

Representative flavonoids that may be useful in compositions of the present disclosure include luteolin, apigenin, tangeritin, quercetin, kaempferol, myricetin, fisetin, isorhamnetin, pachypodol, rhamnazin, hesperetin, naringenin, formononetin, eriodictyol, homoeriodictyol, taxifolin, dihydroquercetin, dihydrokaempferol, genistein, daidzein, glycitein, catechin, gallocatechin, catechin 3-gallate, gallocatechin 3-gallate, epicatechin, epigallocatechin, epicatechin 3-gallate, epigallocatechin 3-gallate, cyaniding, delphinidin, malvidin, pelargonidin, peonidin, petunidin, or derivatives thereof. Flavonoid compounds are commercially available, e.g., from Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston, et al., Plant Physiology 137:1375-88 (2005). Flavonoid compounds are intended to include all flavonoid compounds as well as isomers, salts, and solvates thereof.

Jasmonic acid (JA, [1R-[1α,2β(Z)]]-3-oxo-2-(pentenyl) cyclopentaneacetic acid) and its derivatives, linoleic acid ((Z,Z)-9,12-Octadecadienoic acid) and its derivatives, and linolenic acid ((Z,Z,Z)-9,12,15-octadecatrienoic acid) and its derivatives, may also be used in the compositions described herein. Non-flavonoid nod-gene inducers are intended to include not only the non-flavonoid nod-gene inducers described herein, but isomers, salts, and solvates thereof.

Jasmonic acid and its methyl ester, methyl jasmonate (MeJA), collectively known as jasmonates, are octadecanoid-based compounds that occur naturally in plants. Jasmonic acid is produced by the roots of wheat seedlings, and by fungal microorganisms such as *Botryodiplodia theobromae* and *Gibberella fujikuroi*, yeast (*Saccharomyces cerevisiae*), and pathogenic and non-pathogenic strains of *Escherichia coli*. Linoleic acid and linolenic acid are produced in the course of the biosynthesis of jasmonic acid. Jasmonates, linoleic acid and linolenic acid (and their derivatives) are reported to be inducers of nod gene expression or LCO production by rhizobacteria. See, e.g., Mabood, Fazli, Jasmonates induce the expression of nod genes in *Bradyrhizobium japonicum*, May 17, 2001; and Mabood, Fazli, "Linoleic and linolenic acid induce the expression of nod genes in *Bradyrhizobium japonicum*," USDA 3, May 17, 2001.

Useful derivatives of linoleic acid, linolenic acid, and jasmonic acid that may be useful to add to the cell-free supernatant compositions include esters, amides, glycosides and salts. Representative esters are compounds in which the carboxyl group of linoleic acid, linolenic acid, or jasmonic acid has been replaced with a —COR group, where R is an —OR1 group, in which R1 is: an alkyl group, such as a C1-C8 unbranched or branched alkyl group, e.g., a methyl, ethyl or propyl group; an alkenyl group, such as a C2-C8 unbranched or branched alkenyl group; an alkynyl group, such as a C2-C8 unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an NR2R3 group, in which R2 and R3 are independently: hydrogen; an alkyl group, such as a C1-C8 unbranched or branched alkyl group, e.g., a methyl, ethyl or propyl group; an alkenyl group, such as a C2-C8 unbranched or branched alkenyl group; an alkynyl group, such as a C2-C8 unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid, and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salt may be precipitated from solution and be collected by filtration or may be recovered by other means such as by evaporation of the solvent.

Karrikins are vinylogous 4H-pyrones e.g., 2H-furo[2,3-c]pyran-2-ones including derivatives and analogues thereof. It is intended that the karrikins include isomers, salts, and solvates thereof.

In an aspect, a cell-free supernatant composition may further comprise one or more gluconolactones. The one or more gluconolactones may be a natural gluconolactone (i.e., not synthetically produced), a synthetic gluconolactone (e.g., a chemically synthesized gluconolactone) or a combination thereof.

In an aspect, a cell-free supernatant composition may comprise an herbicide. Exemplary herbicides include, but are not limited to, imidazolinone, sulfonylurea, glyphosate, glufosinate, L-phosphinothricin, triazine, benzonitrile, Dicamba (3,6-dichloro-o-anisic acid or 3,6-dichloro-2-methoxybenzoic acid), the active ingredient in herbicides such as BANVEL™ (BASF), CLARITY™ (BASF), and VANQUISH™ (Syngenta), pyrethrins and synthetic pyrethroids; azoles, oxadizine derivatives; chloronicotinyls; nitroguanidine derivatives; triazoles; organophosphates; pyrrols; pyrazoles; phenyl pyrazoles; diacylhydrazines; and carbamates. Additional examples of herbicides within some of the above-listed categories can be found in The Pesticide Manual, 12th Ed., C. D. S. Tomlin, Ed., British Crop Protection Council, Farnham, Surry, UK (2000).

In an aspect, a cell-free supernatant composition may comprise a pesticide. Exemplary pesticides include, but are not limited to, any bacterial species (i.e., *Bacillus thuringiensis*), viruses (i.e., densoviruses), biocontrol pesticides, abamectin, phostoxin/fumitoxin, bifenthrin, carbaryl, chlorfenapyr, beta-cyfluthrin, cypermethrin, deltamethrin, dichlorvos, D-phenothrin, D-trans allethrin, resmethrin, methomyl, hydramethylnon, fenoxycarb, fipronil, imidacloprid, imidacloprid, lambda-cyhalothrin, malathion, methoprene, naled, nithiazine, P-dichlorobenzene, permethrin, permethrin-piperonyl butoxide, propetamphos, propoxur, pyrethrins, phenothrin, allethrin, hydroprene, resmethrin, spinosad, sumthrin, sumthrin-piperonyl butoxide, temephos, mosquito larvicide, pupicide, or any combination thereof.

In an aspect, a cell-free supernatant composition may comprise a fungicide. Exemplary fungicides include, but are not limited to, Mefenoxam & Fludioxonil (ApronMaxx RTA, Syngenta USA), tebuconazole, simeconazole, fluquinconazole, difenoconazole, 4,5-dimethyl-N-(2-propenyl)-2-(trimethyl silyl)-3-thiophenecarboxamide (silthiopham), hexaconazole, etaconazole, propiconazole, triticonazole, flutriafol, epoxiconazole, fenbuconazole, bromuconazole, penconazole, imazalil, tetraconazole, flusilazole, metconazole, diniconazole, myclobutanil, triadimenol, bitertanol, pyremethanil, cyprodinil, tridemorph, fenpropimorph, kresoxim-methyl, azoxystrobin, ZEN90160, fenpiclonil, benalaxyl, furalaxyl, metalaxyl, R-metalaxyl, orfurace, oxadixyl, carboxin, prochloraz, trifulmizole, pyrifenox, acibenzolar-5-methyl, chlorothalonil, cymoaxnil, dimethomorph, famoxadone, quinoxyfen, fenpropidine, spiroxamine, triazoxide, BAS50001 F, hymexazole, pencycuron, fenamidone, guazatine, and cyproconazole.

In an aspect, a cell-free supernatant composition may comprise a one or more insecticides. Insecticides useful to the compositions described herein will suitably exhibit activity against a broad range of insects including, but not limited to, wireworms, cutworms, grubs, corn rootworm, seed corn maggots, flea beetles, chinch bugs, aphids, leaf beetles, stink bugs, and combinations thereof.

Non-limiting examples of commercial insecticides which may be suitable for compositions disclosed herein include CRUISER (Syngenta, Wilmington, Del.), GAUCHO and PONCHO (Gustafson, Plano, Tex.). Active ingredients in these and other commercial insecticides include thiamethoxam, clothianidin, and imidacloprid. Commercial insecticides are most suitably used in accordance with the manufacturer's instructions at the recommended concentrations.

In various aspects, the cell-free supernatant composition comprises volatile fatty acids. In a further aspect, the volatile fatty acids comprise acetic acid, butyric acid, isobutyric acid, and propionic acid. In various aspects, the volatile fatty acid concentrations can be adjusted by fermentation conditions (including choice of microorganisms in the culture) and/or addition of purified volatile fatty acids to cell-free supernatant in order to achieve a desired concentration.

In a further aspect, the concentration of acetic acid in the cell-free supernatant is about 2000-2400 ppm. In a still further aspect, the concentration of butyric acid in the cell-free supernatant is about 1300-1800 ppm. In a yet further aspect, the concentration of isobutyric acid in the cell-free supernatant is about 200-700 ppm. In an even further aspect, the concentration of propionic acid in the cell-free supernatant is about 100-1200 ppm.

In a further aspect, the concentration of acetic acid in the cell-free supernatant is about 2000-2400 ppm. In a still further aspect, the concentration of butyric acid in the cell-free supernatant is about 1300-1750 ppm. In a yet further aspect, the concentration of isobutyric acid in the cell-free supernatant is about 600-650 ppm. In an even further aspect, the concentration of propionic acid in the cell-free supernatant is about 140-1100 ppm.

In a further aspect, the ratio of acetic acid, butyric acid, isobutyric acid, and proprionic acid is a fixed ratio. In a still further aspect, the ratio is a ratio determined by the levels of cetic acid, butyric acid, isobutyric acid, and proprionic acid as provided herein.

In an aspect, a cell-free supernatant composition may be prepared from a microbial culture that comprises at least one isolated micorrhyzal fungus. Micorrhyzal fungi increase nutrient uptake in plants by increasing the surface absorbing area of the roots and by releasing powerful enzymes into the soil that dissolve hard-to-capture nutrients, including organic nitrogen, phosphorus, iron and other "tightly bound" soil nutrients. This extraction process is useful in plant nutrition and may indicate why non-micorrhyzal plants require high levels of fertilizer to maintain their health. Micorrhyzal fungi form an intricate web that captures and assimilates nutrients, conserving the nutrient capital in soils.

In an aspect, a cell-free supernatant composition can comprise an agronomically acceptable carrier. Carriers described herein may allow a cell-free supernatant composition to remain efficacious (e.g., capable of increasing plant growth). Non-limiting examples of cell-free supernatant composition comprising a carrier include liquids, gels, slurries, or solids (including wettable powders or dry powders). The selection of the carrier material will depend on the intended application. A carrier may, for example, be a soil-compatible carrier, a seed-compatible carrier and/or a foliar-compatible carrier. In an aspect, a carrier is a soil compatible carrier. In an aspect, a carrier is a seed-compatible carrier. In an aspect, a carrier is a foliar-compatible carrier.

In an aspect, a carrier is a liquid carrier. Non-limiting examples of liquids useful as carriers for compositions disclosed herein include water, an aqueous solution, or a non-aqueous solution. In an aspect, a carrier is water. In an aspect, a carrier is an aqueous solution. In an aspect, a carrier is a non-aqueous solution. If a liquid carrier is used, the liquid (e.g., water) carrier may further include growth media to culture one or more microbial strains used in the compositions described. Non-limiting examples of suitable growth media for microbial strains include YEM media, mannitol yeast extract, glycerol yeast extract, Czapek-Dox medium, potato dextrose broth, or any media known to those skilled in the art to be compatible with, and/or provide growth nutrients to microbial strain which may be included to the compositions described herein.

In an aspect, the carrier is water. In an aspect, a cell-free supernatant is diluted in water. In an aspect, a cell-free supernatant is diluted in water from a stock concentration of cell-free supernatant to about 1/10, 1/20, 1/30, 1/40, 1/50, 1/60, 1/70, 1/80, 1/90, 1/100, 1/150, or 1/200 in water.

In an aspect, a cell-free supernatant compositions described herein may comprise one or more polymers. Non-limiting uses of polymers in the agricultural industry include agrochemical delivery, heavy metal removal, water retention and/or water delivery, and combinations thereof. Pouci, et al., Am. J. Agri. & Biol. Sci., 3(1):299-314 (2008).

In an aspect, the one or more polymers is a natural polymer (e.g., agar, starch, alginate, pectin, cellulose, etc.), a synthetic polymer, a biodegradable polymer (e.g., polycaprolactone, polylactide, poly(vinyl alcohol), etc.), or a combination thereof.

For a non-limiting list of polymers useful for compositions described herein, see Pouci, et al., Am. J. Agri. & Biol. Sci., 3(1):299-314 (2008). In an aspect, compositions described herein may comprise cellulose, cellulose derivatives, methylcellulose, methylcellulose derivatives, starch, agar, alginate, pectin, polyvinylpyrrolidone, and combinations thereof.

In an aspect, cell-free supernatant compositions described herein may comprise one or more wetting agents. Wetting agents are commonly used on soils, particularly hydrophobic soils, to improve the infiltration and/or penetration of water into a soil. The wetting agent may be an adjuvant, oil, surfactant, buffer, acidifier, or combination thereof. In an aspect, the wetting agent is a surfactant. In an aspect, the wetting agent is one or more nonionic surfactants, one or more anionic surfactants, or a combination thereof. In an aspect, the wetting agent is one or more nonionic surfactants.

In an aspect, a cell-free supernatant composition may comprise a surfactant. Surfactants suitable for compositions described herein may be non-ionic surfactants (e.g., semipolar and/or anionic and/or cationic and/or zwitterionic). The surfactants can wet and emulsify soil(s) and/or dirt(s). It is envisioned that the surfactants used in described composition have low toxicity for any microorganisms contained within the formulation. It is further envisioned that the surfactants used in described compositions have a low phytotoxicity (i.e., the degree of toxicity a substance or combination of substances has on a plant). A single surfactant or a blend of several surfactants can be used.

Anionic surfactants or mixtures of anionic and nonionic surfactants may also be used in compositions disclosed herein. Anionic surfactants are surfactants having a hydrophilic moiety in an anionic or negatively charged state in aqueous solution. Compositions described herein may comprise one or more anionic surfactants. The anionic surfactant(s) may be either water soluble anionic surfactants, water insoluble anionic surfactants, or a combination of water soluble anionic surfactants and water insoluble anionic surfactants. Non-limiting examples of anionic surfactants include sulfonic acids, sulfuric acid esters, carboxylic acids, and salts thereof. Non-limiting examples of water soluble anionic surfactants include alkyl sulfates, alkyl ether sulfates, alkyl amido ether sulfates, alkyl aryl polyether sulfates, alkyl aryl sulfates, alkyl aryl sulfonates, monoglyceride sulfates, alkyl sulfonates, alkyl amide sulfonates, alkyl aryl sulfonates, benzene sulfonates, toluene sulfonates, xylene sulfonates, cumene sulfonates, alkyl benzene sulfonates, alkyl diphenyloxide sulfonate, alpha-olefin sulfonates, alkyl naphthalene sulfonates, paraffin sulfonates, lignin sulfonates, alkyl sulfosuccinates, ethoxylated sulfosuccinates, alkyl ether sulfosuccinates, alkylamide sulfosuccinates, alkyl sulfosuccinamate, alkyl sulfoacetates, alkyl phosphates, phosphate ester, alkyl ether phosphates, acyl sarconsinates, acyl isethionates, N-acyl taurates, N-acyl-N-alkyltaurates, alkyl carboxylates, or a combination thereof.

Nonionic surfactants are surfactants having no electrical charge when dissolved or dispersed in an aqueous medium. Composition described herein may comprise one or more nonionic surfactants that are used to provide the desired wetting and emulsification actions and do not significantly inhibit spore stability and activity. The nonionic surfactant (s) may be either water soluble nonionic surfactants, water insoluble nonionic surfactants, or a combination of water soluble nonionic surfactants and water insoluble nonionic surfactants.

Non-limiting examples of water insoluble nonionic surfactants include alkyl and aryl: glycerol ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty esters, or combinations thereof. Also included are EO/PO block copolymers (EO is ethylene oxide, PO is propylene oxide), EO polymers and copolymers, polyamines, and polyvinylpynolidones.

Non-limiting examples of water soluble nonionic surfactants include sorbitan fatty acid alcohol ethoxylates and sorbitan fatty acid ester ethoxylates.

In an aspect, compositions described herein comprise at least one or more nonionic surfactants. In an aspect, compositions comprise at least one water insoluble nonionic surfactant and at least one water soluble nonionic surfactant. In an aspect, compositions comprise a combination of non-ionic surfactants having hydrocarbon chains of substantially the same length.

In an aspect, compositions described herein may comprise organosilicone surfactants, silicone-based antifoams used as surfactants in silicone-based and mineral-oil based antifoams. In an aspect, compositions described herein may comprise alkali metal salts of fatty acids (e.g., water soluble alkali metal salts of fatty acids and/or water insoluble alkali metal salts of fatty acids).

Microbial Cultures Inoculated with Isolated Microorganisms

Cell-free supernatant compositions of the present disclosure are cell-free supernatants of microbial cultures inoculated with one or more isolated microorganisms. Examples of these microorganisms include, but are not limited to, *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., and *Streptococcus* spp. Microbial cultures disclosed herein may comprise differing amounts and combinations of these and other microorganisms depending on the methods being performed by particular cell-free supernatant compositions.

Microorganisms that are useful in the present disclosure include, but are not limited to, one or more of the following:

| Microorganisms | |
| --- | --- |
| *Lactobacillus* | Hyperthermophile |
| *Lactobacillus fermentum* | *Methanopyrus kandleri* |
| *Streptococcus thermophiles* | *Methanobrevibacter smithii* |
| *Lactococcus diacetyllactis* | *Pyrococcus furiosus* |
| *Lactococcus lactis* | *Ferrglobus* |
| *Bifidobacterium bifidum* | *Ferrglobus placidus* |
| *Lactibacillus delbruecki* | Hydrothermal |
| Yeasts | *Pyrolobus fumarii* |
| *Candida Antarctica* | Thermophile |
| *Candida chauliode* | *Sulfolobus acidocaldarius* |
| *Candida corydalis* | *Sulfolobus islandicus* |
| *Candida albicans* | *Sulfolobus metallicus* |
| *Lodderomyces elongisporus* | *Sulfolobus shibatae* |
| *Candida dosseyi* | *Sulfolobus solfataricus* |
| *Candida blattae* | *Bacillus thuringiensis* |
| *Candida ascalaphidarum* | *Bacillus thuringiensis* Israelensis |

| Microorganisms | |
| --- | --- |
| *Candida membranifaciens* | *Pseudomonas* |
| *Candida oleophila* | *Pseudomonas alcaligenes* |
| *Streptomyces albus* | *Pseudomonas mendocina* |
| *Lachancea fermentati,* | *Pseudomonas pseudoalcaligenes* |
| *Lachancea thermotolerans* | *Pseudomonas resinovorans* |
| *Hanseniaspora vineae* | *Pseudomonas veronii* |
| *Saccharomycotina* | *Pseudomonas putida* |
| *Aspergillus* | *Pseudomonas stutzeri* |
| *Aspergillus oryzae* | *Pseudomonas fluorescens* |
| *Aspergillus niger* | *Pseudomonas chlororaphis* |
| *Aspergillus terreus* | *Pseudomonas aurantiaca* |
| *Aspergillus fischerianus* | *Pseudomonas aeruginosa,* |
| Green sulfur bacteria | White rot fungi |
| Purple sulfur bacteria | *Xanthomonas* |
| Chromatiaceae | *Acinetobacter* |
| Ectothiorhodospiraceae | *Rhodococcus* sp. |
| Halothiobacillaceae | *Arthrobacter* |
| *Halothiobacillus halophilus* | *Aureobasidium* sp. |
| *Halothiobacillus hydrothermalis* | *Alcaligeness* sp. |
| *Halothiobacillus kellyi* | *Leuconostoc* sp. |
| *Halothiobacillus neapolitanus* | *Sclerotium* sp. |
| Purple non sulfur bacteria | *Clostridium,* |
| *Rhodopseudomonas palustris* | *Zymomonas* |
| Salt or Ocean Bacterium | *Klebsiella* |
| *Halobacterium jilantaiense* | |
| *Halobacterium noricense* | |
| *Halobacterium salinarum* | |
| *Halobacterium piscisalsi* | |

Bacteria which may be useful in the present disclosure include, but are not limited to, one or more of the following:

| Bacteria | |
| --- | --- |
| *Bacillus alcalophilus* | *Bacillus lentus* |
| *Bacillus alvei* | *Bacillus licheniformis* |
| *Bacillus amyloliquefaciens* | *Bacillus megaterium* |
| *Bacillus aneurinolyticus* | *Bacillus mesentericus* |
| *Bacillus aquaemaris* | *Bacillus mucilaginosus* |
| *Bacillus brevis* | *Bacillus mycoides* |
| *Bacillus caldolyticus* | *Bacillus natto* |
| *Bacillus centrosporus* | *Bacillus pantothenticus* |
| *Bacillus cereus* | *Bacillus polymyxa* |
| *Bacillus circulans* | *Bacillus pseudoanthracis* |
| *Bacillus clausii* | *Bacillus pumilus* |
| *Bacillus coagulans* | *Bacillus schlegelii* |
| *Bacillus firmus* | *Bacillus sphaericus* |
| *Bacillus flavothermus* | *Bacillus sporothermodurans* |
| *Bacillus fusiformis* | *Bacillus stearothermophilus* |
| *Bacillus globigii* | *Bacillus subtilis* |
| *Bacillus halodurans* | *Bacillus thermoglucosidasius* |
| *Bacillus infernos* | *Bacillus thuringiensis* |
| *Bacillus larvae* | *Bacillus vulgatis* |
| *Bacillus laterosporus* | *Bacillus weihenstephanensis* |

In various aspects, the microorganisms cultured to produce the cell-free supernatant compositions of the present disclosure can be grown in large, industrial scale quantities. For example, and not to be limiting, a method for growing microorganisms in 1000 liter batches comprises media comprising 50 liters of non-sulphur agricultural molasses, 3.75 liters wheat bran, 3.75 liters kelp, 3.75 liters bentonite clay, 1.25 liters fish emulsion (a commercially available organic soil amendment, from Nutrivert, Dunham, Quebec non-pasteurized), 1.25 liters soy flour, 675 mg. commercially available sea salt, 50 liters of selected strains of microorganisms, up to 1000 liters non-chlorinated warm water to form a microbial culture. A method for growing the microorganisms can further comprise dissolving molasses in some of the warm water, adding the other ingredients listed above to the fill tank, keeping the temperature at 30° C., and, after the pH drops to about 3.7 within 5 days, stirring lightly once per day and monitoring pH, forming a microbial culture. The microbial culture can incubate for 2-8 weeks. After the time period determined for incubation, the microorganisms are separated from the liquid portion of the microbial culture, and the cell-free liquid remaining is a cell-free supernatant composition of the present disclosure. A cell-free supernatant composition may be bottled and stored, for example, in airtight containers, or out of sunlight, for example, at room temperature. Microbial cultures can be made as taught in U.S. patent application Ser. No. 13/979,419, which is herein incorporated in its entirety.

Microbial cultures of the present disclosure can be inoculated with a combination of microorganisms from several genera and/or species. These microorganisms grow and live in a cooperative fashion, in that some genera or species may provide by-products or synthesized compounds that are beneficial to other microorganisms in the combination. For example, microbial cultures can be inoculated with both aerobic microorganisms, which need oxygen for metabolic activities, and anaerobic microorganisms, which use other sources of energy such as sunlight or the presence of specific substrates.

A microbial culture can be inoculated with facultative microorganisms, for example, strains of *lactobacillus*, which modulate metabolic activities according to oxygen and/or nutrient concentrations in the environment.

All species of living organisms include individuals that vary genetically and biochemically from each other but are still within what is called the spectrum of normal variations within the species. These individual natural variations maybe the result of nondisruptive substitution or deletions in the gene sequence, variation in gene expression or RNA processing and/or variations in peptide synthesis and/or variation of cellular processing of intra cellular, membrane or secreted molecules. Microbial cultures can be inoculated with microorganisms that are within or without the normal variations of a species. Identification of such microorganisms may be detected by genetic, molecular biological methods known to those skilled in the art, and/or by methods of biochemical testing.

For example, microbial cultures of the present disclosure can be inoculated with microorganisms that were selected by isolating individual colonies of a particular microorganism. The colony members were characterized, for example, by testing enzyme levels present in the isolated microorganism and the activity with particular substrates in a panel of substrates, to establish an enzyme profile for the isolated microorganism. These substrates are representative of a cross-section of the biochemical pathways needed by the microorganisms in a composition of the present disclosure that is to be used in for general remediation purposes, such as the breakdown of organic matter of vegetable or animal matter, or for specific remediation purposes, such as the breakdown of particular chemicals.

In an aspect, a microbial culture comprises an *Aspergillus* spp. such as *Aspergillus oryzae*. In an aspect, the *Aspergillus* spp. is *Aspergillus oryzae*, referred to herein as IN-AO1, which was deposited with the ATCC Patent Depository under the Budapest Treaty, with the designation IN-AO1, on Sep. 4, 2014, under Account No. 200139, with the ATCC Patent Deposit Designation No. PTA-121551.

In an aspect, a microbial culture comprises a *Bacillus* spp. such as *Bacillus subtilis*. In an aspect, the *Bacillus* spp. is *Bacillus subtilis*, referred to herein as IN-BS1, which was deposited with the ATCC under the Budapest Treaty, on Jan. 12, 2011, under Account No. 200139, and given ATCC Patent Deposit Designation No. PTA12385.

In an aspect, a microbial culture comprises a *Rhodopseudomonas* spp. such as *Rhodopseudomonas palustris*. In an aspect, the *Rhodopseudomonas* spp. is *Rhodopseudomonas palustris*, referred to herein as IN-RP1, which was deposited with the ATCC under the Budapest Treaty, on Jan. 12, 2011, under Account No. 200139, and given ATCC Patent Deposit Designation No. PTA-12387.

In an aspect, a microbial culture comprises a *Candida* spp. such as *Candida utilis*. In an aspect, the *Candida* spp. is *Candida utilis*, referred to herein as IN-CU1, which was deposited with the ATCC Patent Depository under the Budapest Treaty, with the designation IN-CU1, on Sep. 4, 2014, under Account No. 200139, with the ATCC Patent Deposit Designation No. PTA-121550.

In an aspect, a microbial culture comprises a *Lactobacillus* spp. such as *Lactobacillus helveticus*, *Lactobacillus casei*, *Lactobaccillus rhamnosus*, or *Lactobacillus planterum*, or combinations thereof. In an aspect, the *Lactobacillus* spp. is *Lactobacillus helveticus*. In an aspect, the *Lactobacillus* spp. is *Lactobacillis helveticus*, referred to herein as IN-LH1, which was deposited with the ATCC under the Budapest Treaty, on Jan. 12, 2011, under Account No. 200139, and given ATCC Patent Deposit Designation No. PTA-12386. In an aspect, a microbial culture comprises a *Lactobacillus* spp. such as *Lactobacillus planterum*. In an aspect, the *Lactobacillus* spp. is *Lactobacillis plantarum*, referred to herein as IN-LP1, which was deposited with the ATCC Patent Depository under the Budapest Treaty, on Sep. 4, 2014, with the designation IN-LP1, under Account No. 200139, with the ATCC Patent Deposit Designation No. PTA-121555. In an aspect, a microbial culture comprises an *Lactobacillus* spp. such as *Lactobacillis rhamnosus*. In an aspect, the *Lactobacillus* spp. is *Lactobacillis rhamnosus*, referred to herein as IN-LR1, which was deposited with the ATCC Patent Depository under the Budapest Treaty, with the designation IN-LR1, on Sep. 4, 2014, under Account No. 200139, with the ATCC Patent Deposit Designation No. PTA-121554. In an aspect, a microbial culture comprises an *Lactobacillus* spp. such as *Lactobacillis lactis*. In an aspect, the *Lactobacillus* spp. is *Lactobacillis lactis*, referred to herein as IN-LL1, which was deposited with the ATCC Patent Depository under the Budapest Treaty, with the designation IN-LL1, on Sep. 4, 2014, under Account No. 200139, with the ATCC Patent Deposit Designation No. PTA-121552. In an aspect, a microbial culture comprises a *Lactobacillus* spp. such as *Lactobacillis casei*. In an aspect, the *Lactobacillus* spp. is *Lactobacillis casei*, referred to herein as IN-LC1, which was deposited with the ATCC Patent Depository under the Budapest Treaty, with the designation IN-LC1, on Sep. 4, 2014, under Account No. 200139, with the ATCC Patent Deposit Designation No. PTA-121549.

In an aspect, a microbial culture comprises a *Pseudomonas* spp. such as *Pseudomonas aeruginosa*. In an aspect, the *Pseudomonas* spp. is *Pseudomonas aeruginosa*.

In an aspect, a microbial culture comprises a *Rhodopseudomonas* spp. such as *Rhodopseudomonas palustris*. In an aspect, the *Rhodopseudomonas* spp. is *Rhodopseudomonas palustris*, referred to herein as IN-RP1, which was deposited with the ATCC under the Budapest Treaty, on Jan. 12, 2011, under Account No. 200139, and given ATCC Patent Deposit Designation No. PTA-12383. In an aspect, a microbial culture comprises a *Rhodopseudomonas* spp. such as *Rhodopseudomonas palustris*, referred to herein as IN-RP2, which was deposited with the ATCC Patent Depository under the Budapest Treaty, on Sep. 4, 2014, with the designation IN-RP2, under Account No. 200139, with the ATCC Patent Deposit Designation No. PTA-121553.

In an aspect, a microbial culture comprises a *Saccharomyces* spp. such as *Saccharomyces cerevisiae*. In an aspect, the *Saccharomyces* spp. is *Saccharomyces cerevisiae*, referred to herein as IN-SC1, which was deposited with the ATCC under the Budapest Treaty, on Jan. 12, 2011, under Account No. 200139, and given ATCC Patent Deposit Designation No. PTA-12384. In an aspect, a microbial culture comprises a *Saccharomyces* spp. such as *Saccharomyces lactis*.

A microbial culture may comprise a mixture of isolated microorganisms comprising *Aspergillus oryzae*, referred to herein as IN-AO1 (ATCC Patent Deposit Designation No. PTA-121551), *Bacillus subtilis*, referred to herein as IN-BS1 (ATCC Patent Deposit Designation No. PTA-12385), *Rhodopseudomonas palustris*, referred to herein as IN-RP1 (ATCC Patent Deposit Designation No. PTA-12387), *Candida utilis*, referred to herein as IN-CU1 (ATCC Patent Deposit Designation No. PTA-121550), *Lactobacillis casei*, referred to herein as IN-LC1 (ATCC Patent Deposit Designation No. PTA-121549), *Lactobacillis helveticus*, referred to herein as IN-LH1 (ATCC Patent Deposit Designation No. PTA-12386), *Lactobaccillus rhamnosus*, referred to herein as IN-LR1 (ATCC Patent Deposit Designation No. PTA-121554), *Lactobacillus plantarum*, referred to herein as IN-LP1 (ATCC Patent Deposit Designation No. PTA-121555), *Pseudomonas aeruginosa*, *Rhodopseudomonas palustris*, referred to herein as IN-RP1 (ATCC Patent Deposit Designation No. PTA-12387), *Rhodopseudomonas palustris*, referred to herein as IN-RP2 (ATCC Patent Deposit Designation No. PTA-121553), *Saccharomyces cerevisiae*, referred to herein as IN-SC1 (ATCC Patent Deposit Designation No. PTA-12384), and *Saccharomyces lactis*. Examples of isolated microorganisms inoculated in microbial cultures of the present disclosure include, but are not limited to, *Aspergillus oryzae, Rhodopseudomonas palustris, Candida utilis, Lactobacillis helveticus, Lactobacillus casei, Lactobaccillus rhamnosus, Lactobacillus plantarum, Pseudomonas aeruginosa, Rhodopseudomonas palustris, Saccharomyces cerevisiae*, and *Saccharomyces lactis*.

Microbial cultures may comprise differing amounts and combinations of these and other isolated microorganisms. Thus, in various aspects, a microbial culture is inoculated with of at least two of the following: *Aspergillus* spp., *Bacillus* spp., *Rhodopseudomonas* spp., *Candida* spp., *Lactobacillus* spp., *Pseudomonas* spp., *Saccharomyces* spp., or *Streptococcus* spp. In an aspect, a microbial culture is inoculated with *Aspergillus oryzae, Bacillus subtilis, Lactobacillus helveticus, Lactobacillus casei, Rhodopseudomonas palustris*, and *Saccharomyces cervisiase*. In an aspect, a microbial culture is inoculated with a mixed culture, IN-M1 (ATCC Patent Deposit Designation No. PTA-12383). The deposited mixed culture, IN-M1, consists of the strains IN-LH1, IN-BS1, IN-SC1, IN-RP1; and *Lactobacillus casei* and *Aspergillus oryzae*, using the designations used hereinbefore. In an aspect, a microbial culture is inoculated with *Aspergillus oryzae, Bacillus subtilis, Candida utilis, Lactobacillus casei, Lactobacillus helveticus, Lactobacillus plantarum, Lactobacillus rhamnosus, Lactococcus lactis, Rhodopseudomonas palustris*, and *Saccharomyces cervisiase*. In an aspect, a microbial culture is inoculated with and comprises a mixed culture, referred to herein as IN-M2, which was deposited with the ATCC Patent Depository under the Budapest Treaty, on Sep. 4, 2014, with the designation IN-M2, under Account No. 200139, with the ATCC Patent Deposit Designation No. PTA-121556. The deposited mixed culture, IN-M2, consists of the strains IN-LC1, IN-LH1, IN-LP1, IN-LR1, IN-LL1, IN-BS1, IN-AO1, IN-SC1, IN-CU1, IN-RP1, and IN-RP2, using the designations used hereinbefore. Any of the disclosed microbial cultures can be the microbial culture source for a cell-free supernatant composition of the present disclosure. Cell-free supernatant compositions of the present disclosure are useful in the methods taught herein.

Selection Criteria

One or more selection criteria enable the formulation of the microorganisms for a microbial culture of microorganisms to provide a standardized ecosystem and provide cell-free supernatant compositions to carry out particular reactions. For example, microorganisms that provide enzymes may be tested for enzyme activity levels for substrates, enzyme profile testing.

Methods for selection of a microorganism for a microbial culture comprise testing for enzyme profile activity, growth characteristics under differing conditions such as oxygen or temperature, growth in particular media conditions, such as nitrates, carbohydrates, minerals or particular contaminants, and characteristic responses for particular microorganisms, such as the ability to form spores. These tests allow for the characterization of a particular microorganism, and the formation of a useful microbial culture. Thus one testing criteria for microorganisms for microbial cultures is the interaction of the various microbial species together. A microorganism may meet the enzyme profile tests and other criteria but it may not be able to grow well when added to a consortium of microorganisms, and thus that microorganism would not be selected as a component of a microbial culture.

Enzyme Profile Test

An example of an enzyme profile test comprises providing substrates and noting where there is high activity, +3 or greater, and where there is little to no activity, +2 and below. For example, a *lactobacillus* was tested and had a +5 enzyme level for alkaline phosphatase and a 0 for lipase. Such a *lactoballicus* may be admixed in a microbial culture with another microorganism where the lipase production is +4 or +5. Both enzyme activities are desired in microbial cultures where reactions are needed to breakdown organic matter, for example. Using microorganisms with differing strengths allows for cooperative, completion of metabolic pathways in order not to have incomplete biochemical pathways which leave, either intermediary compounds that are not bioavailable to the environment, or are not available to other microbial species as nutrition or prebiotics, or that do not provide active compounds/enzymes targeting specific pollutants. Incomplete biochemical pathways also do not provide molecules involved in the production or activation of nutritional elements for different species in the composition or in the inoculated environment; hormones, growth factors, antibactericides, etc., with paracrine influence on the growth and regeneration of the damaged environment. Another detrimental effect of incomplete biochemical pathways is the production of intermediary compounds that are ether toxic and/or odorous, like hydrogen sulfide.

For example, bacterial strains isolated from *bacillus* species were characterized by enzyme profiles comprising ability to hydrolyze fibrous matter (cellulose and hemi cellulose), proteins and fat; and ability to complete the degradation of numerous intermediary molecules and cells that accumulate during the metabolic processes. These characteristics are useful for degradation of organic matter and reduction or prevention of odors and other gas emissions. On a scale of 0 to 5, by trained eyes in assessing the color change in the enzyme reaction, the ranking +4-to +5 are generally optimal, though lower responses by particular organisms may be acceptable.

The enzyme tests are commercially available and the testing procedures for microorganisms and methods for determining activity levels are well known in the art. Other characteristics include, for example, screening *Saccharomyces cerevisiae* for fermentation enzymes and *bacillus* species with known enzyme profiles. Testing microorganisms to determine which strains have high enzyme activity of certain enzymes which take part in proven fermentation pathways allows for identification of microorganisms that will perform well in microbial cultures. Isolation of individual colonies and the enzyme profile testing of these allows for the isolation of strong expressers of the enzymes. Other functional screening tests can be used to characterize microorganisms in a microbial culture.

Formation of Spores

A selection criterion for microorganisms may be the formation or lack of formation of spores. For example, strains may be selected based on their response when moved from a starvation media to a nutrient rich media. Strains that show aggressive growth when transferred from a starvation medium to nutrient rich medium, and that also showed decreased sporulation, or a lower amount of spore formation in the starved cultures, may be optimal. A species that survive adverse conditions by forming spores may not be optimal for microbial cultures.

Temperature

A selection criterion for microorganisms to be inoculated in a microbial culture may be growth of the microorganism at different temperatures. For example, one or more *Bacillus* strains were selected based on the ability to grow at different temperatures in aerobic conditions Growth curves numbers of bacteria by OD and pH over time at different temperatures from 15 C-40° C. were used as the criteria for selection. Selected strains may be capable of growth in the presence of nitrates, capable of growth under anaerobic conditions or have other selected characteristics. For example, a *Bacillus* useful in a microbial culture is characterized by the following: a +5 level of cellulase, a +2 to +3 level of proteinase, at least a +4 of fatase, grows in an 8% nitrate media, grows in a range of temperatures from 30° C. to 40° C., and does not form spores.

*B. subtilis* will grow anaerobically, either by using nitrate or nitrite as a terminal electron acceptor, or by fermentation. A two-component signal transduction system is an early stage in the regulatory pathway governing anaerobic respiration. One of the roles of ResD and ResE in anaerobic gene regulation is induction of fnr transcription upon oxygen limitation. FNR is a transcriptional activator for anaerobically induced genes, including those for respiratory nitrate reductase, narGHJI. *B. subtilis* has two distinct nitrate reductases, one for the assimilation of nitrate nitrogen and the other for nitrate respiration. In contrast, one nitrite reductase functions both in nitrite nitrogen assimilation and nitrite respiration. Unlike many anaerobes, which use pyruvate formate lyase, *B. subtilis* can carry out fermentation in the absence of external electron acceptors wherein pyruvate dehydrogenase is utilized to metabolize pyruvate. *B. subtilis* generally grows at 25-37° C., gene expression observed at 15° C.-40° C.

Oxygen Metabolism and Nutrient Concentrations

Selection criteria of oxygen metabolism and nutrient concentrations may be used to characterize microorganisms used to inoculate the culture used to prepare the cell-free composition of the present disclosure. For example, *Lactobacillus* strains may be selected based on the ability to modulate metabolic activity depending on the oxygen concentration or nutrient concentration in the growth media, and by extension, what activities the lactobacilli will have in a particular environment when used in a composition of the present disclosure. For example, *Lactobacillus* convert lactose and other sugars to lactic acid. The production of lactic acid makes the *lactobacillus* environment acidic, which inhibits the growth of some harmful bacteria. The majority of acidifying flora in the culture generally control the pH of the environment. This characteristic allows for methods of the present disclosure, when providing for biostimulation or bioprotection, to provide a low pH composition. Such compositions may have a greater than two years shelf life. In certain *lactobacillus* strains, for example, *L. plantarum*, the secretion of lactic acid is down regulated when the pH is below a pH 3 and up regulated when the pH is too high, whereas pH 4-5 is optimal.

Lactobacilli strains used in the inoculation of a culture used in the preparation of cell-free composition of the present disclosure may be selected on the basis of their ability to help provide the components in the formulation that provide stability for a prolonged shelf-life at room temperature. For example, if a composition of the present disclosure is stored in a sealed or closed container at room temperature, the biological activity of that composition is measured by opening the container and reactivation of the composition by known microorganism steps of dilution and the addition of molasses (a nutrient source) and incubation at 30-37° C. This is monitored by observing the pH going down to 3.7 and below in 5-7 days. A sealed container of a composition of the present disclosure, stored at room temperature, has a shelf life of longer than 2 months, longer than 4 months, longer than 6 months, longer than 8 months, longer than 10 months, longer than 12 months, longer than 18 months, longer than 24 months, longer than 30 months, or longer than 36 months.

Yeasts and Fungi

Beneficial yeasts, fungi and aspergillum provide to the cell-free compositions of the present disclosure components such as enzymes, proteins, fatty acids, and other small molecule components that are actively secreted from cells during culture or are from lysed cells. Though not wishing to be bound by any particular theory, it is believed that such secreted components provide a direct biostimulatory effect by directly stimulating the growth of the subject plant and/or an indirect biostimulatory effect, for example, by increasing the ability of the various microbial species present in the plant growth environment to colonize and other bioactivity. In a composition of the present disclosure, yeasts, fungi and aspergillum provide components such as enzymes, proteins, fatty acids, and other small molecule components to provide biostimulation, and cell debris to maintain the anaerobic photosynthetic bacteria present in the environment. A characteristic for yeast or fungus that may be useful in particular uses of compositions of the present disclosure is that they are nonpathogenic and nontoxic to humans and animals, and that they secrete components found in the cell-free composition that are nonpathogenic and nontoxic to humans and animals.

Methods of Enhancing Plant Growth

In an aspect, disclosed herein are methods of enhancing plant growth comprising providing a disclosed cell-free supernatant composition to a seed, to a plant, or to a plant at a particular growth stage, or combinations thereof, thereby enhancing plant growth. A composition may comprise a cell-free supernatant of a microbial culture inoculated with an isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof. In an aspect the microbial culture comprises IN-M1. In an aspect, the microbial culture comprises IN-M2.

A method of enhancing plant growth comprising providing or treating a disclosed cell-free supernatant composition to a seed, to a plant, or to a plant at a particular growth stage, or combinations thereof, thereby enhancing plant growth in the treated plant compared to untreated plant, wherein providing the cell-free supernatant composition comprises applying the cell-free supernatant to the seeds of plants, or wherein providing the cell-free supernatant composition comprises applying the cell-free supernatant to the roots of plants, wherein providing the cell-free supernatant composition comprises applying the cell-free supernatant to the leaves or stalks of plants. The method may comprise plants wherein the plant is grown under hydroponic conditions or wherein the plant is grown under aeroponic conditions or combined aeroponic and hydroponic conditions, or wherein the plant is grown in a greenhouse, or wherein the plant is grown in a field.

A method of enhancing plant growth comprising providing or treating a disclosed cell-free supernatant composition to a seed, to a plant, or to a plant at a particular growth stage, or combinations thereof, thereby enhancing plant growth in the treated plant compared to untreated plant, wherein enhancing plant growth is stimulation of meristem differentiation, or wherein enhancing plant growth is an increased germination rate of seeds, wherein the increased germination rate is 10%, 15%, or 20% greater than that of substantially similar seeds that were not provided the cell-free supernatant composition, wherein the germination rate is determined over a period from 0-70 hours under induced abiotic stress laboratory conditions in a cell-free broth. A method of enhancing plant growth comprising providing or treating a disclosed cell-free supernatant composition to a seed, to a plant, or to a plant at a particular growth stage, or combinations thereof, thereby enhancing plant growth in the treated plant compared to untreated plant, wherein enhancing plant growth is an increase in leaf area or dry biomass, wherein the increase in leaf area is 5%, 6%, 7%, 8%, 9%, 10%, 11%, 12%, 13%, 14%, 15%, 16%, 17%, 18%, 19%, 20%, 22%, 24%, 26%, 28%, or 30% compared to leaf area of substantially similar plants that were not provided the cell-free supernatant composition, or wherein the increase in dry biomass is 5%, 6%, 7%, 8%, 9%, 10%, 11%, 12%, 13%, 14%, 15%, 16%, 17%, 18%, 19%, 20%, 22%, 24%, 26%, 28%, or 30% compared to dry biomass of substantially similar plants that were not provided the cell-free supernatant composition. A method of enhancing plant growth comprising providing or treating a disclosed cell-free supernatant composition to a seed, to a plant, or to a plant at a particular growth stage, or combinations thereof, thereby enhancing plant growth in the treated plant compared to untreated plant, wherein enhancing plant growth is an increase in fruit production of plants provided the cell-free supernatant compared to fruit production of substantially similar plants that were not provided the cell-free supernatant composition. A method of enhancing plant growth comprising providing or treating a disclosed cell-free supernatant composition to a seed, to a plant, or to a plant at a particular growth stage, or combinations thereof, thereby enhancing plant growth in the treated plant compared to untreated plant, wherein enhancing plant growth is an increase in productive lifespan of plants provided the cell-free supernatant compared to productive lifespan of substantially similar plants that were not provided the cell-free supernatant composition. A method of enhancing plant growth comprising providing or treating a disclosed cell-free supernatant composition to a seed, to a plant, or to a plant at a particular growth stage, or combinations thereof, thereby enhancing plant growth in the treated plant compared to untreated plant, wherein enhancing plant growth is an increase in production period of plants provided the cell-free supernatant compared to production period of substantially similar plants that were not provided the cell-free supernatant composition.

A method of using a composition of the present disclosure comprises a method of affecting, enhancing, modulating, stimulating or aiding plant growth, comprising, providing a cell-free supernatant composition to a site where plants are grown, to a plant or to a plant at a particular growth stage, or combinations thereof, so that the growth of the treated plant is increased, enhanced or stimulated compared to a similar untreated plant. A method may comprise applying the cell-free supernatant composition to the seeds of plants. A method may comprise applying the cell-free supernatant composition to the roots of plants, either before planting or after planting the plants in a growth medium. A method may comprise applying the cell-free supernatant composition to the leaves and/or stalks of plants. A method may comprise enhancing seed germination, by applying an effective amount of a cell-free supernatant composition disclosed herein to the plant, to a plant seed, to the soil (or growth medium) in which the plant is located, or in water or other liquids provided to the plant, wherein the seed germination is enhanced, for example, by faster germination or better growth, compared to untreated seeds. A method may comprise enhancing root production by applying an effective amount of a cell-free supernatant composition disclosed herein to the plant, to a plant seed, to the soil (or growth medium) in which the plant is located, or in water or other liquids provided to the plant, wherein the treated plant has enhanced root production compared to untreated plants. A method may comprise increasing the per plant yield of treated plants compared to untreated plants, by applying an effective amount of a cell-free supernatant composition disclosed herein to the plant, to a plant seed, to the soil (or growth medium) in which the plant is located, or in water or other liquids provided to the plant. A method may comprise increasing the biomass of treated plants compared to untreated plants, by applying an effective amount of a cell-free supernatant composition disclosed herein to the plant, to a plant seed, to the soil (or growth medium) in which the plant is located, or in water or other liquids provided to the plant. A method may comprise increasing the fruit production of the treated plants compared to untreated plants, by applying an effective amount of a cell-free supernatant composition disclosed herein to the plant, to a plant seed, to the soil (or growth medium) in which the plant is located, or in water or other liquids provided to the plant. A method may comprise increasing the production period of the treated plants compared to untreated plants, by applying an effective amount of a cell-free supernatant composition disclosed herein to the plant, to a plant seed, to the soil (or growth medium) in which the plant is located, or in water or other liquids provided to the plant. A method may comprise increasing the productive lifespan of the treated plants compared to untreated plants, by applying an effective amount of a cell-free supernatant composition disclosed herein to the plant, to a plant seed, to the soil (or growth medium) in which the plant is located, or in water or other liquids provided to the plant. The method may comprise using the method with plants grown under hydroponic conditions. The method may comprise using the method with plants grown in a greenhouse. A method may comprise using the method with plants grown in a field or outside. A method may comprise using the method with plants grown in aeroponic conditions, or combined hydroponic and aeroponic conditions. A method may comprise using the method with vertical farming.

Use of a cell-free supernatant composition made from a microbial culture inoculated with an isolated microorganism, such as one or more mixed cultures, for example, IN-M1 or IN-M2, or compositions comprising one or more of IN-AO1, IN-BS1, IN-RP1, IN-RP2, IN-LH1, IN-LC1, IN-LL1, IN-LP1, IN-LR1, and IN-SC1, in combination or individually, and/or with other microorganisms have shown stimulation of plant growth for plants grown in organic material with mychorrhyzal fungi; algae blooms in nutrient solutions were suppressed; suppression of common plant infections; and suppression of algae growth on turf grasses of golf greens and mold on leaves of growing plants.

Compositions and methods of the present disclosure comprise enhancement of seed germination. Thus, in various aspects, providing a cell-free supernatant composition made from a microbial culture inoculated with an isolated microorganism, such as one or more mixed cultures, for example, IN-M1 or IN-M2, or compositions comprising one or more of IN-AO1, IN-BS1, IN-RP1, IN-RP2, IN-LH1, IN-LC1, IN-LL1, IN-LP1, IN-LR1, and IN-SC1, in combination or individually, and/or with other microorganisms, to seeds, for example, soybean seed, may increase seed germination. In various aspects, seed germination in turf grasses, such as, for example, those that are used in golf courses, may be enhanced by treating the turf grass seeds with a cell-free supernatant composition made from a microbial culture inoculated with an isolated microorganism, such as one or more mixed cultures, for example, IN-M1, or IN-M2 or compositions comprising IN-LH1, IN-BS1, IN-SC1, and/or IN-RP1, in combination or individually, and/or with other microorganisms.

In an aspect, providing the cell-free supernatant composition comprises applying the cell-free supernatant to the seeds of plants. In an aspect, providing the cell-free supernatant composition comprises applying the cell-free supernatant to the roots of plants. In an aspect, providing the cell-free supernatant composition comprises applying the cell-free supernatant to the leaves or stalks of plants. In an aspect, providing a cell-free supernatant composition comprises adding a cell-free supernatant composition to the water or other liquid composition that is provided to a plant. For example, cell-free supernatant composition may be added to an irrigation system so that the cell-free supernatant composition is provided when the irrigation water is provided.

In an aspect, seeds are coated with one or more compositions described herein. In one aspect, seeds may be treated with composition(s) described herein in several ways, for example, via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed. Systems and apparatus for performing these processes are commercially available from numerous suppliers, e.g., Bayer CropScience (Gustafson).

In another aspect, seedtreatment comprises coating seeds. One such process involves coating the inside wall of a round container with one or more composition(s) described herein, adding seeds, then rotating the container to cause the seeds to contact the wall and the composition(s), a process known in the art as "container coating". Seeds can be coated by combinations of coating methods. Soaking seeds typically comprises using liquid forms of the compositions described. For example, seeds can be soaked for about 1 minute to about 24 hours (e.g., for at least 1 min, 5 min, 10 min, 20 min, 40 min, 80 min, 3 hr, 6 hr, 12 hr, 24 hr).

In an aspect, a plant to be treated is grown under hydroponic conditions. In an aspect, a plant to be treated is grown under aeroponic conditions or combined aeroponic and hydroponic conditions. In an aspect, a plant to be treated is grown in a greenhouse. In an aspect, the plant to be treated is grown in a field.

In an aspect, enhancing plant growth comprises stimulation of meristem differentiation, compared to an untreated similar plant. In an aspect, enhancing plant growth comprises an increased germination rate of treated seeds compared to untreated seeds.

In an aspect, the increased germination rate of a seed treated with a cell-free supernatant composition is 5% greater than that of substantially similar seeds that were not provided the cell-free supernatant composition. In an aspect, the increased germination rate of a seed treated with a cell-free supernatant composition is 10% greater than that of substantially similar seeds that were not provided the cell-free supernatant composition. In an aspect, the increased germination rate of a seed treated with a cell-free supernatant composition is 15% greater than that of substantially similar seeds that were not provided the cell-free supernatant composition. In an aspect, the increased germination rate of a seed treated with a cell-free supernatant composition is 20% greater than that of substantially similar seeds that were not provided the cell-free supernatant composition. In an aspect, the increased germination rate of a seed treated with a cell-free supernatant composition is 25% greater than that of substantially similar seeds that were not provided the cell-free supernatant composition. In an aspect, the increased germination rate of a seed treated with a cell-free supernatant composition is greater than 10%, 15%, 20%, 30%, 40%, 50%, or higher than that of substantially similar seeds that were not provided the cell-free supernatant composition.

In an aspect, the germination rate is determined over a period from 0-70 hours under induced abiotic stress laboratory conditions in a cell-free broth.

In an aspect, enhancing plant growth is an increase in leaf area or dry biomass.

In an aspect, enhancing plant growth is an increase in leaf area. In an aspect, the increase in leaf area of a plant treated with a cell-free supernatant composition is 5% compared to leaf area of substantially similar plants that were not provided the cell-free supernatant composition. In an aspect, the increase in leaf area of a plant treated with a cell-free supernatant composition is 6% compared to leaf area of substantially similar plants that were not provided the cell-free supernatant composition. In an aspect, the increase in leaf area of a plant treated with a cell-free supernatant composition is 7% compared to leaf area of substantially similar plants that were not provided the cell-free supernatant composition. In an aspect, the increase in leaf area of a plant treated with a cell-free supernatant composition is 8% compared to leaf area of substantially similar plants that were not provided the cell-free supernatant composition. In an aspect, the increase in leaf area of a plant treated with a cell-free supernatant composition is 9% compared to leaf area of substantially similar plants that were not provided the cell-free supernatant composition. In an aspect, the increase in leaf area is 10% compared to leaf area of substantially similar plants that were not provided the cell-free supernatant composition. In an aspect, the increase in leaf area of a plant treated with a cell-free supernatant composition is 11% compared to leaf area of substantially similar plants that were not provided the cell-free supernatant composition. In an aspect, the increase in leaf area of a plant treated with a cell-free supernatant composition is 12% compared to leaf area of substantially similar plants that were not provided the cell-free supernatant composition. In an aspect, the increase in leaf area of a plant treated with a cell-free supernatant composition is 13% compared to leaf area of substantially similar plants that were not provided the cell-free supernatant composition. In an aspect, the increase in leaf area of a plant treated with a cell-free supernatant composition is 14% compared to leaf area of substantially similar plants that were not provided the cell-free supernatant composition. In an aspect, the increase in leaf area of a plant treated with a cell-free supernatant composition is 15% compared to leaf area of substantially similar plants that were not provided the cell-free supernatant composition. In an aspect, the increase in leaf area of a plant treated with a cell-free supernatant composition is 16% compared to leaf area of substantially similar plants that were not provided the cell-free supernatant composition. In an aspect, the increase in leaf area of a plant treated with a cell-free supernatant composition is 17% compared to leaf area of substantially similar plants that were not provided the cell-free supernatant composition. In an aspect, the increase in leaf area of a plant treated with a cell-free supernatant composition is 18% compared to leaf area of substantially similar plants that were not provided the cell-free supernatant composition. In an aspect, the increase in leaf area of a plant treated with a cell-free supernatant composition is 19% compared to leaf area of substantially similar plants that were not provided the cell-free supernatant composition. In an aspect, the increase in leaf area of a plant treated with a cell-free supernatant composition is 20% compared to leaf area of substantially similar plants that were not provided the cell-free supernatant composition. In an aspect, the increase in leaf area of a plant treated with a cell-free supernatant composition is 22% compared to leaf area of substantially similar plants that were not provided the cell-free supernatant composition. In an aspect, the increase in leaf area of a plant treated with a cell-free supernatant composition is 24% compared to leaf area of substantially similar plants that were not provided the cell-free supernatant composition. In an aspect, the increase in leaf area of a plant treated with a cell-free supernatant composition is 26% compared to leaf area of substantially similar plants that were not provided the cell-free supernatant composition. In an aspect, the increase in leaf area of a plant treated with a cell-free supernatant composition is 28% compared to leaf area of substantially similar plants that were not provided the cell-free supernatant composition. In an aspect, the increase in leaf area of a plant treated with a cell-free supernatant composition is 30% compared to leaf area of substantially similar plants that were not provided the cell-free supernatant composition. In an aspect, the increase in leaf area of a plant treated with a cell-free supernatant composition is 5%, 6%, 7%, 8%, 9%, 10%, 11%, 12%, 13%, 14%, 15%, 16%, 17%, 18%, 19%, 20%, 22%, 24%, 26%, 28%, 30%, 40%, 50% or more compared to leaf area of substantially similar plants that were not provided a cell-free supernatant composition.

In an aspect, enhancing plant growth is an increase in dry biomass. In an aspect, the increase in dry biomass of a plant treated with a cell-free supernatant composition is 5% compared to dry biomass of substantially similar plants that were not provided the cell-free supernatant composition. In an aspect, the increase in dry biomass of a plant treated with a cell-free supernatant composition is 6% compared to dry biomass of substantially similar plants that were not provided the cell-free supernatant composition. In an aspect, the increase in dry biomass of a plant treated with a cell-free supernatant composition is 7% compared to dry biomass of substantially similar plants that were not provided the cell-free supernatant composition. In an aspect, the increase in dry biomass of a plant treated with a cell-free supernatant composition is 8% compared to dry biomass of substantially similar plants that were not provided the cell-free supernatant composition. In an aspect, the increase in dry biomass of a plant treated with a cell-free supernatant composition is 9% compared to dry biomass of substantially similar plants that were not provided the cell-free supernatant composition. In an aspect, the increase in dry biomass of a plant treated with a cell-free supernatant composition is 10% compared to dry biomass of substantially similar plants that were not provided the cell-free supernatant composition. In an aspect, the increase in dry biomass of a plant treated with a cell-free supernatant composition is 11% compared to dry biomass of substantially similar plants that were not provided the cell-free supernatant composition. In an aspect, the increase in dry biomass of a plant treated with a cell-free supernatant composition is 12% compared to dry biomass of substantially similar plants that were not provided the cell-free supernatant composition. In an aspect, the increase in dry biomass of a plant treated with a cell-free supernatant composition is 13% compared to dry biomass of substantially similar plants that were not provided the cell-free supernatant composition. In an aspect, the increase in dry biomass of a plant treated with a cell-free supernatant composition is 14% compared to dry biomass of substantially similar plants that were not provided the cell-free supernatant composition. In an aspect, the increase in dry biomass of a plant treated with a cell-free supernatant composition is 15% compared to dry biomass of substantially similar plants that were not provided the cell-free supernatant composition. In an aspect, the increase in dry biomass of a plant treated with a cell-free supernatant composition is 16% compared to dry biomass of substantially similar plants that were not provided the cell-free supernatant composition. In an aspect, the increase in dry biomass of a plant treated with a cell-free supernatant composition is 17% compared to dry biomass of substantially similar plants that were not provided the cell-free supernatant composition. In an aspect, the increase in dry biomass of a plant treated with a cell-free supernatant composition is 18% compared to dry biomass of substantially similar plants that were not provided the cell-free supernatant composition. In an aspect, the increase in dry biomass of a plant treated with a cell-free supernatant composition is 19% compared to dry biomass of substantially similar plants that were not provided the cell-free supernatant composition. In an aspect, the increase in dry biomass of a plant treated with a cell-free supernatant composition is 20% compared to dry biomass of substantially similar plants that were not provided the cell-free supernatant composition. In an aspect, the increase in dry biomass of a plant treated with a cell-free supernatant composition is 22% compared to dry biomass of substantially similar plants that were not provided the cell-free supernatant composition. In an aspect, the increase in dry biomass of a plant treated with a cell-free supernatant composition is 24% compared to dry biomass of substantially similar plants that were not provided the cell-free supernatant composition. In an aspect, the increase in dry biomass of a plant treated with a cell-free supernatant composition is 26% compared to dry biomass of substantially similar plants that were not provided the cell-free supernatant composition. In an aspect, the increase in dry biomass of a plant treated with a cell-free supernatant composition is 28% compared to dry biomass of substantially similar plants that were not provided the cell-free supernatant composition. In an aspect, the increase in dry biomass of a plant treated with a cell-free supernatant composition is 30% compared to dry biomass of substantially similar plants that were not provided the cell-free supernatant composition. In an aspect, the increase in dry biomass of a plant treated with a cell-free supernatant composition is 5%, 6%, 7%, 8%, 9%, 10%, 11%, 12%, 13%, 14%, 15%, 16%, 17%, 18%, 19%, 20%, 22%, 24%, 26%, 28%, 30%, 40%, 50% or more compared to dry biomass of substantially similar plants that were not provided the cell-free supernatant composition.

In an aspect, enhancing plant growth is an increase in fruit production of plants provided a cell-free supernatant compared to fruit production of substantially similar plants that were not provided the cell-free supernatant composition.

In an aspect, enhancing plant growth is an increase in productive lifespan of plants provided a cell-free supernatant compared to productive lifespan of substantially similar plants that were not provided the cell-free supernatant composition.

In an aspect, enhancing plant growth is an increase in production period of plants provided a cell-free supernatant compared to production period of substantially similar plants that were not provided the cell-free supernatant composition.

Methods of Making an Article

In an aspect, disclosed herein are methods of making an article comprising a cell-free supernatant comprising providing the disclosed cell-free supernatant composition to a surface of an article. A method may comprise steps of applying the cell-free supernatant composition to an article and then the combined cell-free supernatant composition and article is dried so as to attach the cell-free supernatant composition to the surfaces of the article. A method may comprise steps where one or more surfaces of an article is treated to aid in attachment of the cell-free supernatant composition. A method may comprise adding one or more components to the cell-free supernatant composition to aid in attachment of the cell-free supernatant composition to the surface or surfaces of the article. A method may comprise adding one or more components to both the cell-free supernatant composition and one or more surfaces of an article to aid in attachment of the cell-free supernatant composition to the surface. Such components may be any material, compound or molecule that aids in the attachment of the cell-free supernatant composition to the surface or the article. For example, components such glues, starches, natural materials, polymeric materials and materials that are known for attaching to surfaces or articles may be used. A method may comprise surfaces or articles wherein the surface or article is a glass bead, inert materials, woven materials, nonwoven materials, natural materials such as plant material, coco mats, silica beads, polymeric materials, plant container, container, filter structures, porous inert particles, or zeolites. Articles made with attached cell-free supernatant compositions of the present disclosure are contemplated by the disclosure.

A method of making an article comprising a cell-free supernatant comprising providing a disclosed cell-free supernatant composition to a surface of an article. The method may further comprise drying the article is dried after providing the cell-free supernatant. The method may further comprise a step of treating the surface of the article prior to providing the cell-free supernatant to the surface of the article. The method may further comprise the step of treating the surface of the article after providing the cell-free supernatant to the surface of the article. The method of providing an article comprising a cell-free supernatant composition wherein providing the cell-free supernatant composition is spraying, or wherein providing the cell-free supernatant composition is immersion of the article in vessel containing the cell-free supernatant composition. The method may further comprise adding one or more surface-attachment aids to the cell-free supernatant composition, wherein the surface-attachment aid facilitates the attachment one or more components of the cell-free supernatant to the surface of the article, or wherein the surface-attachment aid is capable of linking the one or more components in the cell-free supernatant to the surface of the article, or wherein the surface-attachment aid is a chemical compound, or wherein the chemical compound provides a reversible chemical linkage between the one or more components of the cell-free supernatant to the surface of the article, or wherein the chemical compound provides an irreversible chemical linkage between the one or more components of the cell-free supernatant to the surface of the article, or wherein the surface-attachment aid is a nucleic acid, a protein, an oligonucleotide, or a peptide. The method of providing an article comprising a cell-free supernatant composition wherein the article is a biochar, a bead, a filter, a container, a nanoparticle, a microparticle, a mat, a screen, a powder, a particulate, or a cloth, a woven material, a non-woven material, a plant material, a mat, a container, a polymeric material, a porous material, a non-porous material, or a zeolite.

In an aspect, a method comprises drying the article coated with the cell-free supernatant composition after providing the cell-free supernatant composition to the article.

In an aspect, a method comprises the step of treating one or more surfaces of an article prior to providing the cell-free supernatant composition to the one or more surfaces of the article.

In an aspect, a method comprises the step of treating one or more surfaces of the article after providing the cell-free supernatant composition to the one or more surfaces of the article.

In an aspect, providing the cell-free supernatant composition comprises spraying the article with the cell-free supernatant composition. In an aspect, providing the cell-free supernatant composition to the article comprises immersion of the article in a vessel containing a cell-free supernatant composition.

In an aspect, a method comprises adding one or more surface-attachment aids to the cell-free supernatant composition, wherein the surface-attachment aid facilitates the attachment of one or more components of the cell-free supernatant to one or more surfaces of the article. In an aspect, the surface-attachment aid is capable of linking the one or more components in the cell-free supernatant to the one or more surfaces of the article. In an aspect, the surface-attachment aid is a chemical compound. In an aspect, the chemical compound provides a reversible chemical linkage between the one or more components of the cell-free supernatant composition to the one or more surfaces of the article. In an aspect, the chemical compound provides an irreversible chemical linkage between the one or more components of the cell-free supernatant composition to the one or more surfaces of the article. In an aspect, the surface-attachment aid is a nucleic acid, a protein, an oligonucleotide, or a peptide.

In an aspect, the article is a biochar, a bead, a filter, a container, a nanoparticle, a microparticle, a mat, a screen, a powder, a particulate, or a cloth. In an aspect, an article is a woven material, a non-woven material, a plant material, a mat, a container, a polymeric material, a porous material, a non-porous material, or a zeolite.

Methods of Preparing a Cell-Free Supernatant Composition

In an aspect, disclosed herein are methods of preparing a cell-free supernatant composition comprising the steps of: (a) forming a microbial culture disclosed herein by inoculating a culture medium, also referred to as a fermentation broth, with an isolated microorganism, wherein the microorganism comprises microorganisms disclosed herein, such as IN-M1, In-M2, deposited strains disclosed herein, *Aspergillus* spp., *Bacillus* spp., *Rhodopseudomonas* spp., *Candida* spp., *Lactobacillus* spp., *Pseudomonas* spp., *Saccharomyces* spp., or *Streptococcus* spp., or combinations thereof, to form a microbial culture; (b) incubating the microbial culture for at least five hours; and (c) centrifuging the microbial culture after step (b) for at least 10 minutes at a centrifugal force of 10,000×g; thereby separating the centrifuged material comprising microorganisms from the liquid of the microbial culture and providing the cell-free supernatant composition. A method may comprise measuring characteristics of the microbial culture. Measuring characteristics of the microbial culture may comprise measuring the predation of one or more selected microorganism by one or more other selected microorganisms, measuring factors or proteins released or made by one or more microorganisms, pH changes, or extracellular enzymes excreted by one or more selected microorganisms and its effects on one or more other selected microorganism, measuring the number of cells per mL of one or more selected microorganism in the microbial culture, determining growth rate for one or more selected microorganisms, or combinations of characteristics and measurements. A method may comprise using the measured characteristics of the microbial culture to determine if one or more microorganisms are to be removed from the microbial culture or if one or more microorganisms are to be added to the microbial culture. A method may comprise wherein when one or more microorganisms are to be removed from the microbial culture, the method may comprise killing the microbial culture. A method may comprise steps wherein when one or more microorganisms are to be added to the microbial culture, the method may comprise adding one or more desired isolated microorganisms to the microbial culture, and growing the microbial culture to a predetermined cellular concentration to produce a microbial culture, and optionally, packaging all or a portion of the microbial culture. A method may comprise repeating the steps of a method one or more times. A method may comprise growing the cells of the microbial culture to a particular concentration to form an individual microbial culture. A method may comprise making one or more microbial cultures and f) combining the individual microbial culture to form a microbial culture. A method may comprise growing a microbial culture to a particular concentration; and packaging all or portions of the microbial culture. The method may comprise growing the microbial culture and measuring characteristics of the microbial culture. A method may comprise steps of measuring characteristics of the microbial culture comprising measuring the predation of one or more selected microorganism by one or more other selected microorganisms, measuring factors excreted by the microorganisms, pH changes, or extracellular enzymes excreted by one or more selected microorganisms and its effects on one or more other selected microorganism, measuring the number of cells per mL of one or more selected microorganism in the microbial culture, determining growth rate for one or more selected microorganisms, or one or more combinations of measurements. A method may comprise using the measured characteristics of the microbial culture to determine if one or more microorganisms is to be removed from the incubation mixed culture or if one or more microorganisms is to be added to the incubation mixed culture, or if no change in microorganisms is to be made.

A method for preparing a cell-free supernatant composition comprising the steps of (a) inoculating a fermentation broth with an isolated microorganism, wherein the microorganism comprises *Aspergillus* spp., *Bacillus* spp., *Rhodopseudomonas* spp., *Candida* spp., *Lactobacillus* spp., *Pseudomonas* spp., *Saccharomyces* spp., or *Streptococcus* spp.; or combinations thereof; (b) incubating the inoculated fermentation broth for at least five hours; (c) centrifuging the culture after step (b) for at least 10 minutes at a centrifugal force of at least 14,000×g; and (d) filtration with a 0.22 um MCE filter; thereby providing the cell-free supernatant. The method wherein the *Aspergillus* spp. is *Aspergillus oryzae* or wherein the *Aspergillus* spp. is *Aspergillus oryzae*, IN-AO1, deposited with the ATCC Patent Depository under the Budapest Treaty, on Sep. 4, 2014, with the designation IN-AO1, under Account No. 200139, with the ATCC Patent Deposit Designation No. PTA-121551. The method wherein the *Bacillus* spp. is *Bacillus subtilis*, or wherein the *Bacillus* spp. is *Bacillus subtilis*, IN-BS1, ATCC Patent Deposit Designation No. PTA-12385. The method wherein the *Rhodopseudomonas* spp. is *Rhodopseudomonas palustris*, or wherein the *Rhodopseudomonas* spp. is *Rhodopseudomonas palustris*, IN-RP1, ATCC Patent Deposit Designation No, PTA-12387. The method wherein the *Candida* spp. is *Candida utilis* or wherein the *Candida* spp. is *Candida utilis*, IN-CU1, deposited with the ATCC Patent Depository under the Budapest Treaty, on Sep. 4, 2014, with the designation IN-CU1, under Account No. 200139, with the ATCC Patent Deposit Designation No. PTA-121550. The method wherein the *Lactobacillus* spp. is *Lactobacillus casei, Lactobacillus helveticus, Lactobacillus lactis, Lactobaccillus rhamnosus*, or *Lactobacillus plantarum*, or combinations thereof, or wherein the *Lactobacillus* spp. is *Lactobacillus helveticus*, IN-LH1, ATCC Patent Deposit Designation No. PTA-12386, or wherein the *Lactobacillus* spp. is *Lactobacillis casei*, referred to herein as IN-LC1, which was deposited with the ATCC Patent Depository under the Budapest Treaty, with the designation IN-LC1, on Sep. 4, 2014, under Account No. 200139, with the ATCC Patent Deposit Designation No. PTA-121549, or wherein the *Lactobacillus* spp. is *Lactobacillis lactis*, referred to herein as IN-LL1, which was deposited with the ATCC Patent Depository under the Budapest Treaty, with the designation IN-LL1, on Sep. 4, 2014, under Account No. 200139, with the ATCC Patent Deposit Designation No. PTA-121552, or wherein the *Lactobacillus* spp. is *Lactobacillus plantarum*, IN-LP1, deposited with the ATCC Patent Depository under the Budapest Treaty, on Sep. 4, 2014, with the designation IN-LP1, under Account No. 200139, with the ATCC Patent Deposit Designation No. PTA-121555, or wherein the *Lactobacillus* spp. is *Lactobacillus* rhamnosus, IN-LR1, deposited with the ATCC Patent Depository under the Budapest Treaty, on Sep. 4, 2014, with the designation IN-LR1, under Account No. 200139, with the ATCC Patent Deposit Designation No. PTA-121554. The method, wherein the *Pseudomonas* spp. is *Pseudomonas aeruginosa*. The method wherein the *Rhodopseudomonas* spp. is *Rhodopseudomonas palustris*, or wherein the *Rhodopseudomonas* spp. is *Rhodopseudomonas palustris*, IN-RP1, ATCC Patent Deposit Designation No. PTA-12383, or wherein the *Rhodopseudomonas* spp. is *Rhodopseudomonas palustris*, IN-RP2, deposited with the ATCC Patent Depository under the Budapest Treaty, on Sep. 4, 2014, with the designation IN-RP2, under Account No. 200139, with the ATCC Patent Deposit Designation No. PTA-121553. The method wherein the *Saccharomyces* spp. is *Saccharomyces cerevisiae*, or wherein the *Saccharomyces* spp. is *Saccharomyces cerevisiae*, IN-SC1, ATCC Patent Deposit Designation No. PTA-12384. The method wherein the *Streptococcus* spp. is *Streptococcus lactis*. The method wherein the microbial culture further comprises least one isolated micorrhyzal fungus. The method wherein the microbial culture is inoculated with of at least two of *Aspergillus* spp., *Bacillus* spp., *Rhodopseudomonas* spp., *Candida* spp., *Lactobacillus* spp., *Pseudomonas* spp., *Saccharomyces* spp., or *Streptococcus* spp. The method wherein the microbial culture is inoculated with *Aspergillus oryzae, Bacillus subtilis, Lactobacillus helveticus, Lactobacillus casei, Rhodopseudomonas palustris*, and *Saccharomyces cervisiase*. The method wherein the microbial culture is inoculated with a mixed culture, IN-M1, ATCC Patent Deposit Designation No. PTA-12383. The method wherein the microbial culture is inoculated with *Aspergillus oryzae, Bacillus subtilis, Candida utilis, Lactobacillus casei, Lactobacillus helveticus, Lactobacillus plantarum, Lactobacillus* rhamnosus, *Lactococcus lactis, Rhodopseudomonas palustris*, and *Saccharomyces cervisiase*. The method wherein the microbial culture comprises is inoculated with a mixed culture, IN-M2, deposited with the ATCC Patent Depository under the Budapest Treaty, on Sep. 4, 2014, with the designation IN-M2, under Account No. 200139, with the ATCC Patent Deposit Designation No. PTA-121556. The method further comprising step (e) sterilizing the cell-free supernatant. Sterilizing may be filter sterilization. The method wherein the time for incubating the inoculated fermentation broth (microbial culture) is for at least 24 hours, or for at least 60 hours, or for at least 120 hours, or for at least 360 hours. A cell-free supernatant composition prepared by the method.

In an aspect, a method further comprises the step (e) of sterilizing the cell-free supernatant.

In an aspect, sterilizing is by filter sterilization.

In an aspect, incubating the microbial culture is a time period of at least 24 hours. In an aspect, incubating the microbial culture is a time period of at least 60 hours. In an aspect, incubating the microbial culture is a time period of at least 120 hours. In an aspect, incubating the microbial culture is a time period of at least 360 hours. Those of skill in the art can determine an efficacious time period for incubating a microbial culture and the time may depend on the method of use of the cell-free supernatant composition derived from the microbial culture.

In an aspect, a cell-free supernatant is formed from a microbial culture by removing the cells of a microbial culture via centrifugation. Through centrifugation, cellular components of the culture (i.e., bacteria) are separated from the supernatant for the purpose of providing a cell-free supernatant composition. A use of the cell-free supernatant composition is to add a portion of a cell-free supernatant composition to a microbial culture. A step in making a microbial culture may be the addition of a cell-free supernatant composition to the microbial culture.

In an aspect, centrifugation can be carried out at from about 1,000 rpm to about 15,000 rpm. In an aspect, centrifugation can be carried out at from about 2,500 rpm to about 15,000 rpm. In an aspect, centrifugation can be carried out at from about 5,000 rpm to about 15,000 rpm. In an aspect, centrifugation can be carried out at from about 7,500 rpm to about 15,000 rpm. In an aspect, centrifugation can be carried out at from about 10,000 rpm to about 15,000 rpm. In an aspect, centrifugation can be carried out at from about 12,500 rpm to about 15,000 rpm. In an aspect, centrifugation can be carried out at from about 1,000 rpm to about 12,500 rpm. In an aspect, centrifugation can be carried out at from about 1,000 rpm to about 10,000 rpm. In an aspect, centrifugation can be carried out at from about 1,000 rpm to about 7,500 rpm. In an aspect, centrifugation can be carried out at from about 1,000 rpm to about 5,000 rpm. In an aspect, centrifugation can be carried out at from about 1,000 rpm to about 2,500 rpm.

In an aspect, a cell-free supernatant is formed (or derived, produced, or made) from a microbial culture wherein the cells or solid material is separated from the liquid portion of the microbial culture via filtration. In an aspect, filtration is accomplished with an ultrafiltration membrane. Examples of high-performance synthetic polymers commonly used in the formation of ultrafiltration membranes include polysulfone, polyethersulfone, and polyacrylonitrile.

In an aspect, an ultrafiltration membrane has a pore size of from about 0.01 μM to about 0.1 μM. In an aspect, an ultrafiltration membrane has a pore size of from about 0.03 μM to about 0.1 μM. In an aspect, an ultrafiltration membrane has a pore size of from about 0.05 μM to about 0.1 μM. In an aspect, an ultrafiltration membrane has a pore size of from about 0.07 μM to about 0.1 μM. In an aspect, an ultrafiltration membrane has a pore size of from about 0.09 μM to about 0.1 μM. In an aspect, an ultrafiltration membrane has a pore size of from about 0.01 μM to about 0.09 μM. In an aspect, an ultrafiltration membrane has a pore size of from about 0.01 μM to about 0.07 μM. In an aspect, an ultrafiltration membrane has a pore size of from about 0.01 μM to about 0.05 μM. In an aspect, an ultrafiltration membrane has a pore size of from about 0.01 μM to about 0.03 μM.

In an aspect an ultrafiltration membrane has a pore size of from about 1,000 nominal molecular weight cutoff (NMWC) to about 750,000 NMWC. In an aspect, an ultrafiltration membrane has a pore size of from about 3,000 NMWC to about 750,000 NMWC. In an aspect, an ultrafiltration membrane has a pore size of from about 5,000 NMWC to about 750,000 NMWC. In an aspect, an ultrafiltration membrane has a pore size of from about 10,000 NMWC to about 750,000 NMWC. In an aspect, the ultrafiltration membrane has a pore size of from about 30,000 NMWC to about 750,000 NMWC. In an aspect, an ultrafiltration membrane has a pore size of from about 50,000 NMWC to about 750,000 NMWC. In an aspect, an ultrafiltration membrane has a pore size of from about 100,000 NMWC to about 750,000 NMWC. In an aspect, an ultrafiltration membrane has a pore size of from about 300,000 NMWC to about 750,000 NMWC. In an aspect, an ultrafiltration membrane has a pore size of from about 500,000 NMWC to about 750,000 NMWC. In an aspect, an ultrafiltration membrane has a pore size of from about 1,000 NMWC to about 500,000 NMWC. In an aspect, an ultrafiltration membrane has a pore size of from about 1,000 NMWC to about 300,000 NMWC. In an aspect, an ultrafiltration membrane has a pore size of from about 1,000 NMWC to about 100,000 NMWC. In an aspect, an ultrafiltration membrane has a pore size of from about 1,000 NMWC to about 750,000 NMWC. In an aspect, an ultrafiltration membrane has a pore size of from about 1,000 NMWC to about 50,000 NMWC. In an aspect, an ultrafiltration membrane has a pore size of from about 1,000 NMWC to about 30,000 NMWC. In an aspect, an ultrafiltration membrane has a pore size of from about 1,000 NMWC to about 10,000 NMWC. In an aspect, an ultrafiltration membrane has a pore size of from about 1,000 NMWC to about 5,000 NMWC. In an aspect, an ultrafiltration membrane has a pore size of from about 1,000 NMWC to about 3,000 NMWC.

In an aspect, the ultrafiltration membrane is a hollow fiber cross flow ultrafiltration membrane. Hollow fiber membrane cross flow filtration is widely employed for cell concentration, which is typically the "dewatering" of bacterial or mammalian cell culture. This process is usually considered a straightforward concentration of particulates, but may also include a cell washing step to remove media components prior to the succeeding steps, such as homogenization (i.e., microfluidization).

In an aspect, a hollow fiber cross flow ultrafiltration membrane has an effective area of from about 0.0016 $m^2$ to about 0.0028 $m^2$. In an aspect, a hollow fiber cross flow ultrafiltration membrane has an effective area of from about 0.005 $m^2$ to about 28 $m^2$. In an aspect, a hollow fiber cross flow ultrafiltration membrane has an effective area of from about 0.010 $m^2$ to about 28 $m^2$. In an aspect, a hollow fiber cross flow ultrafiltration membrane has an effective area of from about 0.05 $m^2$ to about 28 $m^2$. In an aspect, a hollow fiber cross flow ultrafiltration membrane has an effective area of from about 0.1 $m^2$ to about 28 $m^2$. In an aspect, a hollow fiber cross flow ultrafiltration membrane has an effective area of from about 0.5 $m^2$ to about 28 $m^2$. In an aspect, a hollow fiber cross flow ultrafiltration membrane has an effective area of from about 1 $m^2$ to about 28 $m^2$. In an aspect, a hollow fiber cross flow ultrafiltration membrane has an effective area of from about 5 $m^2$ to about 28 $m^2$. In an aspect, a hollow fiber cross flow ultrafiltration membrane has an effective area of from about 10 $m^2$ to about 28 $m^2$. In an aspect, a hollow fiber cross flow ultrafiltration membrane has an effective area of from about 15 $m^2$ to about 28 $m^2$. In an aspect, a hollow fiber cross flow ultrafiltration membrane has an effective area of from about 20 $m^2$ to about 28 $m^2$. In an aspect, a hollow fiber cross flow ultrafiltration membrane has an effective area of from about 25 $m^2$ to about 28 $m^2$. In an aspect, a hollow fiber cross flow ultrafiltration membrane has an effective area of from about 0.0016 $m^2$ to about 25 $m^2$. In an aspect, a hollow fiber cross flow ultrafiltration membrane has an effective area of from about 0.0016 $m^2$ to about 20 $m^2$. In an aspect, a hollow fiber cross flow ultrafiltration membrane has an effective area of from about 0.0016 $m^2$ to about 15 $m^2$. In an aspect, a hollow fiber cross flow ultrafiltration membrane has an effective area of from about 0.0016 $m^2$ to about 10 $m^2$. In an aspect, a hollow fiber cross flow ultrafiltration membrane has an effective area of from about 0.0016 $m^2$ to about 5 $m^2$. In an aspect, a hollow fiber cross flow ultrafiltration membrane has an effective area of from about 0.0016 $m^2$ to about 1 $m^2$. In an aspect, a hollow fiber cross flow ultrafiltration membrane has an effective area of from about 0.0016 $m^2$ to about 0.5 $m^2$. In an aspect, a hollow fiber cross flow ultrafiltration membrane has an effective area of from about 0.0016 $m^2$ to about 0.1 $m^2$. In an aspect, a hollow fiber cross flow ultrafiltration membrane has an effective area of from about 0.0016 $m^2$ to about 0.05 $m^2$. In an aspect, a hollow fiber cross flow ultrafiltration membrane has an effective area of from about 0.0016 $m^2$ to about 0.01 $m^2$. In an aspect, a hollow fiber cross flow ultrafiltration membrane has an effective area of from about 0.0016 $m^2$ to about 0.005 $m^2$.

It will be understood that the aspects of the present disclosure which have been described are illustrative of some of the applications of the principles of the present disclosure. Numerous modifications may be made by those skilled in the art without departing from the true spirit and scope of the disclosure.

The disclosure has been described with reference to specific aspects thereof. It will, however, be evident that various modifications and changes may be made thereto without departing from the broader spirit and scope of the disclosure. The specification and drawings are, accordingly, to be regarded in an illustrative rather than a restrictive sense

EXAMPLES

Example 1—A Method for Making a Microbial Culture for Preparation of a Cell-Free Supernatant Composition A microorganism, such as a bacteria or yeast, was selected for inclusion in the composition, based on its enzyme activity profile, its ability to grow in media, its lack of spore formation, or other criteria described herein. The microorganism was grown in standard medium for that organism and when at an exponential growth phase, was aliquoted and stored. The media for growing microorganisms, such as yeasts and bacteria, are known to those skilled in the art.

For example, in making I-M Lab, an aliquot (5 mL of cells at $1 \times 10^6$) of each of IN-LH1, IN-BS1 and *L. casei* were added to a media suitable for lactobacilli and *bacillus*, such as water (700 mL), molasses (37.5 g), bentonite clay (3.75 g), and sea salt (3.75 g). The bacteria were grown to an optical density of 0.752 determined at 600 nm (hereinafter, "$OD_{600}$").

In making I-M PNSB, an aliquot (5 mL of cells at $1 \times 10^6$) of IN-RP1 was added to a media suitable for phototrophic bacteria. For example, water (134 mL), fish emulsion (9 mL), and IN-SC1 culture ($1 \times 10^6$ cells, 1 mL) were combined, and then the volume was adjusted to 144 mL with water and the cells were grown to an $OD_{600}$ 0.856. A carbohydrate source (i.e., molasses) can also be added. The fish emulsion used herein is commercially available as an organic soil amendment from Nutrivert, Dunham, Quebec (non-pasteurized).

In making I-M Yeast, an aliquot (5 mL of cells at $1 \times 10^6$) of IN-SC1 and *A. oryzae* ($OD_{600}$ 0.3) South River Miso Company, in Conway, Mass., USA were added to a media suitable for yeast, such as water (390 mL), molasses (1 g), fish emulsion (29 g), kelp (9 g), and wheat germ (1 g) were combined, and the volume was adjusted to 432 ml with water and the bacteria were grown to an $OD_{600}$ 0.574.

To make microbial cultures, comprising microorganisms such as IN-M1 deposited with ATCC Patent Deposit Designation No. PTA-12383, the three microbial cultures were used. I-M Lab, I-M PNSB and I-M Yeast were added to a medium comprising water, molasses, mineral powder, sea salt, and wheat bran as shown below. The three microbial component mixtures were added in the percentages shown in the chart below. The seed culture (an initial mixed culture) comprised IN-RP1, IN-BS1, IN-SC1, *Aspergillus oryzae*, IN-LH1, and *Lactobacillus caseii* and was made under sterile conditions.

| Components of Composition | % |
|---|---|
| WATER | 88.70 |
| MOLASSES | 5.00 |
| I-M LAB | 2.00 |
| I-M PNSB | 2.00 |
| I-M YEAST | 1.00 |
| Bentonite clay (Utah) | 0.10 |
| SEA SALT (commercially available) | 0.10 |
| WHEAT BRAN | 0.10 |
| TOTAL | 100 |

The molasses, sea salt, wheat bran and mineral powder were dissolved in some of the warm water and the temperature was kept at 45-50° C. The I-M LAB, the I-M PNSB and I-M Yeast were added together into a separate container and blended. The total was 50 L, of which 20 L was I-M LAB, 20 L was I-M PNSB, and 10 L was I-M Yeast (the composition comprising these three microbial compositions may be referred to herein as a seed culture). This seed culture was added to the main tank of media and water was added to make 110 L, and the temperature was kept at 37° C. with light agitation until the pH is pH 4.0 and below.

A secondary fermentation culture (a mixed culture) was made to produce a stable concentrated culture (mixed culture) comprising approx. 1 billion microorganisms per liter ($1 \times 10^6$ cells/mL). A concentrated composition may have a shelf life of 3 years or more. A typical 1000 liter secondary fermentation batch, was inoculated with 50 litres of the seed culture (described above—20 L was I-M LAB, 20 L was I-M PNSB, and 10 L was I-M Yeast) and the media was 50-200 liters of non-sulphur agricultural molasses, 3.75 liters wheat bran, (0.02-0.05% by volume), 3.75 liters kelp, (0.02-0.05% by volume), 3.75 liters bentonite clay, (0.02-0.05% by volume), 1.25 liters fish emulsion (a commercially available organic soil amendment, from Nutrivert, Dunham, Quebec non-pasteurized, 1.25 liters soy flour, (0.005-0.03% by volume), 675 mg commercially available sea salt, and enough non-chlorinated warm water to make 1000 L.

The pH dropped to about 3.7 by Day 5 after inoculation, and the culture was grown and stirred lightly once per day and pH was monitored. The culture was incubated for 3-10 weeks at 32-37° C., resulting in the microorganism-containing composition used in the following examples. The composition was bottled and stored under anoxic conditions in airtight containers out of sunlight at room temperature. This resulting composition may be referred to as a concentrated composition, with cells at $1 \times 10^6$ cell s/mL.

Microbial compositions such as IN-M2, Batch ID 140226, and IN-M2, Batch ID 140227, were prepared from mixed culture stock, IN-M2, deposited with ATCC Patent Deposit Designation No. PTA-121556, as described above for IN-M1. The culture for Batch ID 140226 was incubated for 3-10 weeks at 30-32° C. and the culture for Batch ID 140227 was incubated for 3-10 weeks at 35-37° C.

In an alternative method, the secondary fermentation may contain one or more strains of microorganisms, such as those purchased from commercial entities, and/or endogenous microorganisms or microbial consortia isolated from an environment.

Example 2—Preparation of a Cell-Free Supernatant Composition

Cell-free supernatant ("CFS") composition was obtained by centrifuging the microbial culture prepared using the methods as described above for at least 10 minutes at a centrifugal force of 14,171×g. The CFS composition was then checked by absorbance (600 nm) to determine whether any microbes were still present and the liquid portion is removed via decanting or pipetting. The supernatant was then filter sterilized with a 0.22 μM micron filter (MCE membrane).

Example 3—Characterization of Compositions

The chemical characterizations of the cell-free supernatant compositions made from microbial cultures comprising IN-M1 (Product A) and IN-M2 (Product B) were determined. The results are fairly consistent for each cell-free supernatant composition, with each having fairly high levels of potassium (about 2500 μg per gram of composition), followed by nitrogen (435-600 μg per g composition), calcium (475-660 μg per g composition) and magnesium (200-260 μg per g composition). Sodium ranged from 160 to 360 ppm. The pH ranges were similar at 4.3-4.5. Sulphur was present at near 425-500 ppm in the cell-free supernatant compositions tested. Phosphorus was present in very low levels (50-90 ppm). All other metals were at trace levels, except iron which was present at about 20 ppm.

There were significant levels of volatile fatty acids with acetic being the highest (2000-2400 μg per g), followed by butyric acid (1300-1750 μg per g). The isobutyric content of product A was low at about 600 ppm but of Product B it was 650 ppm. Conversely, Product A had a propionic acid content of 940-1100 ppm whereas that of Product B was only 147 ppm.

Both samples contain relatively low amounts of volatile fatty acids (VFAs). VFAs such as acetic, propionic, butyric, isobutyric acids, etc., are metabolic products of bacterial anaerobic fermentation. These biochemicals have been detected in many types of partially fermented materials including liquid manures, composts, food products, and organic products which are stored anaerobically (Cooper and Cornforth (1978) *J. Sci. Food Agric.* 29, 19-27; Guenzi and Beard (1981) *J. Environ. Qual.* 10, 479-482; Patni and Jui (1985) *Agric. Wastes* 13, 159-178). VFAs can kill both human and animal microbial pathogens (Goepfert and Hicks (1969) *J. Bacteriol.* 97, 956-968; Kenealy, et al. (1995) *Appl. Microbiol. Biotechnol.* 44, 507-513; Kunte, et al. (1998) *J. Appl. Microbiol.* 84, 138-142), food spoilage organisms (Corsetti, et al. (1998) *Appl. Microbiol. Biotechnol.* 50, 253-256), and crop plants (Lynch, J. M. (1977) *J. Appl. Bacteriol.* 42, 81-87; Lynch, J. M. (1978) *Soil Biol. Biochem.* 10, 131-135). Acetic acid is a registered organic herbicide. High dilutions of acetic, propionic, isobutyric, butyric, and isovaleric acids are responsible for phytotoxicity of immature compost and have been shown to inhibit the growth of *Brassica rapa* L. when exposed to immature compost. The toxicity was related primarily to propionic and n-butyric acids (Chanyasak, et al. (1983) *Soil Sci. Plant Nutr.* 29, 251-259). The phytotoxicity often seen following incorporation of green manures was related to production of acetic acid produced during microbial degradation (Lynch, J.

M. (1977) *J. Appl. Bacteriol.* 42, 81-87; Lynch, J. M. (1978) *Soil Biol. Biochem.* 10, 131-135). VFAs are frequently added to silage and fruit to prevent rot, and acetic acid and propionic acids are used as food preservatives (Doores, S. (1993) *Organic acids. Pages* 95-136 in: Antimicrobials in Food. P. M. Davidson and A. L. Banen, eds. Marcel Dekker, New York; Ohyama, et al. (1977) 1 Sci. Food Agric. 28, 369-374). VFAs have been shown to suppress the growth of numerous microorganisms including plant pathogens (Abbasi, et al. (2009) *Phytopathology* 99, 274-281; Conn, et al. (2005) *Phytopathology* 95, 28-35; Tenuta, et al. (2002) *Phytopathology* 92, 548-552). Acetic acid in freshly composted municipal wastes suppressed colony growth of *Phytophthora nicotianae* and infection of citrus seedlings (Widmer, et al. (1998) *Plant Dis.* 82, 683-688). McKellar and Nelson (2003) (*Appl. Environ. Microbiol.* 69, 452-460) also found that compost-induced suppression of *Pythium* damping-off was mediated by fatty-acid-metabolizing seed colonizing microbial communities.

Though not wishing to be bound by any particular theory, it is currently believed, that the non-ionized forms of VFAs that are toxic (Freese, et al. (1973) *Nature* 241, 321-325). The proportion of ionized (i.e., acetate) to non-ionized (i.e., acetic acid) form of a VFA is dependent upon the pH of the solution. The dilution of the non-ionized form of an individual VFA in solution is estimated using the Henderson-Hasselbalch equation (Hasselbalch, K. A. (1915) *Biochem. Z.* 78, 112-144). The potential use of VFAs has been overlooked in agriculture despite the many obvious benefits they possess. For one, most are edible products with very low risk to humans and animals. They are short-lived in the environment, persisting in general for only days. They can act as sources of nutrition for many microorganisms in soil. Above all, they leave no chemical residues on the fruit surface allowing the application at any time during the growth stage. Sholberg (1998) (*Plant Dis.* 82, 689-693) developed a means to use acetic acid vapour as a fumigant of tender fruit to reduce the potential of postharvest decay. Some of the factors considered as beneficial however, can also be limitations. In soils with pH ranges above six, VFAs will exist mostly as salts and will not be biologically active. The pH of 4.5 is near the $pK_a$ of many of the VFAs in IN-M1; without wishing to be bound by theory, this may indicate that at least 50% of the VFAs should be in their biologically active form.

Example 4—Use of the Cell-Free Supernatant Compositions and Methods to Affect Germination Two germination trials were conducted using soy beans, radish, canola, arugula and wheat, and two batches of cell-free supernatant compositions as described in the Example above, IN-M1 (A) and IN-M2 (B). For trial 1 the dilutions tested were 1/10, 1/20× and 1/40 and for trial 2 the dilutions tested were 1/50, 1/100, 1/200, 1/400 and 1/800 in distilled water. All seeds were surface sterilized by rinsing in 70% ethanol for 30 seconds. They were then rinsed 3 times in sterile water and left to dry on a sterile paper towel. Two sheets of sterile filter paper were placed in the bottom of pre-sterilized plastic Petri dishes. Six mL of each dilution was added to the dish prior to adding the seeds. Control plates received an equal volume of water. When the filter paper was fully saturated, 10 seeds were randomly placed onto filter paper. Due to their large size, only 8 soybeans were added to each plate. The seeds were covered with one additional filter paper. The plates were sealed with parafilm and placed inside a growth chamber until fully germinated, approximately (seven days). Germinated seeds were counted and rated according to a germination scale created for each test. Control and each treatment were tested in triplicate.

One-way ANOVA followed by Dunnett's multiple comparisons test was performed on all data using GraphPad Prism version 6.00 for Windows, GraphPad Software, La Jolla Calif. USA, see also www.graphpad.com. Representative for the effect of the application of IN-M1 cell-free supernatant on seed germination is shown in FIGS. 1A-1B, 2A-2B, and 3A-3B. Additional experiments are described herein below.

Trial 1

In general, as concentrations of the cell-free supernatant compositions increased, seed germination and hypocotyl and root growth decreased with all crops. Differences in plant responses were found between batches A and B. Batch B was deleterious to arugula and radish at all concentrations tested.

To rate the results, a germination scale was created per crop that represents the different degrees of germination obtained. Each plate was rated using the appropriate scale.

Wheat

Figure 1B:
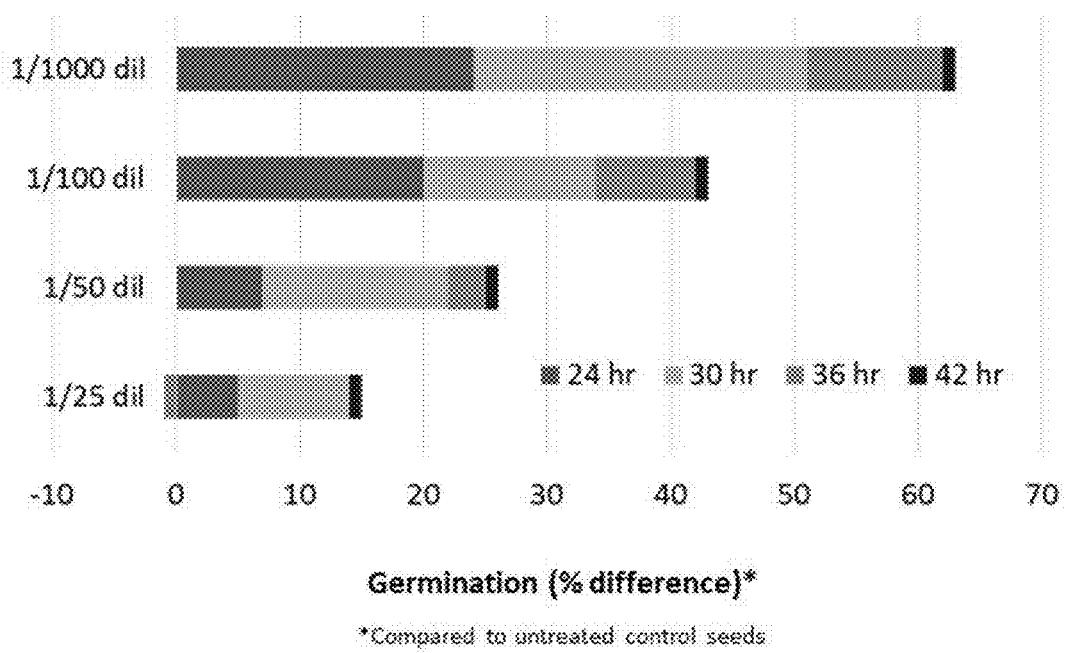
Figure 2A:
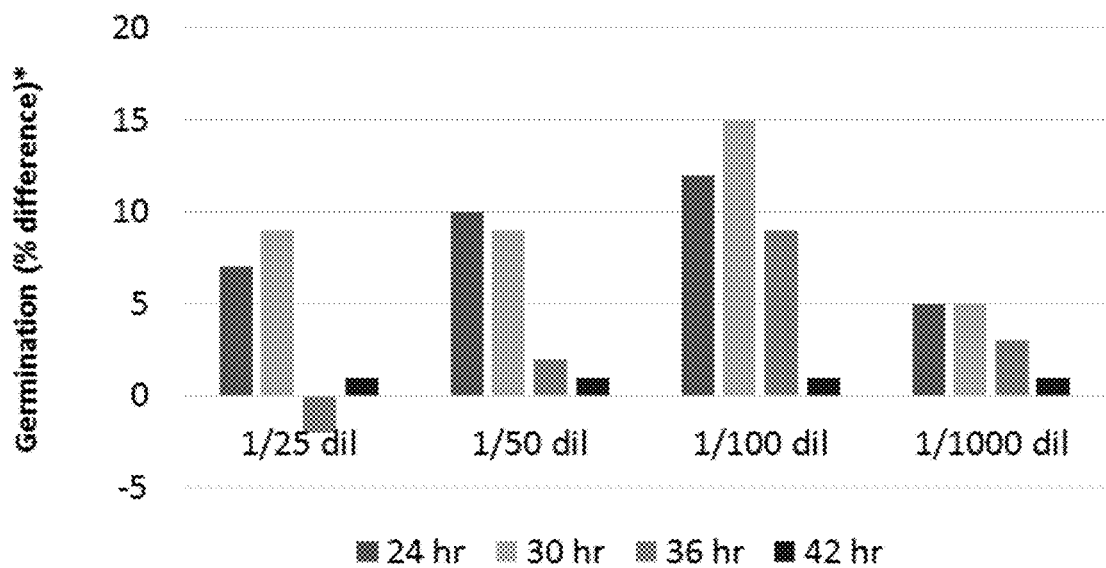
FIGS. 2A and 2B show representative data pertaining to the effect of disclosed compositions on germination.
Figure 2B:
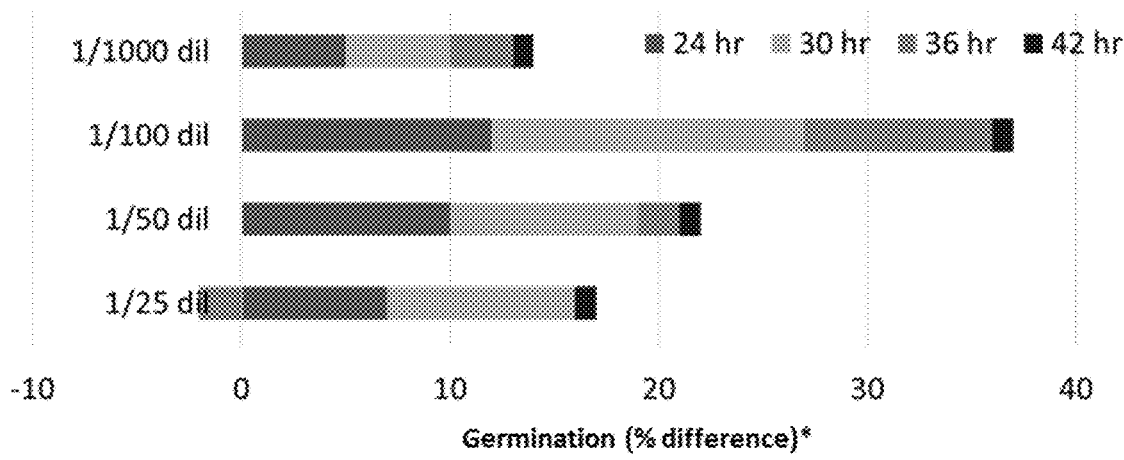
Figure 3A:
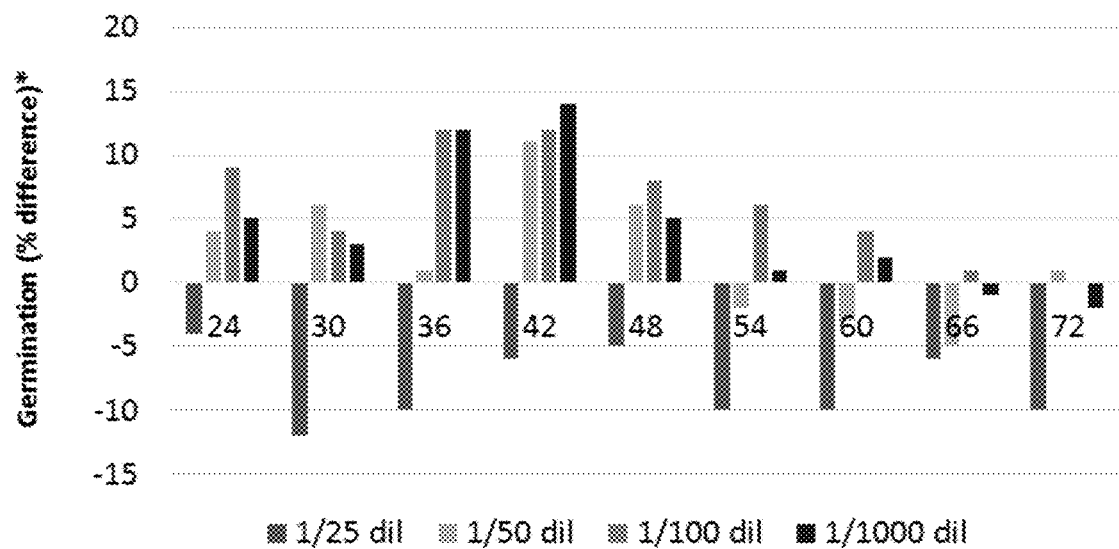
FIGS. 3A and 3B show representative data pertaining to the effect of disclosed compositions on germination carried under abiotic stress conditions. Seeds are exposed to 100 mM NaCl under abiotic stress conditions.
Figure 3B:
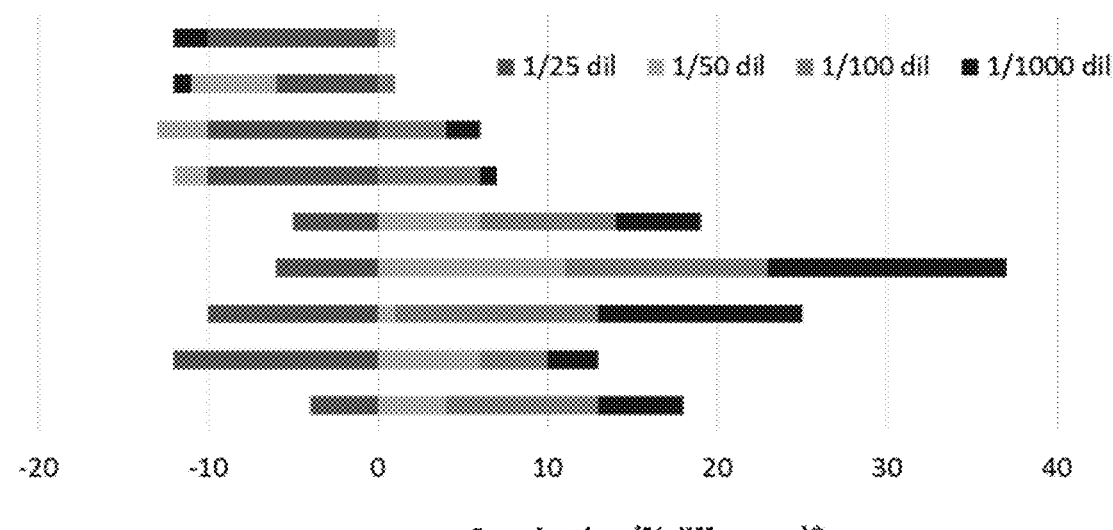
Figure 32A:
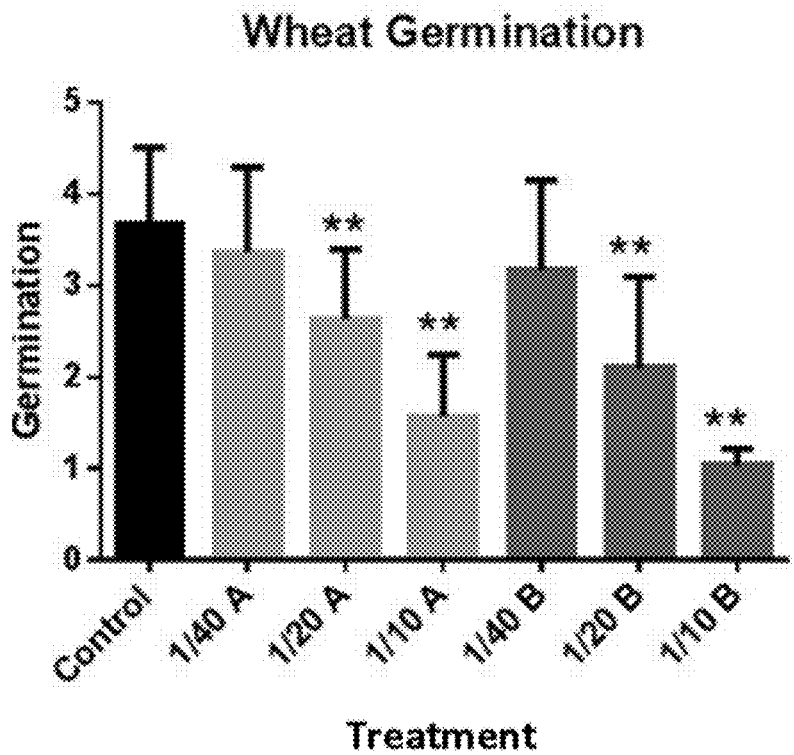
FIGS. 32A-32E show representative data pertaining to the effect of disclosed compositions on germination. The seed type is as indicated above each graph. "A" indicates IN-M1 cell-free supernatant, and "B" indicates IN-M2 cell-free supernatant. The dilution of the cell-free supernatant is as indicated below each bar.

Dilutions 1/10 and 1/20 of batches A and B had a negative effect on wheat germination (FIG. 32A), while no statistically significant differences were found between wheat germinated in the presence of 1/40 dilution of Inocucor products or control (FIG. 1B).

Canola

Figure 32B:
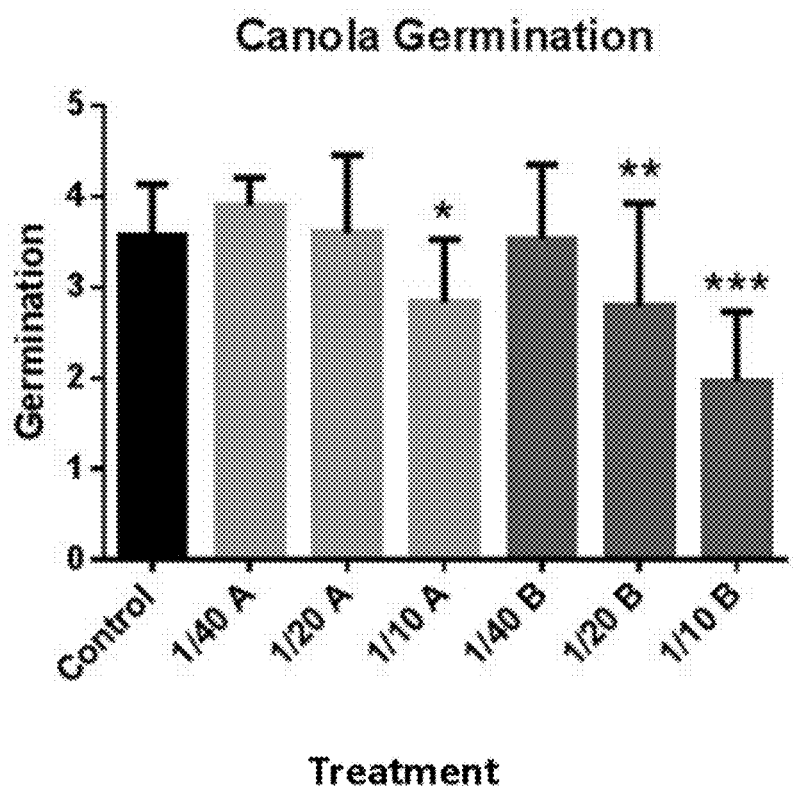

Differences between batches were more evident in this experiment. Dilutions of 1/10 and 1/20 of IN-M2 (B) negatively affected canola germination while only dilution 1/10 of batch IN-M1 (A) positively affected germination (FIG. 32B). When seeds where treated with 1/40 IN-M1 (A) seedlings had longer and more robust shoots than control plants but significantly smaller roots.

Arugula

Figure 32C:
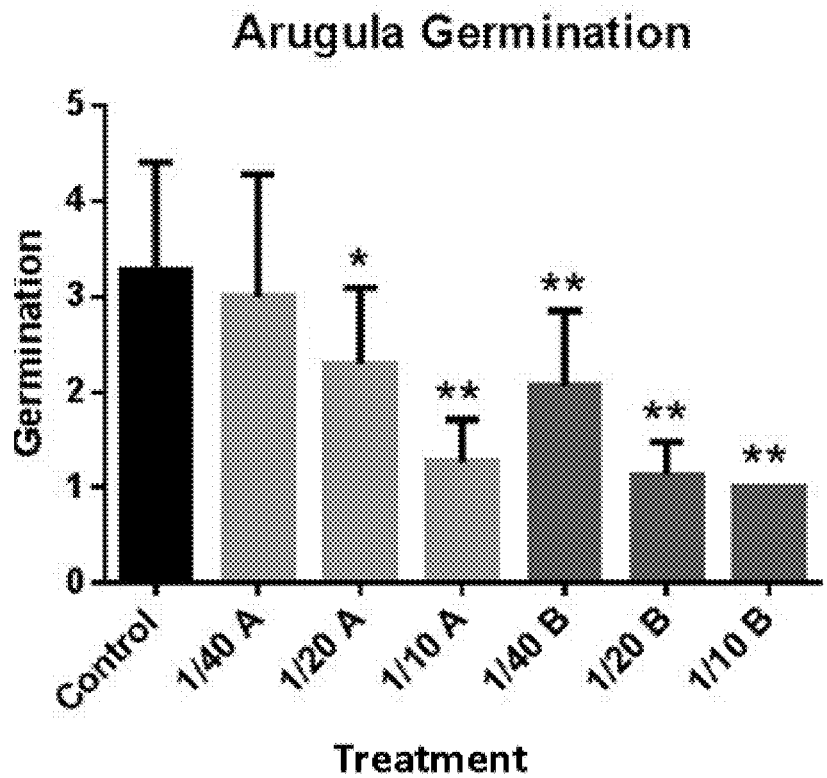
Figure 32D:
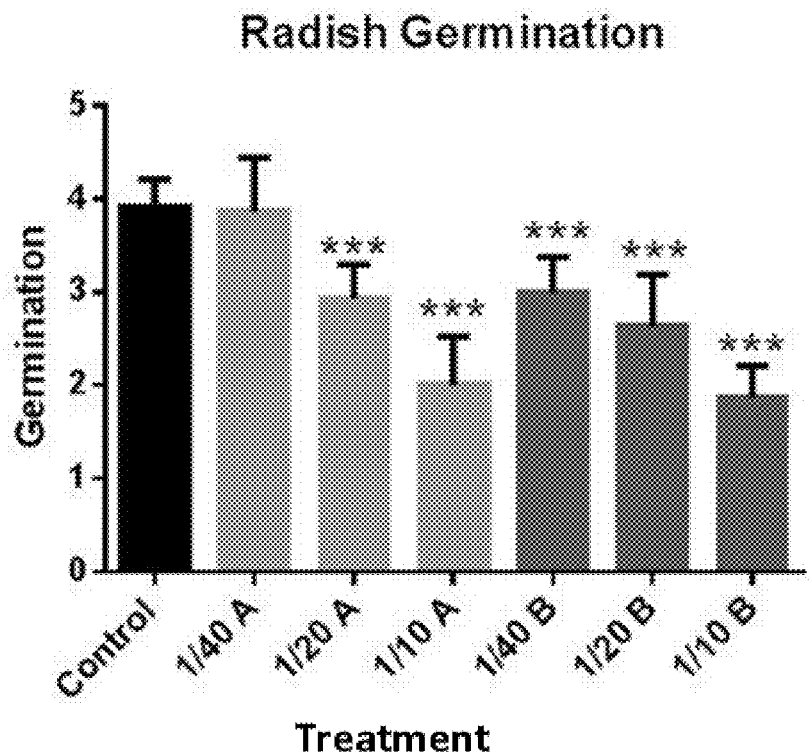

All IN-M2 (B) concentrations tested had a negative effect on arugula germination. Dilutions 1/10 and 1/20 of IN-M2 (B) completely inhibited germination and only few seeds germinated when treated with 1/40 IN-M2 (B). Dilutions 1/10 and 1/20 of the batch A (IN-M1) were also detrimental for arugula germination and only treatment 1/40 A germinated as control (FIG. 32C).

Radish

Although it did not inhibit germination, treatments with cell-free supernatant compositions of IN-M2 (B) were detrimental for radish germination. Only treatment 1/40 IN-M1 (A) germinated as control (FIG. 32C).

Soy Beans

Figure 32E:
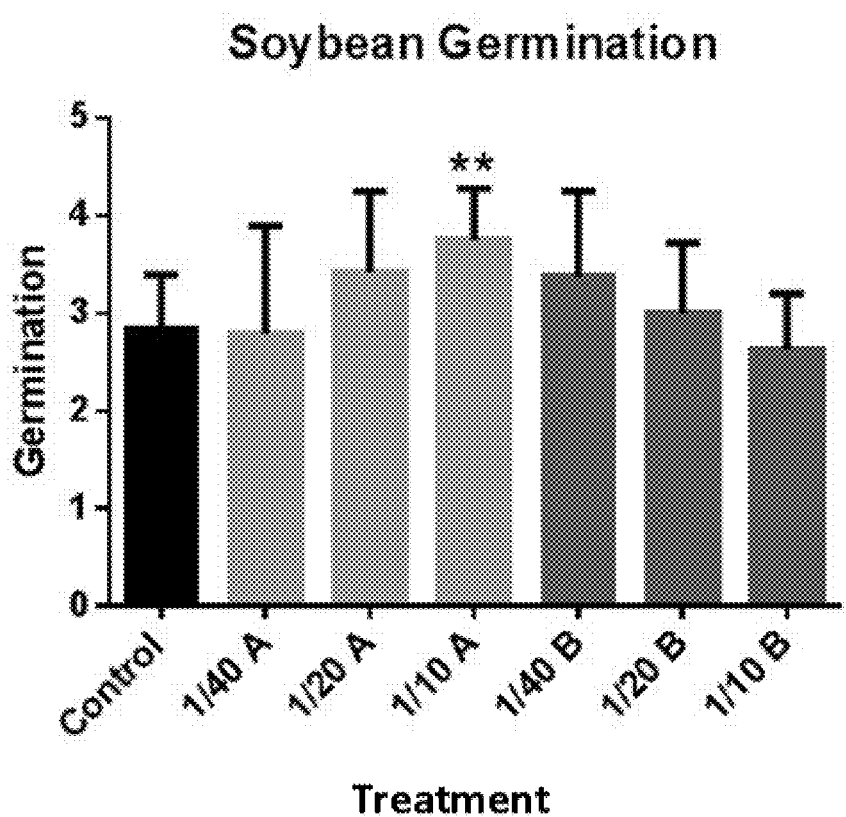
Figure 33B:
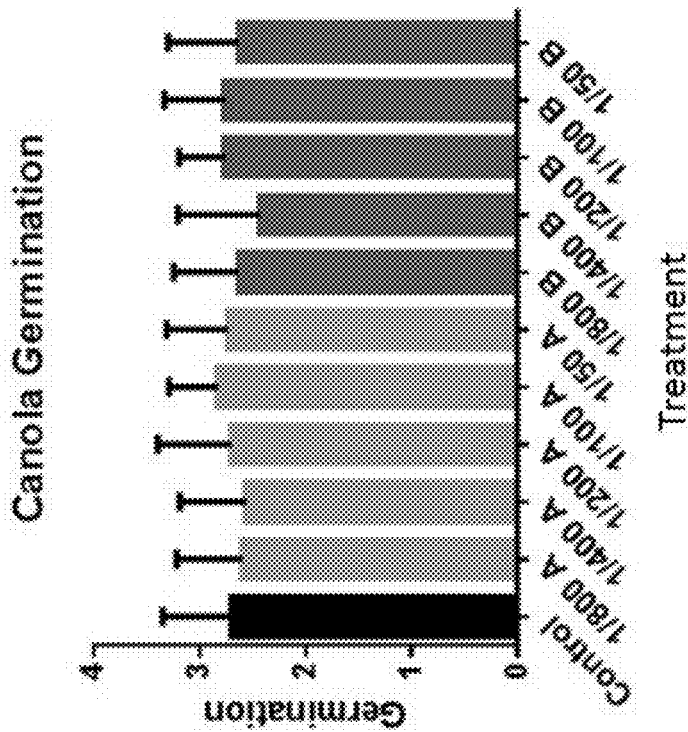
FIGS. 33A-33D show representative data pertaining to the effect of disclosed compositions on germination. The seed type is as indicated above each graph. "A" indicates IN-M1 cell-free supernatant, and "B" indicates IN-M2 cell-free supernatant. The dilution of the cell-free supernatant is as indicated below each bar.
Figure 33A:
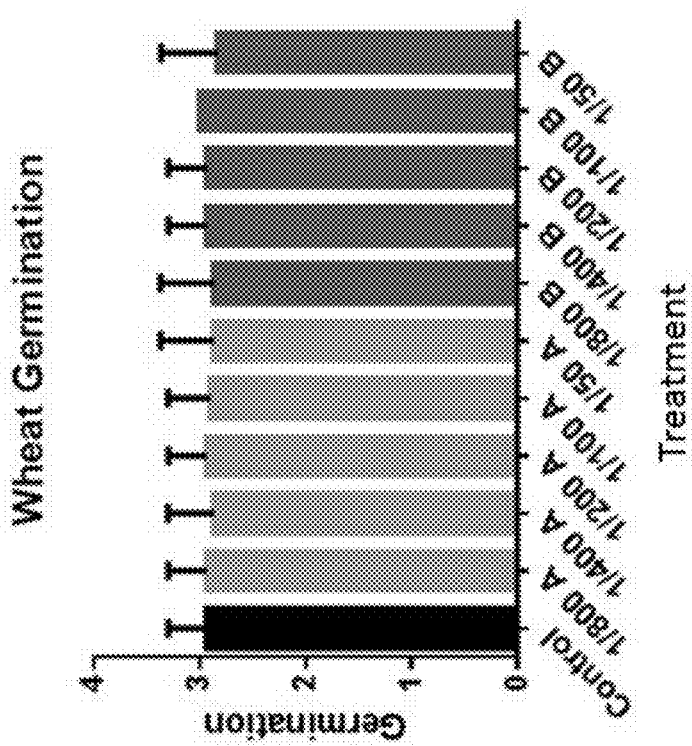
Figure 33D:
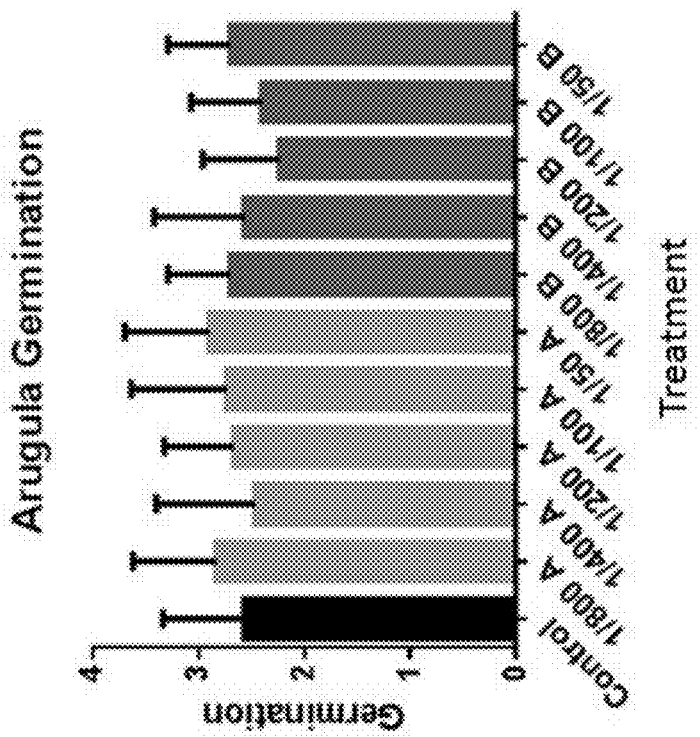
Figure 33C:
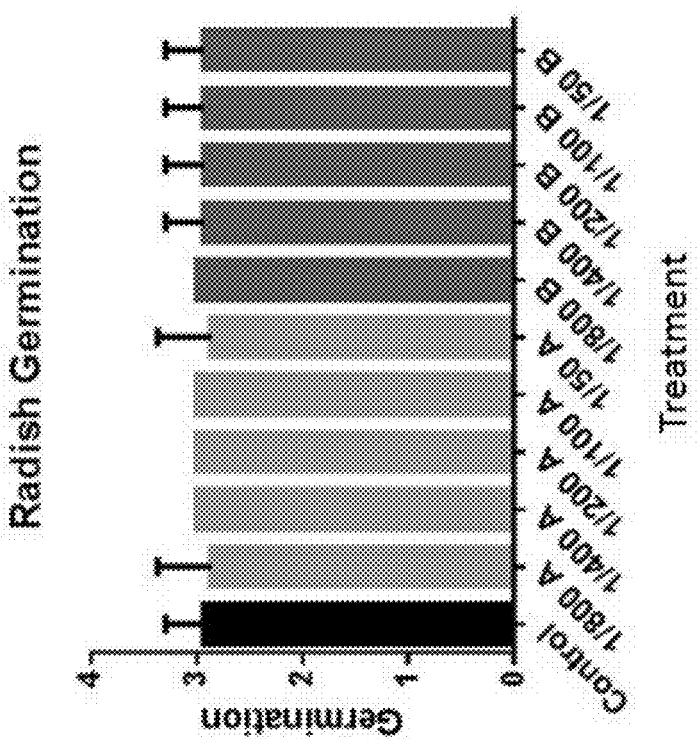

There was no inhibitory effect on soy bean germination at any dilution testes and with either formulation (FIG. 32E). In fact, treatment with the 1/40 dilution of a cell-free supernatant composition of IN-M1 (A) significantly improved seedling quality as compared to control.

Trial 2

Based on the previous results, a germination test was performed for 7 days with dilutions 1/50, 1/100, 1/200, 1/400 and 1/800 of ell-free compositions of IN-M1 (A) and IN-M2 (B). As shown in FIGS. 33A-D, none of the treatments affected germination on any of the seeds tested.

In summary, the higher concentrations of products IN-M1 (A) and IN-M2 (B) has some negative effects on seed germination; this was similar to that seen with inhibition of fungal growth. The exception was with soybeans where a positive effect of a cell-free supernatant composition of IN-M1 was observed at the highest rate tested of 1:10.

Germination was not affected when lower concentration of both IN-M1 and IN-M2 (dilutions 1/50 or higher) was used.

Example 5—Tracking the Shift in Bacterial and Fungal Community Profiles Present in Microbial Cultures Over Time Two batches of microbial cultures were delivered on Mar. 10, 2014 for chemical analysis and microbial community profiling. Batch "A" is IN-M1 and is a high salt formulation from 2011. Batch "B" is IN-M2 and is a low salt formulation in which no sodium chloride was added to the secondary fermentation and further comprising humic acid from 2013. The batches were prepared under anaerobic conditions and then placed into sealed plastic bottles. Due to the microbial content present in the product, exposure to oxygen and warm temperatures may cause the microbial community to grow and potentially shift. It is therefore important to identify how the communities change and what effect the storage conditions have on the shift.

Upon arrival at the lab, the two batches were stored in the 4° C. fridge. Each bottle was opened under sterile conditions in a biological safety cabinet and 60×1.5 mL subsamples were collected and stored in 2 mL micro centrifuge tubes. The 60 samples from each bottle were placed in freezer boxes and stored in a −80° C. freezer. These samples serve as the baseline and controls for the remainder of the experiment. An additional 6 1.5 mL samples were collected from each bottle for the "time zero" point.

In addition to the time zero samples, 9×45 mL subsamples from each bottle were collected and stored in 50 mL falcon tubes. Three tubes were placed in the 4° C. fridge, three in a 25° C. incubator and three on a lab bench at ambient room temperature. A total of 6 tubes (3 from batch A and 3 from batch B) were stored at each temperature location.

Once a month, 2×1.5 mL subsamples were taken from each 50 mL falcon tube from each temperature. A total of 6 subsamples per batch per temperature were collected for a total of 36 samples. Three control samples per batch were taken from the stock in the −80° C. freezer. Once a month for a year, 42 samples were collected and analyzed. Upon completion of the experiment, a total of 516 samples were taken and analyzed by TRFLP (12 months×42 samples=504 samples+the 12 samples taken at time zero). Samples were analyzed for both bacterial and fungal TRFLP. Thus, the total number of samples analyzed for TRFLP was 1032 samples (504 samples for bacteria and 504 samples for fungi plus the 24 (12 bacterial+12 fungal) samples taken at time zero).

Time Zero—Mar. 21, 2014

Figure 4:
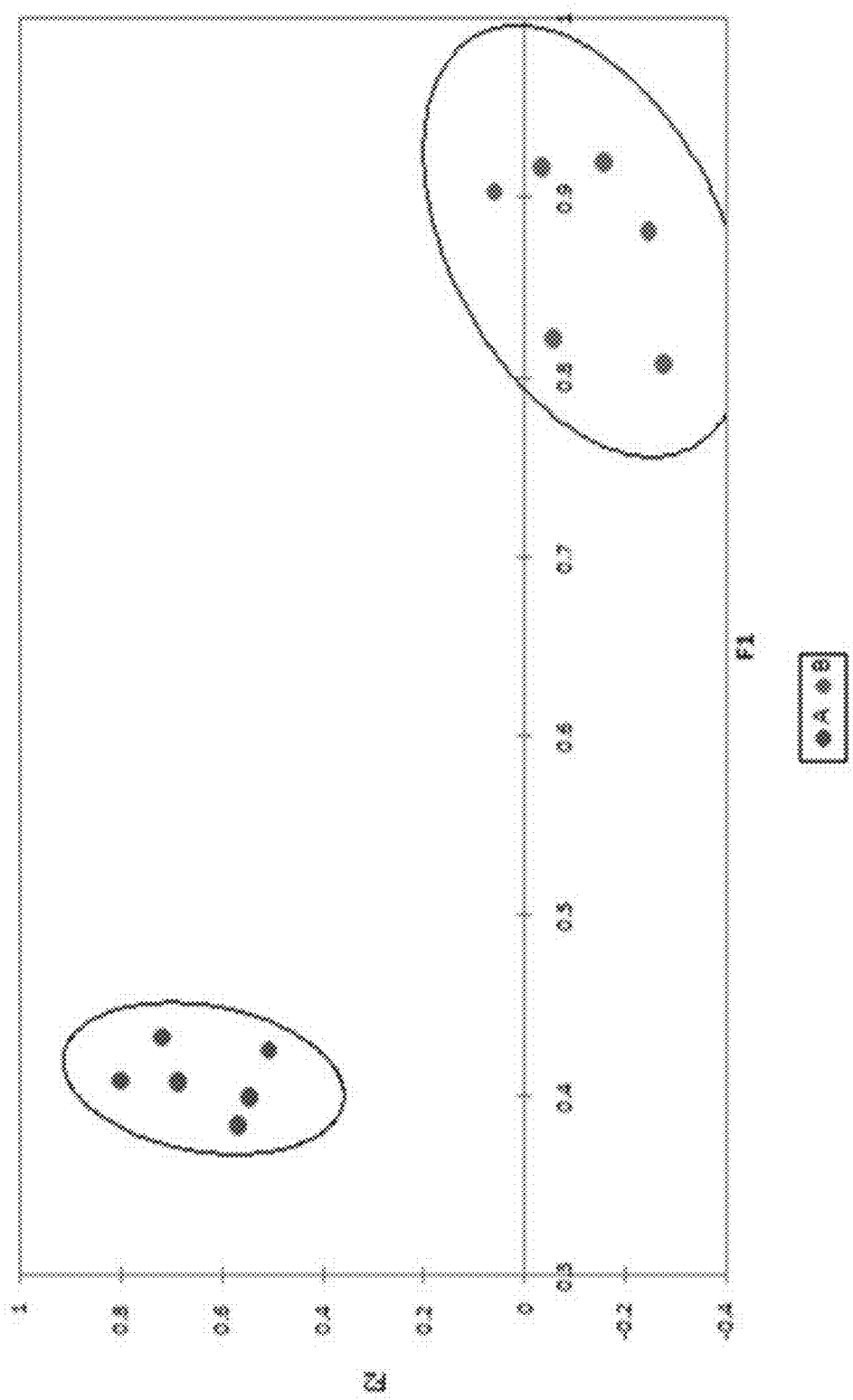
FIG. 4 shows representative data pertaining to the principle component analysis of the bacterial communities present in IN-M1 (A) and IN-M2 (B) at time zero.
Figure 5:
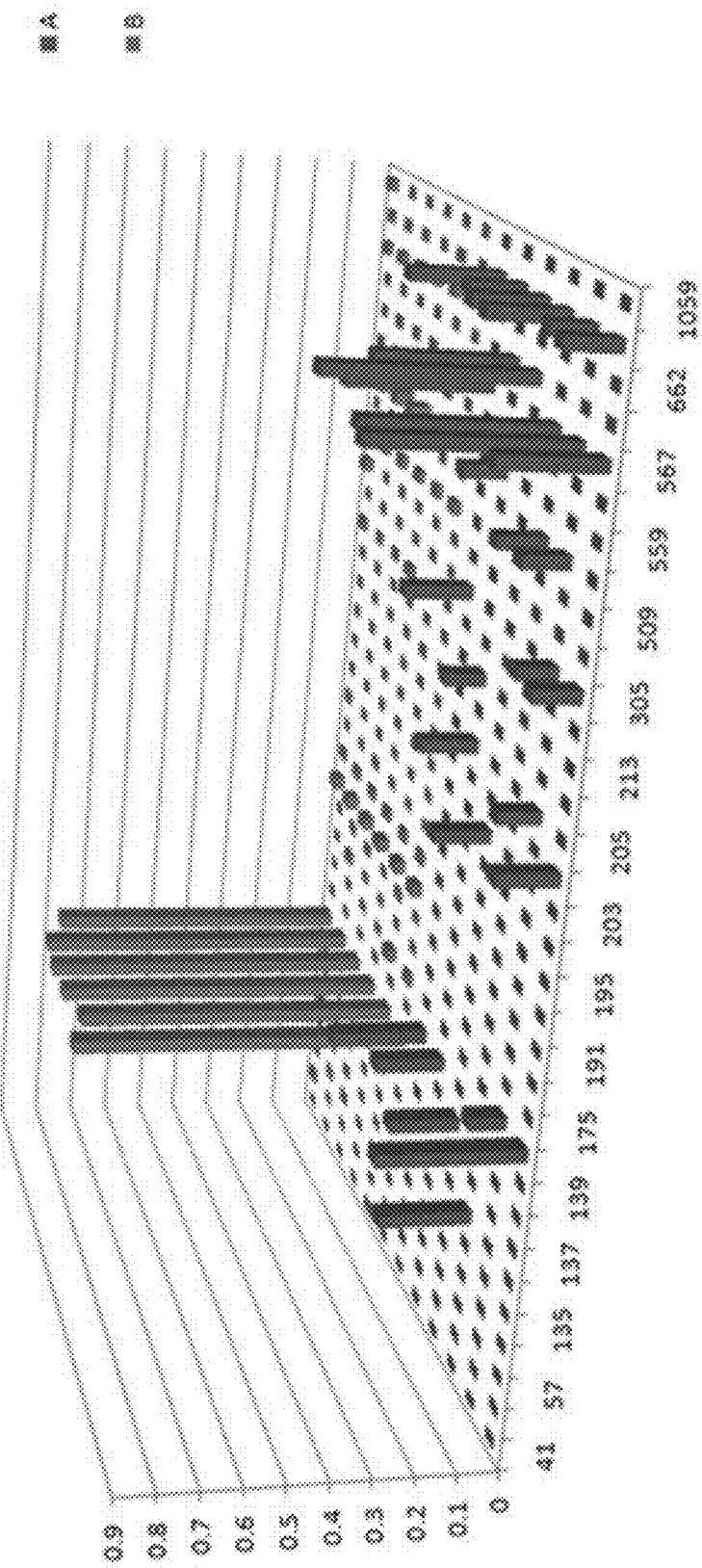
FIG. 5 shows representative data pertaining to the peak intensity profiles for the bacterial communities present in IN-M1 (A) and IN-M2 (B) at time zero.
Figure 6:
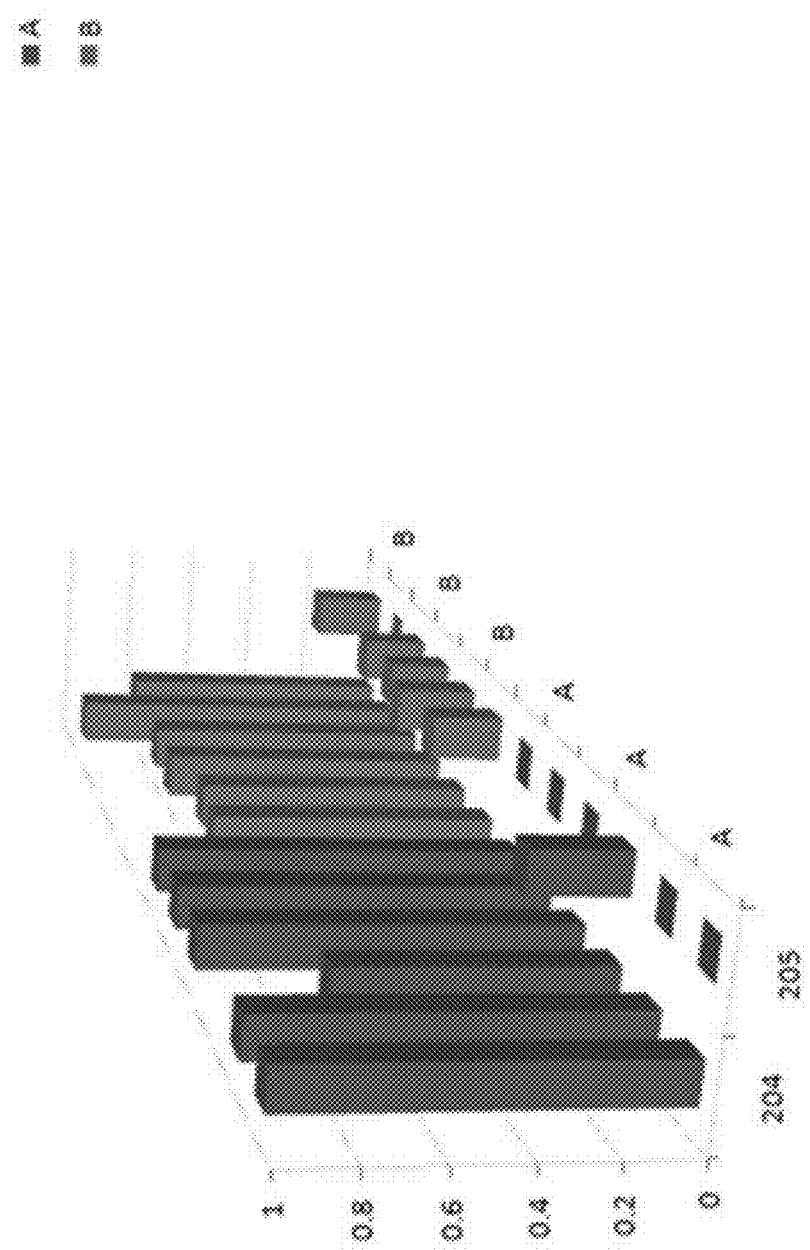
FIG. 6 shows representative data pertaining to the peak intensity profiles for the fungal communities present in IN-M1 (A) and IN-M2 (B) at time zero.

Time zero represents the microbial community present at the time the batch was first opened and exposed to oxygen. The batches were stored in a 4° C. fridge when they were received and time zero samples were taken within 2 days of the batches arriving at the lab. At time zero the bacterial communities of batch A and B were significantly different from one another (FIG. 4). Without wishing to be bound by theory, the differences observed by principal component analysis may be due to differences in community diversity between the batches. Each peak (either forward or reverse primer) theoretically represents one bacteria and the peak height represents the abundance. Batch A had a number of small peaks that were not found in batch B which would explain the significant results of the PCA. The 4 most abundant peaks present in batch A were at base pairs of 138, 305, 567/8 and 755 (FIG. 5). Batch B was dominated by 1 large peak at 138 base pairs (FIG. 5). The fungal communities of batch A and B were nearly identical and were both dominated by the same peak at 204 or 205 base pairs (FIG. 6). A principle component analysis was not done on the fungal community because there were only 1 or 2 peaks in each sample and it was clear that the profiles were the same.

Month 1—April 2014

Bacteria

Figure 7:
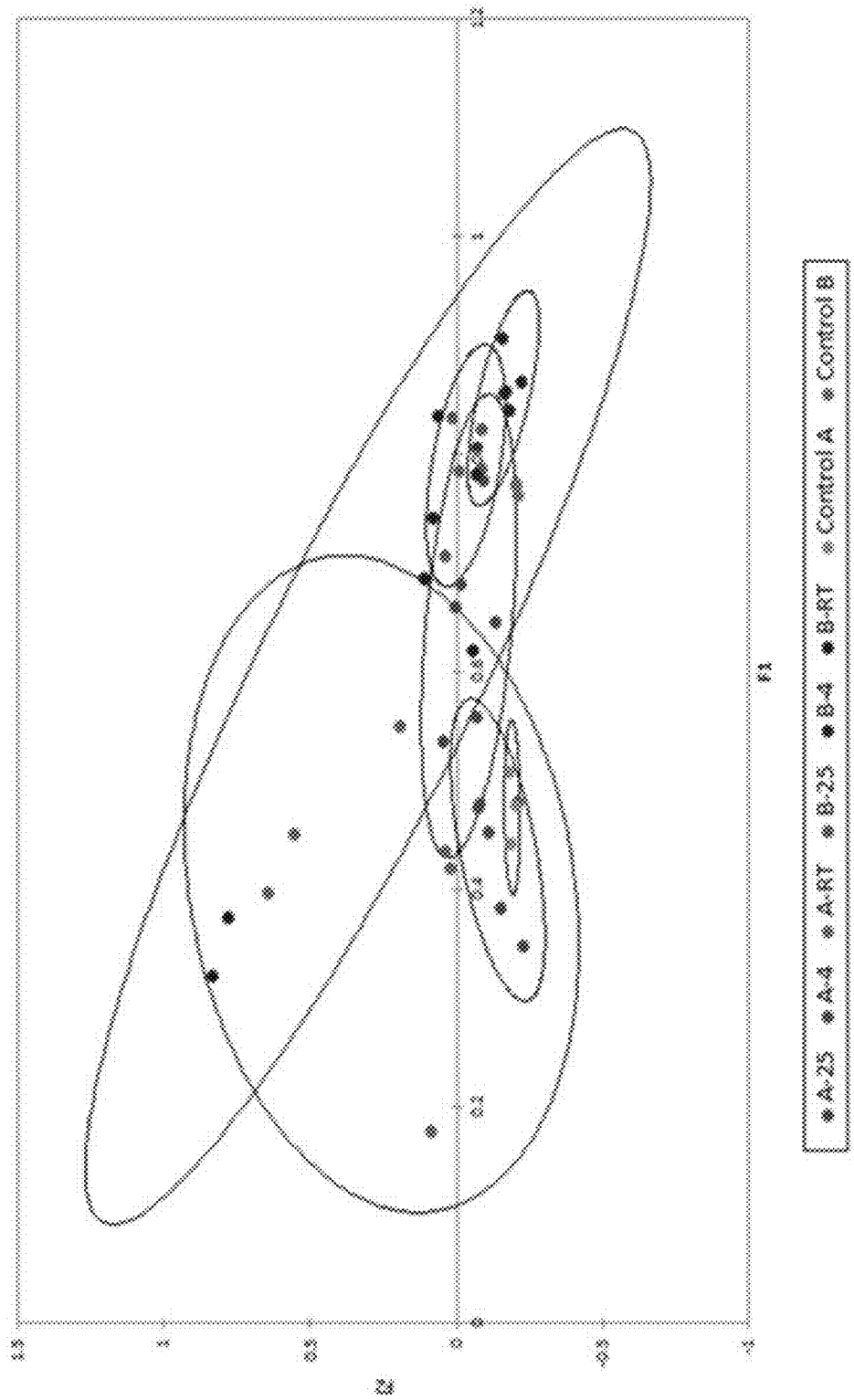
FIG. 7 shows representative data pertaining to the principle component analysis of bacterial communities present in IN-M1 (A) and IN-M2 (B) after one month of growth. Each batch was stored at 4° C., 25° C., −80° C. (control), and room temperature.

After 1 month of growth the bacterial communities in batches A and B were fairly similar with only a few showing some significant differences (FIG. 7). Control A and control B which were stored at −80° C. were significantly different which was consistent with the results of the time zero samples. Batch A stored at 4° C. and batch A stored at room temperature were significantly different from batch B stored at 25° C., 4° C. and the control. Batch A stored at 25° C. was significantly different from the batch A control. All four batch B samples were similar to one another with only the control clustering closely together and away from the batch B samples that were stored at 25° C. and 4° C. All four batch A samples were similar to one another with the exception of the control and the 25° C. samples which were significantly different.

IN-M1 (Batch A)

Figure 8:
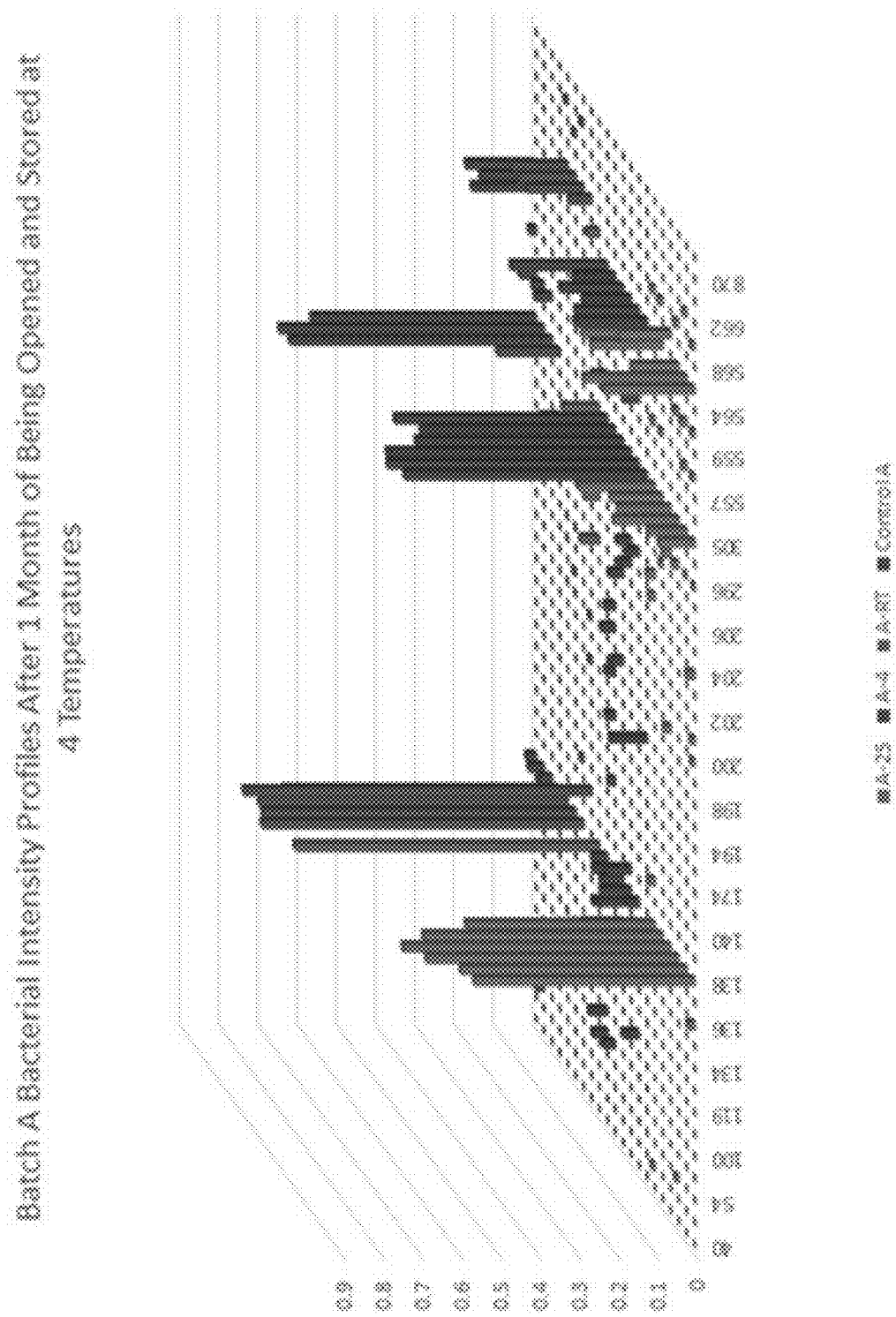
FIG. 8 shows representative data pertaining to the peak intensity profiles for the bacterial communities present in IN-M1 (A) after one month of growth at 4° C., 25° C., −80° C. (control), and room temperature.

After 1 month of growth the profiles of the batch A samples stored at −80° C., 4° C., 25° C., and room temperature all shared the same main peaks at 138, 305 and 567 base pairs (FIG. 8). However, the abundance of the shared peaks was very different between the 4 storage temperatures. The most abundant peak for the batch A samples stored at −80° C. and 4° C. was at 305 base pairs. The most abundant peak for batch A at 25° C. and room temperature was at 138 base pairs. It is interesting to note the difference in abundance between the 2 samples stored at low temperatures and the 2 samples stored at warm temperatures. At lower temperatures the organism responsible for the peak at 305 base pairs is the most dominant and has the highest intensity. At higher temperatures, the organism responsible for the peak at 138 base pairs is the most dominant and has the highest intensity. At room temperature, the peak at 305 base pairs was only found in 2 of the 6 reps and at very low intensity levels while the peak at 138 base pairs was in all 6 reps at the highest intensity levels of all the sample temperatures. Although the peaks at 138 and 305 base pairs experience a shift in abundance with changing temperature, the peak at 567/8 base remained relatively stable in abundance with the exception of room temperature where it was only present in 2 replications. Without wishing to be bound by theory, these results suggest that given the right environment the organism responsible for the peak at 138 base pairs proliferates and causes a decrease and/or elimination of other organisms.

IN-M2 (Batch B)

Figure 9:
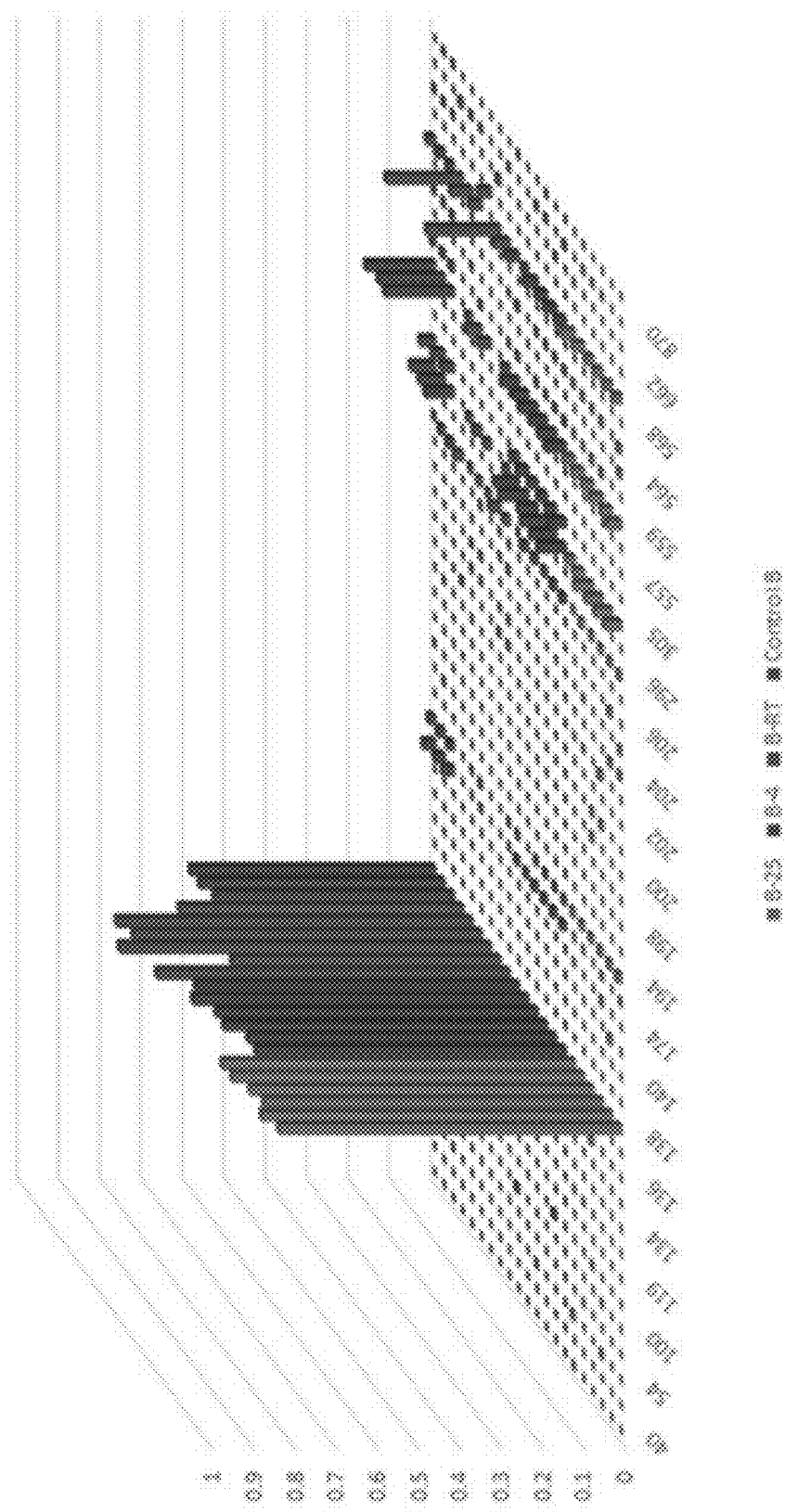
FIG. 9 shows representative data pertaining to the peak intensity profiles for the bacterial communities present in IN-M2 (B) after one month of growth at 4° C., 25° C., −80° C. (control), and room temperature.

After 1 month of growth, the bacterial community profiles of batch B stored at 4° C., 25° C., −80° C., and room temperature were all similar to each other and shared many of the same large peaks (FIG. 9). All 6 replicates from each of the 4 temperatures shared the same dominant peak at 138 base pairs. Peaks at 191, 194, 296, 305, 559 and 661 base pairs were also found in at least 5 of the replicates from each temperature. Unlike in batch A, batch B was dominated by peak 138 in all replicates and at all 4 temperatures with no other peaks coming close to the same level of intensity. There were also no observable shifts in abundance with changing temperatures. The only noticeable difference between the communities was at 508 base pairs. The peak at 508 base pairs did not have high intensity values but was only present in the control (−80° C.) and the 4° C. sample.

Fungi

IN-M1 (Batch A)

Figure 10:
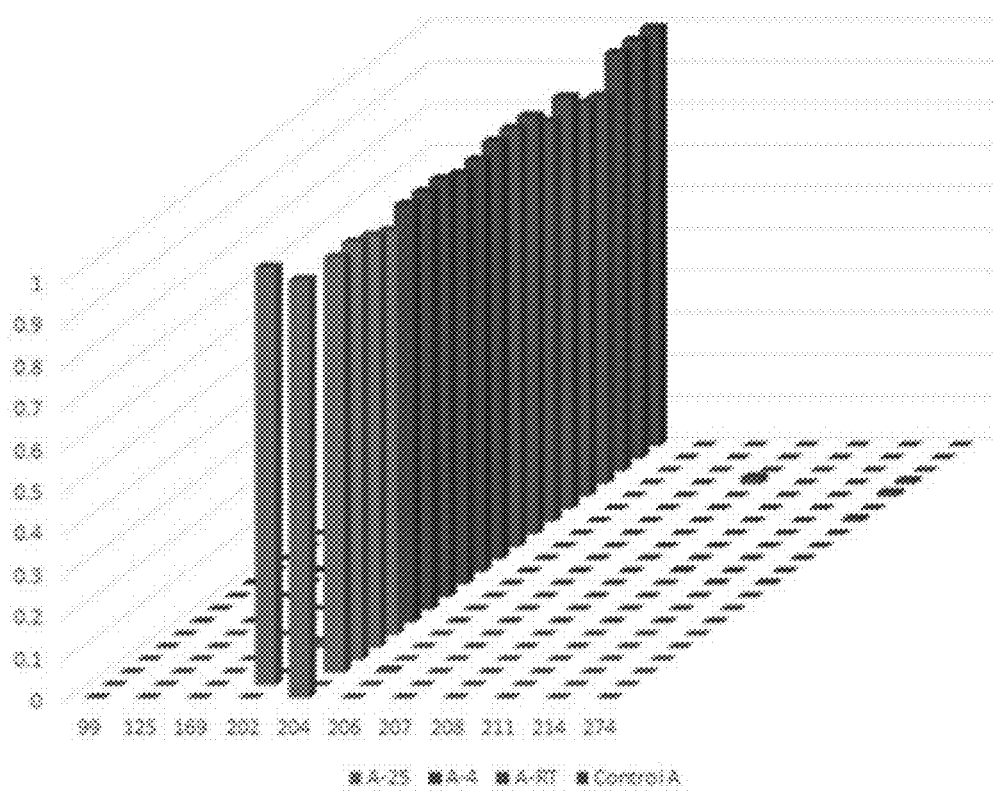
FIG. 10 shows representative data pertaining to the peak intensity profiles for the fungal communities present in IN-M1 (A) after one month of growth at 4° C., 25° C., −80° C. (control), and room temperature.

After 1 month of growth, the fungal communities present in the samples stored at all 4 temperatures were virtually identical and only had 1 or 2 large peaks (FIG. 10). A peak at 204/5/6 base pairs dominated the profile. Peaks that are only 1 or 2 base pairs different likely represent the same organism.

IN-M2 (Batch B)

Figure 11:
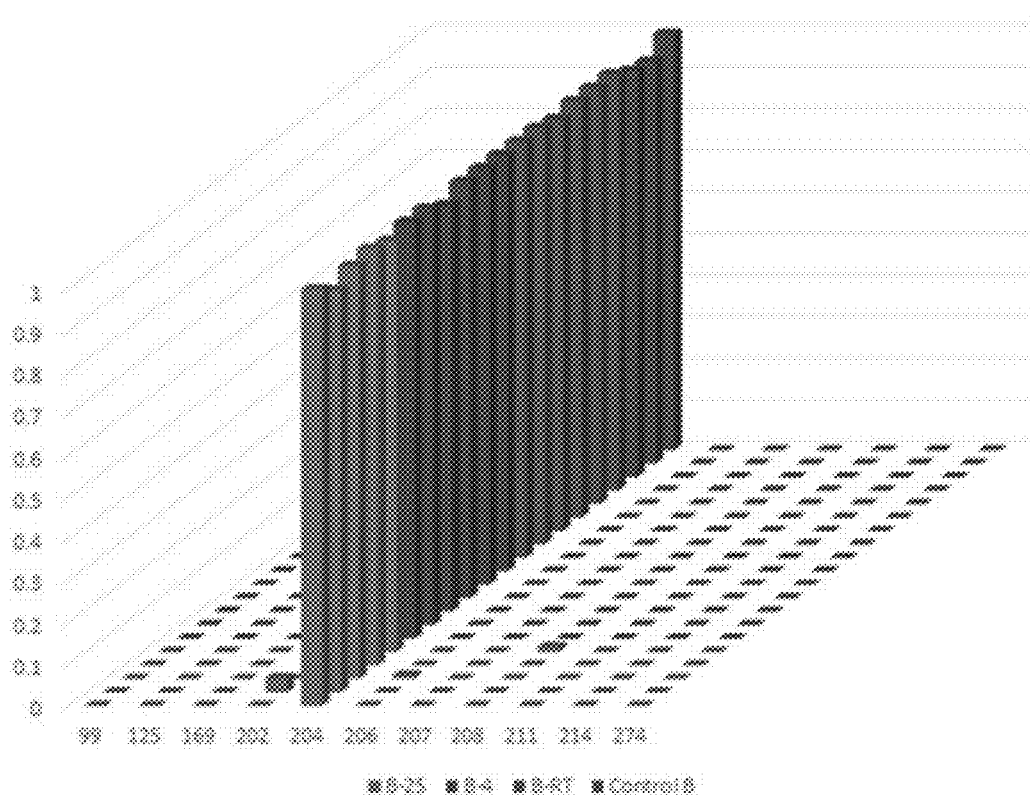
FIG. 11 shows representative data pertaining to the peak intensity profiles for the fungal communities present in IN-M2 (B) after one month of growth at 4° C., 25° C., −80° C. (control), and room temperature.

After 1 month of growth the fungal communities present in the samples stored at all 4 temperatures were virtually identical and had only 1 or 2 large peaks (FIG. 11). A peak at 204/5 base pairs dominated every profile with a very high intensity value.

The results of the fungal community profiling were consistent with the results from the time zero samples.

Without wishing to be bound by theory, the temperature at which batch A is stored may have had an effect on the bacterial community present in the product. Different organisms dominate the bacterial community of batch A depending on the temperature at which the product is stored. As the temperature increases, so does the population of the organism responsible for the peak at 138 base pairs. The increase in abundance of peak 138 appears to decrease and/or eliminate organisms as it proliferates. After 1 month of growth, the fungal communities in both batch A and B remained consistent and were dominated by 1 or 2 organisms. After 1 month, temperature did not affect the fungal community.

Example 6—Use of the Compositions and Methods with Plant Performance

Microgreens and Petite greens are young edible greens produced from various kinds of vegetables, herbs or other plants. They are harvested before they develop into larger plants and despite their small size they have intense flavour and color. There is an increasing demand for these products from upscale markets and fine dining restaurants. Arugula, a fast growing and widely consumed petite green, was selected for this study. It was planted on organic soil from the Holland Marsh as it resembles the soils used to grow these plants.

Arugula seeds and soil mixed with different concentrations of cell-free supernatant compositions made from a microbial cultures comprising IN-M1 and a microbial culture comprising IN-M2 were used. The selected treatments were based on efficacy of control found with plant pathogenic fungi: Control (n=5); ⅒ IN-M1 (n=5); 1/20 IN-M1 (n=5); 1/40 IN-M1 (n=5); ⅒ IN-M2 (n=5); 1/20 IN-M2 (n=5); and 1/40 IN-M2 (n=5).

360 g of the Holland Marsh soil (at 80% moisture holding capacity) were mixed with different concentrations of Inocucor products. Ten arugula seeds were planted into 60 g of the treated soil per pot and five pots were used per treatment (n=5). Plant emergence and growth was monitored and after two weeks plant were harvested, processed and the results analyzed.

Trial 1

Figure 12:
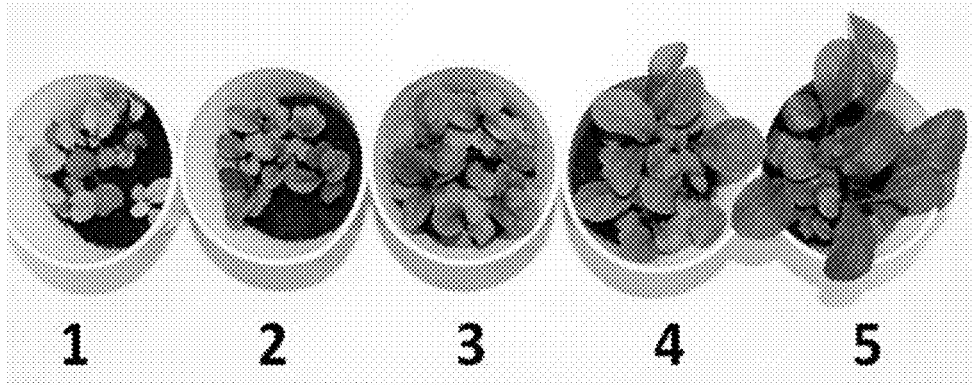
FIG. 12 shows representative data pertaining to the arugula vigor scale used as a visual way of measuring plant growth and foliage volume.
Figure 13A:
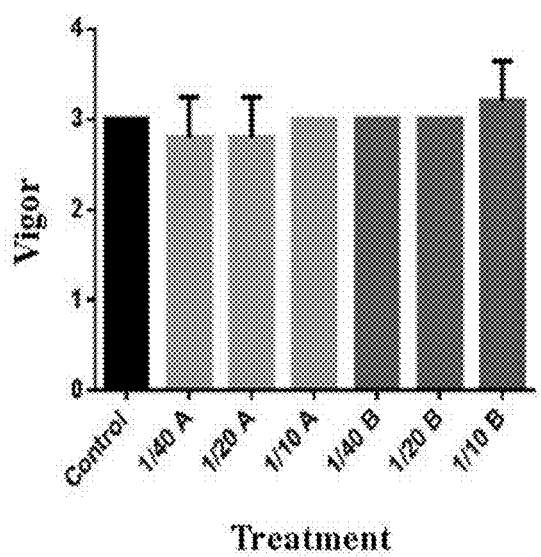
FIGS. 13A-13F show representative data pertaining to: the vigor (FIG. 13A), number of plants (FIG. 13B), chlorophyll content (FIG. 13C), shoot dry weight (FIG. 13D), root dry weight (FIG. 13E), and plant length (FIG. 13F) of the arugulas treated with IN-M1 (A) and IN-M2 (B) in Trial 1.
Figure 13B:
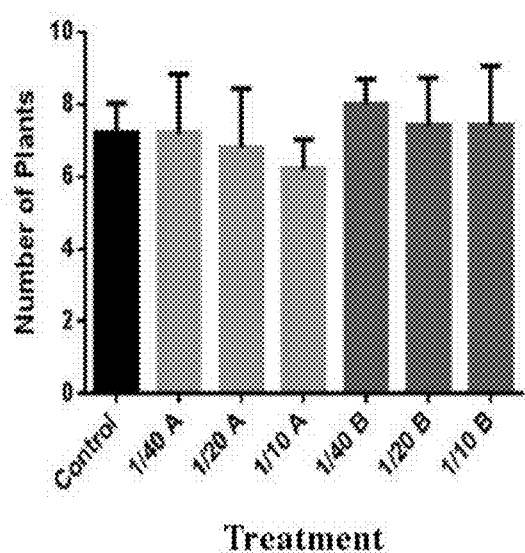
Figure 13C:
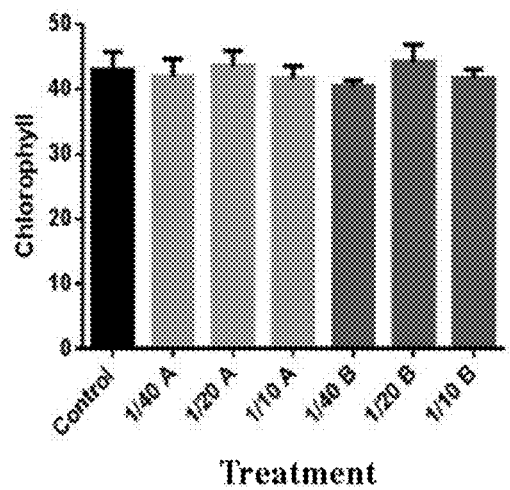
Figure 13D:
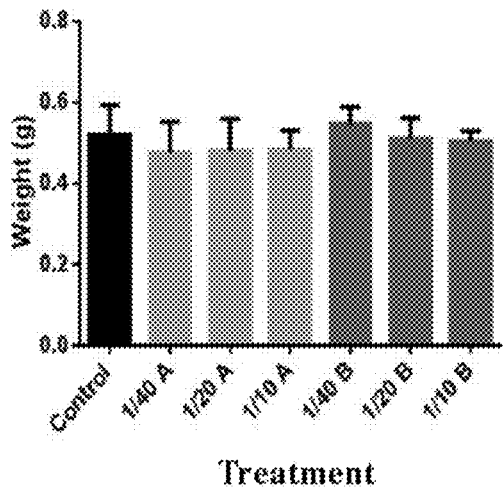
Figure 13E:
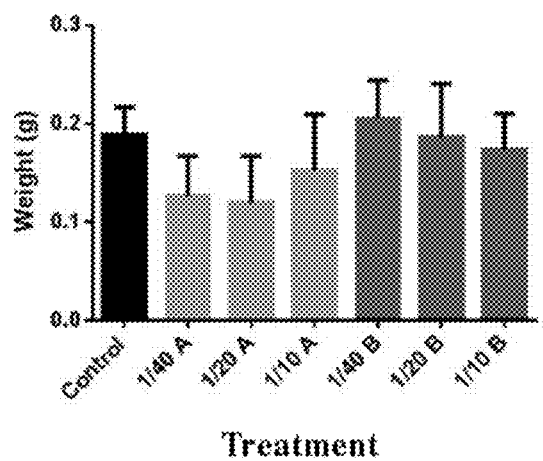
Figure 13F:
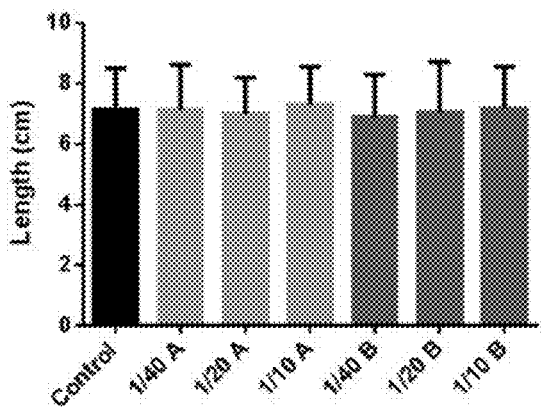
Figure 14A:
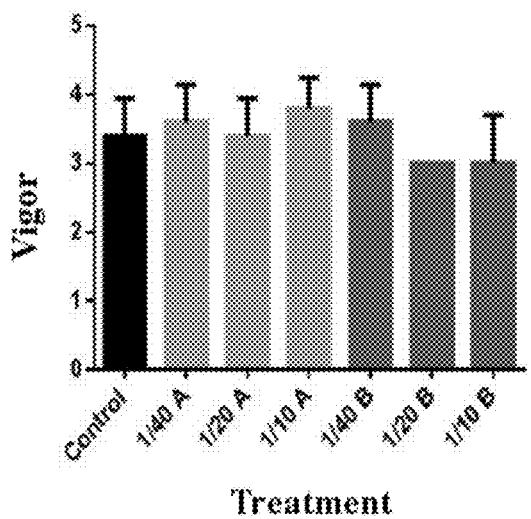
FIGS. 14A-14F show representative data pertaining to: the vigor (FIG. 14A), number of plants (FIG. 14B), chlorophyll content (FIG. 14C), shoot dry weight (FIG. 14D), root dry weight (FIG. 14E), and plant length (FIG. 14F) of the arugulas treated with IN-M1 (A) and IN-M2 (B) in Trial 2.
Figure 14B:
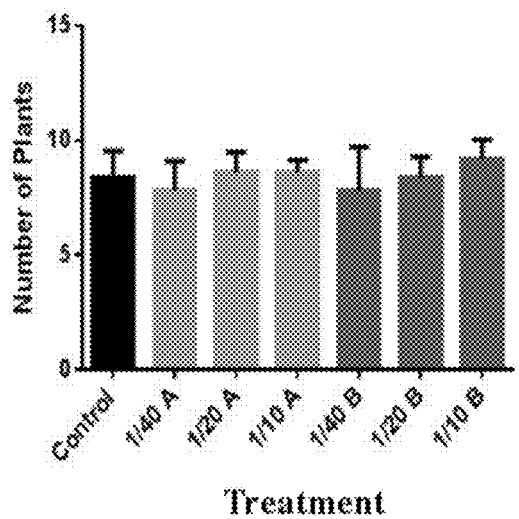
Figure 14C:
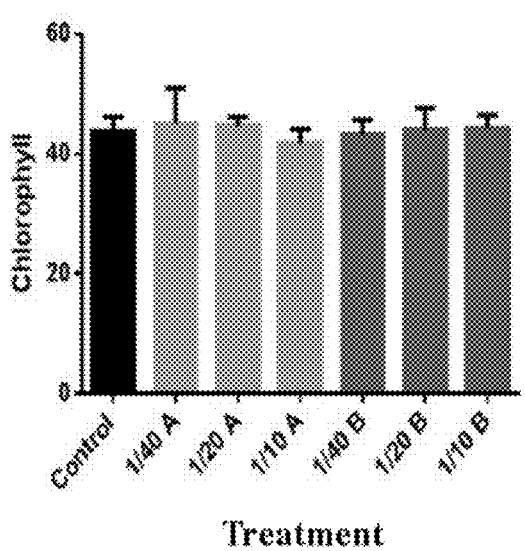
Figure 14D:
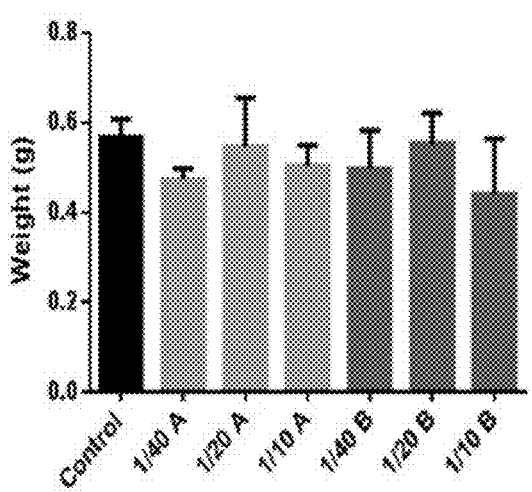
Figure 14E:
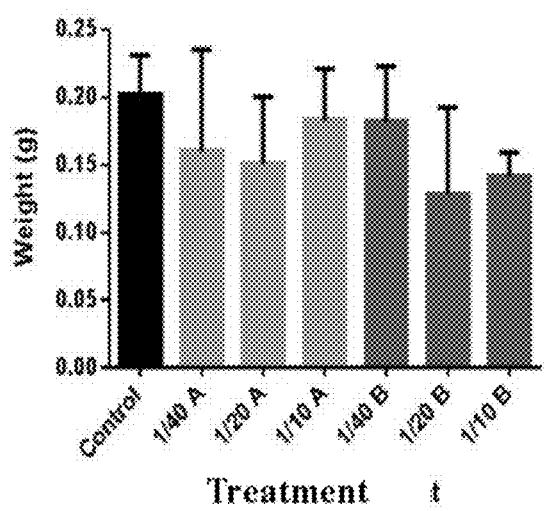
Figure 14F:
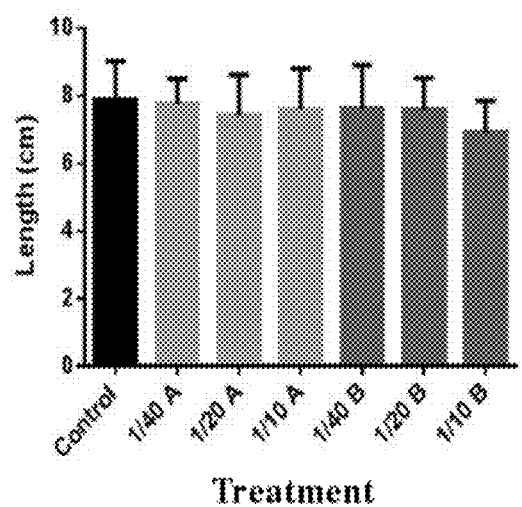

Two weeks after planting, the arugulas were processed, the number of plants was counted and the chlorophyll content, shoot length, total plant length, and total plant dry weights were measured. An arugula vigour scale was developed to use as a visual way of measuring plant growth and foliage volume (FIG. 12).

Figure 16:
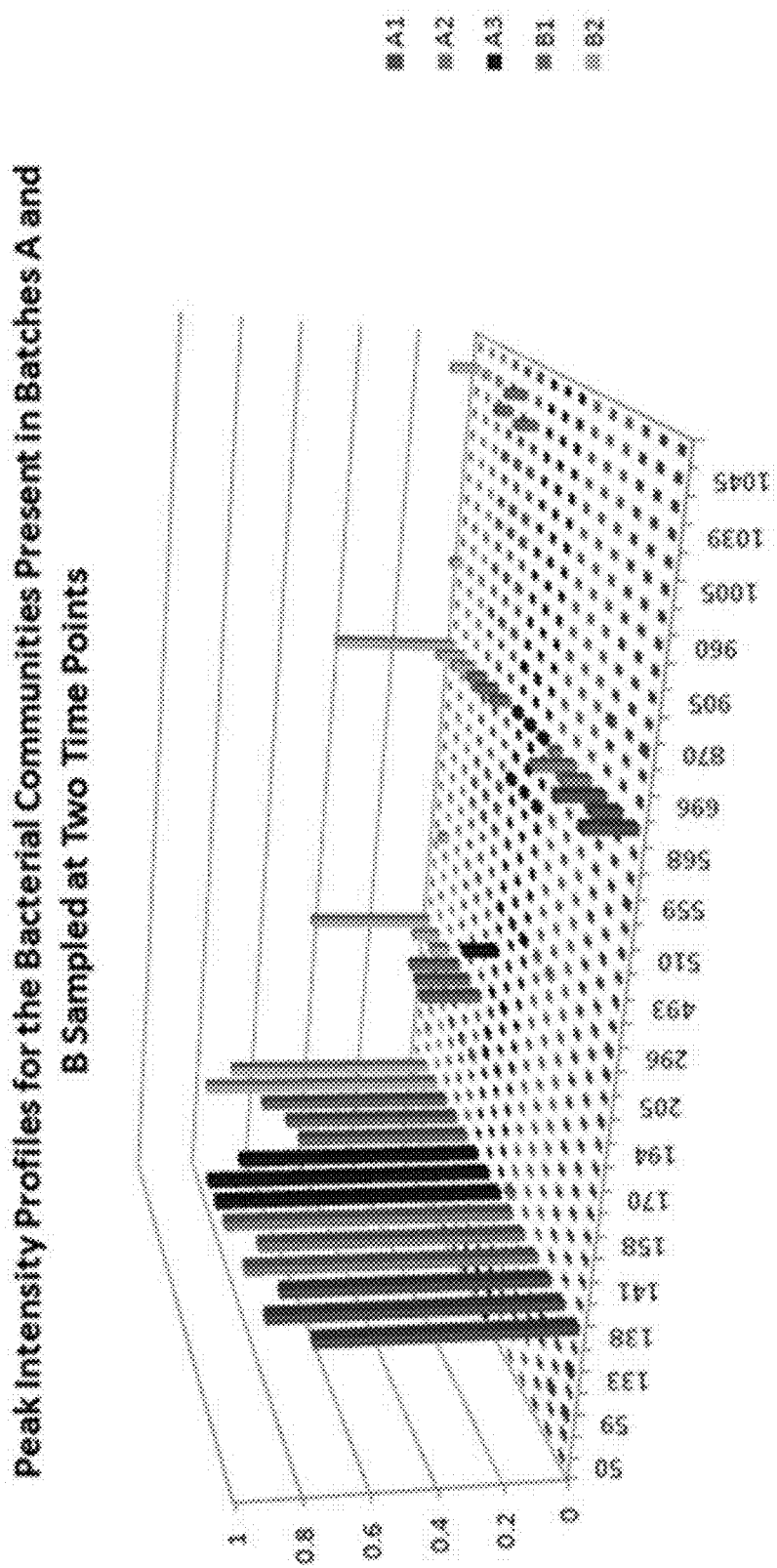
FIG. 16 shows representative data pertaining to the peak intensity profiles for the bacterial communities present in IN-M1 (A) and IN-M2 (B) at time zero sampled at two time points.
Figure 17:
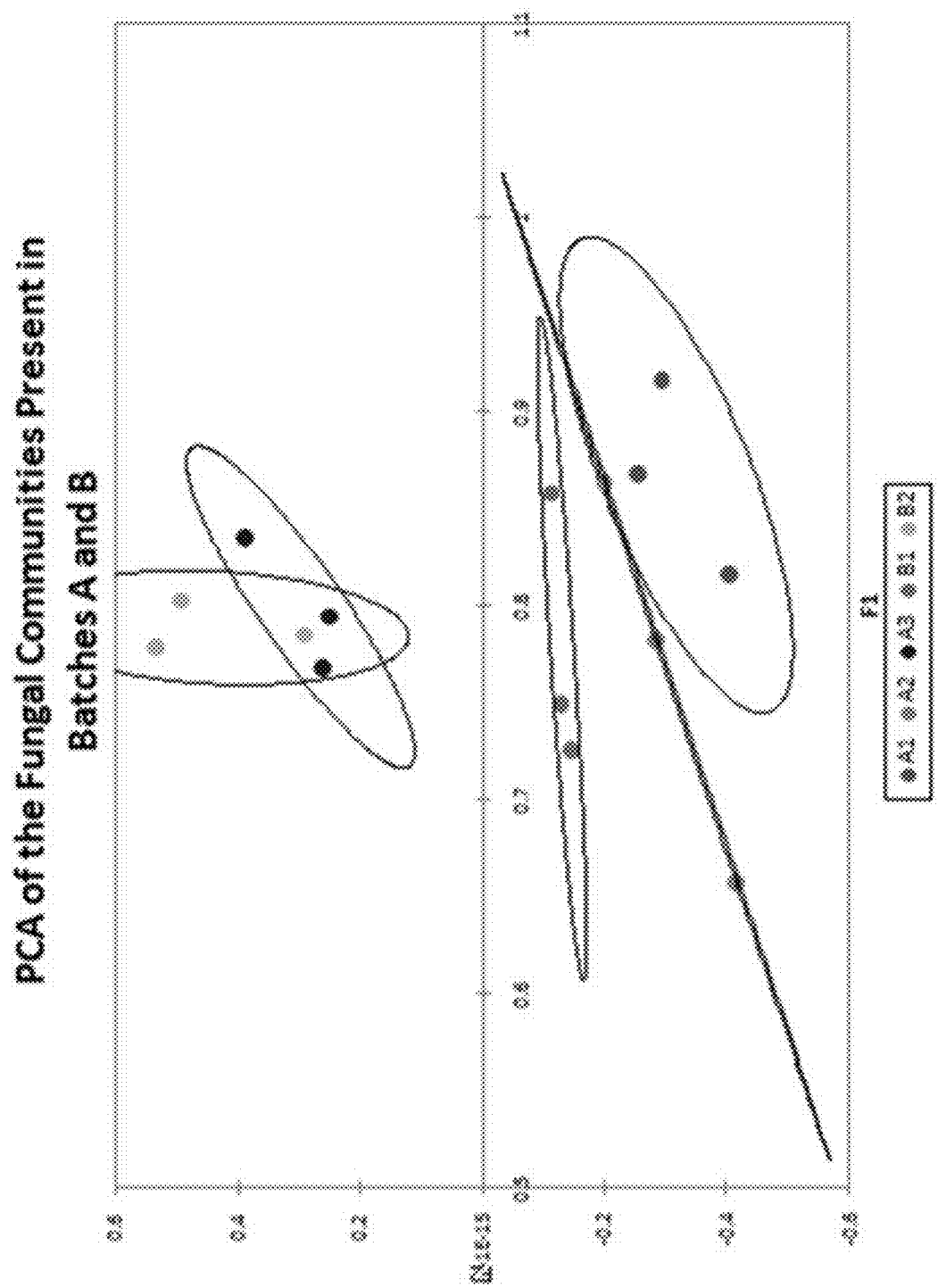
FIG. 17 shows representative data pertaining to the principle component analysis of the fungal communities present in IN-M1 (A) and IN-M2 (B) at time zero.
Figure 18:
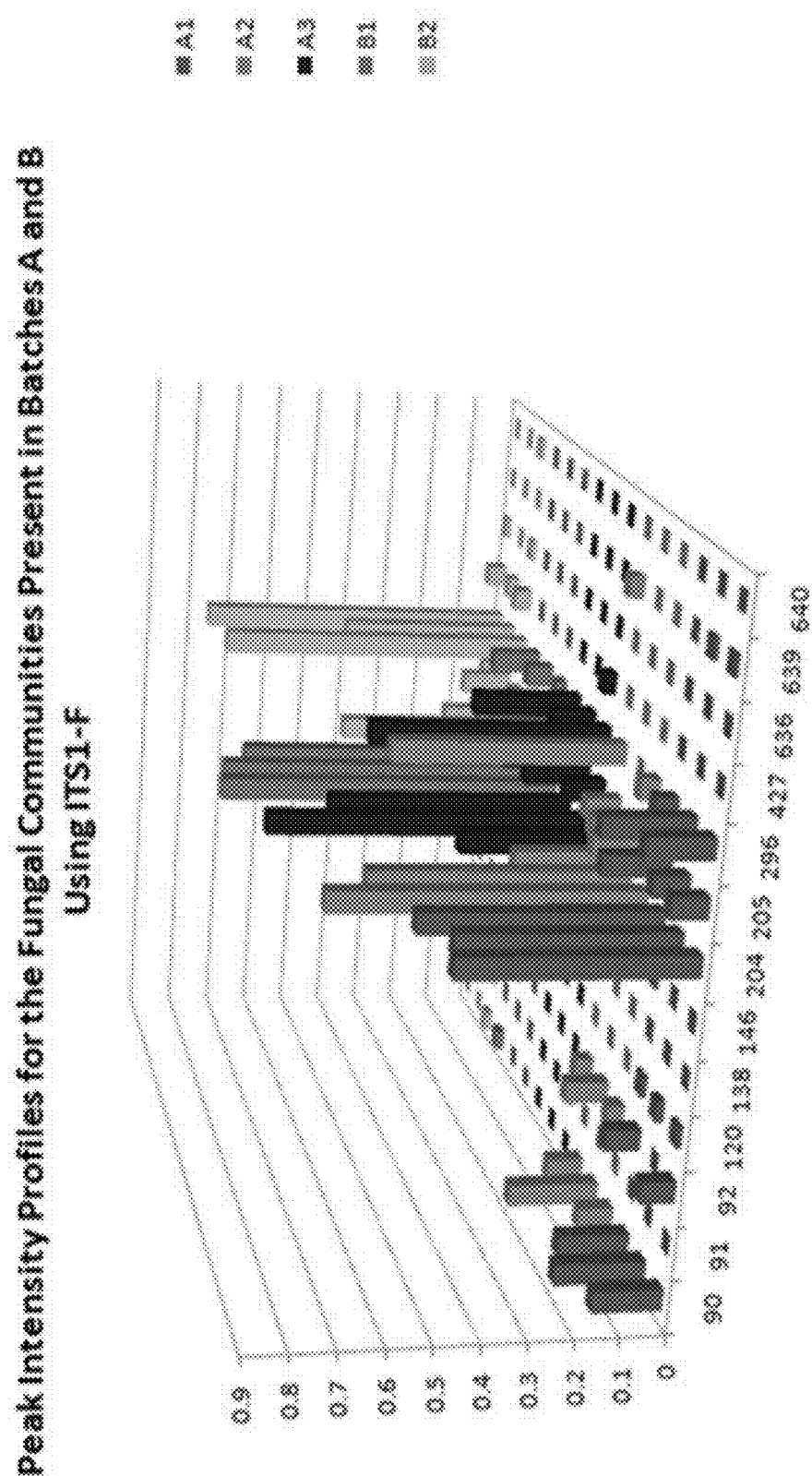
FIG. 18 shows representative data pertaining to the peak intensity profiles for the fungal communities present in IN-M1 (A) and IN-M2 (B) using ITS1-F.

Using the vigour scale the plants were rated on each pot of each treatment. As shown in FIG. 16A, there were no statistically significant differences on the vigour between any of the treatments and the control plants. Moreover, no differences were found between the treated and untreated plants in any of the parameters measured (number of plants, chlorophyll, shoot dry weight, roots dry weight, and plant length) (FIG. 13A-F). Although the differences on root biomass were not statistically significant, without wishing to be bound by theory, these results suggest that treatments with higher concentrations of IN-M1 and IN-M2 might be detrimental for root development.

Trial 2

Figure 15:
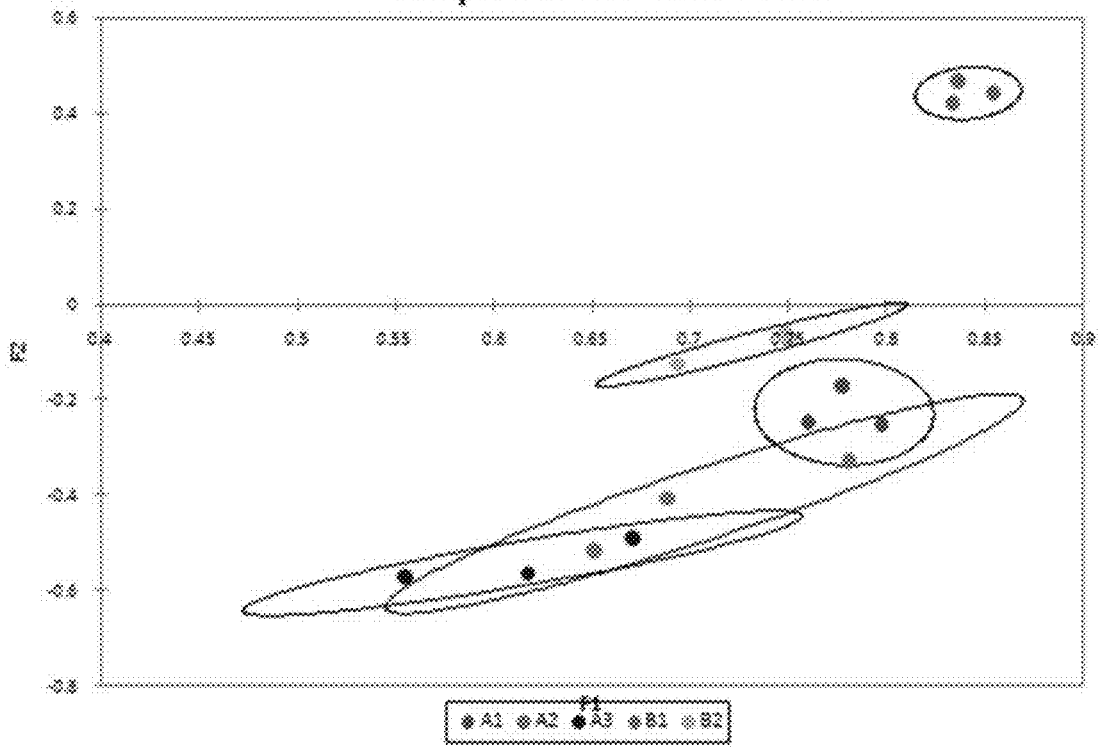
FIG. 15 shows representative data pertaining to the principle component analysis of the bacterial communities present in IN-M1 (A) and IN-M2 (B) at time zero sampled at two time points.

As described previously, two weeks after planting, the plants were rated plant vigour using the scale presented in FIG. 15. The plants were removed from their pots, and all the soil was washed off the roots for a visual comparison. The number of plants was counted, and chlorophyll content and plant length were measured before the roots and shoots were separated and dried overnight at 60° C. The dry biomass of the shoots and roots were recorded and compared separately. As shown in FIG. 14A-F, no statistically significant differences were found between control and treated plants in any of the parameters measured.

Under the conditions tested, treatments with cell-free supernatant compositions derived from a microbial culture of IN-M1 and a microbial culture of IN-M2 at dilutions of 1:10 to 1:40 did not impact arugula growth and plant performance. No statistically significant differences were found between treated and control plants.

Example 7—A Microbial Fingerprint of the Consortia Used in the Cell-Free Supernatant Compositions Microbial Analysis—TRFLP For ease of identification, the two batches of microbial cultures were labeled as batch A, IN-M1 and batch B, IN-M2. Each batch was thoroughly mixed by inverting the bottle a few times. Three 1.5 mL subsamples were taken from each bottle and placed in 2 mL microcentrifuge tubes. The tubes were placed in a centrifuge and spun at 14,000 rpm for 4 minutes to pellet any particulates and microorganisms. A DNA extraction was performed on each pellet using Norgen Genomic DNA Isolation kits (Norgen Biotek Corp. ON) following the manufacturer's protocol.

A PCR master mix was made with a final reaction volume 50 µL. The two primers that were used in the bacterial PCR were 63F primer with sequence CAGGCCTAACACATG-CAAGTC (SEQ ID NO:1) and 1389R primer with sequence ACGGGCGGTGTGTACAAG (SEQ ID NO:2). The two primers used in the fungal PCR were ITS1F with primer sequence TCCGTAGGTGAACCTTGCGG (SEQ ID NO:3) and ITS4 with primer sequence TCCTCCGCTTATTGA-TATGC (SEQ ID NO:4). A 1% agarose gel was run to check the reaction products. The PCR products were purified using a DNA clean and concentrator (Zymo Research Corporation, Irvine, Calif., USA). 12 µL of purified PCR product was added to 13 µL of restriction mixture and incubated in darkness at 35° C. for 3 hours before sequencing gel analysis using a 3730 DNA Analyzer alongside GeneScan 1200 LIZ Size Standards (Applied Biosystems, USA). TRFLP results were analyzed using Gene Marker (SoftGenetics LLC) with default settings and a modified fragment peak intensity cut-off of 50. The forward and reverse fragment size plus intensities were exported to Microsoft Excel and the data analyzed using PCA with the software, XLStat. TRFLP data are transformed into binary and clustered on the basis of similarity of peak presence. 95% confidence intervals were automatically drawn around each treatment group where statistical significance is discerned. Groups that do not overlap were considered statistically different in their microbial community.

Plating and Isolate Identification

Subsamples from each batch were plated on 7 different media types to determine what microbes were present in each batch and to identify any changes to the consortia or new microbes.

The media used included nutrient agar (NA), potato dextrose agar (PDA), tryptic soy agar (TSA), LB agar (LB), clostridial media (RCM), King media, and MRS agar. Media was prepared as per manufacturer recommendations and poured into pre-sterilized plastic petri dishes with an 85 mm diameter.

Serial 10-fold dilutions up to $10^{-6}$ were prepared for both batches A and B. Duplicates plates inoculated with 100 µL of solution were prepared for each media type with water serving as the control. The plates were then stored in a 25° C. incubator and checked daily for growth. Plates were kept in the incubator for up to 10 days to ensure that any slow growing organisms were not missed.

Individual colonies from each media type were selected based on morphology and isolated by streaking onto a new plate. Isolates were re-streaked and isolated 3 times to ensure that a pure culture was obtained.

Identification of the bacteria by amplification and sequencing of 16S rRNA

DNA was extracted from each strain by taking a 1 µL loop of bacteria from the plate and placing it into a 1.5 mL microcentrifuge tube containing 0.5 mm glass beads and 150 µL sterile water. The tubes were placed in boiling water for 10 minutes. Following heating, the tubes were placed in a bead beater for 2 minutes and then centrifuged at 14,000 rpm for 2 minutes. The supernatant containing the DNA was then used as the template for the polymerase chain reaction (PCR). Amplification of 16S rRNA was performed in a 50 µL final volume containing the primer pair 27F, AGAGTTT-GATCCTGGCTCAG (SEQ ID NO:5) and 1492R, GGT-TACCTTGTTACGACTT (SEQ ID NO:6). A 1% agarose gel was run to check the reaction products. The PCR products were purified using a DNA clean and concentrator (Zymo Research Corporation, Irvine, Calif., USA).

TABLE 1

| Potential Match | # of Isolates | 63F Fragment | 1389R Fragment |
|---|---|---|---|
| Bacillus megaterium | 2 | 538 | 296 |
| Acetobacter peroxydans | 7 | 138 | 296 |
| Bacillus subtilius | 6 | 201 | 296 |
| Lactobacillus paracasei | 4 | 558 | 296 |
| Lactobacillus casei | 2 | 558 | 296 |
| Lactobacillus spp. | 10 | 558 | 296 |

Example 8—Use of Cell-Free Supernatant Compositions to Promote Soybean Seed Germination Microbial cultures comprising IN-M1 or IN-M2, and their cell free supernatant (CFS) compositions were evaluated at various dilutions (1/25, 1/50, 1/100, and 1/1000) on soybean seed germination under optimal and salinity stress conditions. The experiment was conducted in petri dishes containing 2 filter papers (Whatman #8, Fisher Scientific, Canada) and 7 mL solution was used in each per petri plate. Cell-free supernatant (CFS) composition was obtained by centrifuging the microbial culture for at least 10 minutes at 13,000 rpm. The CFS composition was then removed via pipette or decanting and filter sterilized to remove any possible bacterial cells in the supernatant. Various dilutions of the microbial culture and its CFS composition were prepared in sterilized distilled water (optimal condition experiment) or 100 mM saline solution (salinity stress condition). There were 10 uniform soybean (RR2Y) seeds in each petri dish. The plates were incubated at temperature 22±1° C. In case of salinity experiment, the microbial culture and its CFS composition were diluted in saline solution (100 mM NaCl).

It should be noted that while all seeds able to germinate will probably germinate eventually in the near optimal conditions of the assay. However, under field conditions the situation is very different. The field environment is complex, involving a much wider range of stresses and various soil life forms (insects, fungi, bacteria); without wishing to be bound by theory, slower emergence for a seeded crop means fewer seedlings will emerge. This results in a smaller population (stand count) and many agronomic studies have shown that there is a general correlation between stand count and final yield. If conditions during the growing season are near perfect a crop with an initially low stand count may be able to compensate for this and make up the difference by the end of the season. However, a "normal" year is not near-perfect and a smaller initial stand will likely lead to a smaller yield.

Cell-free Supernatant Compositions

No Stress (Optimal) Conditions

Figure 19:
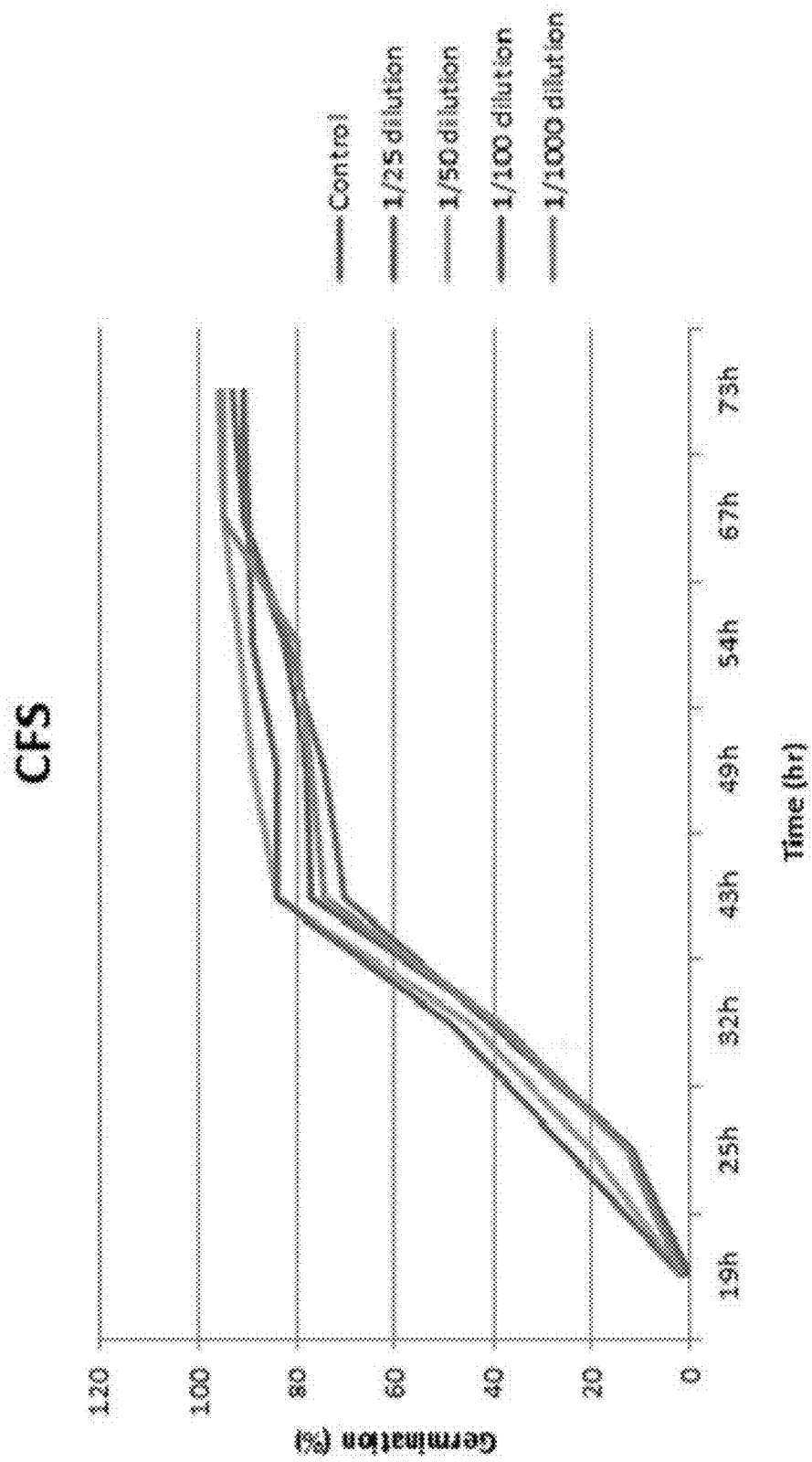
FIG. 19 shows representative data pertaining to the effect of various dilutions of liquid product without microorganisms on soybean seed germination under optimal conditions.

1/100 and 1/50 dilution of cell-free supernatant compositions from each of IN-M1 or IN-M2 microbial cultures showed more rapid germination rate throughout the experiment until 67 hours, reaching as much as 15% at 40 hours (FIG. 19). The biological effect appears to be dilution-dependent; that is, the effect is optimum between 1/100 and 1/50 and less at the lower dilution 1/25 and the higher dilution 1/1000.

Salt Stress Conditions (100 mM NaCl)

Figure 20:
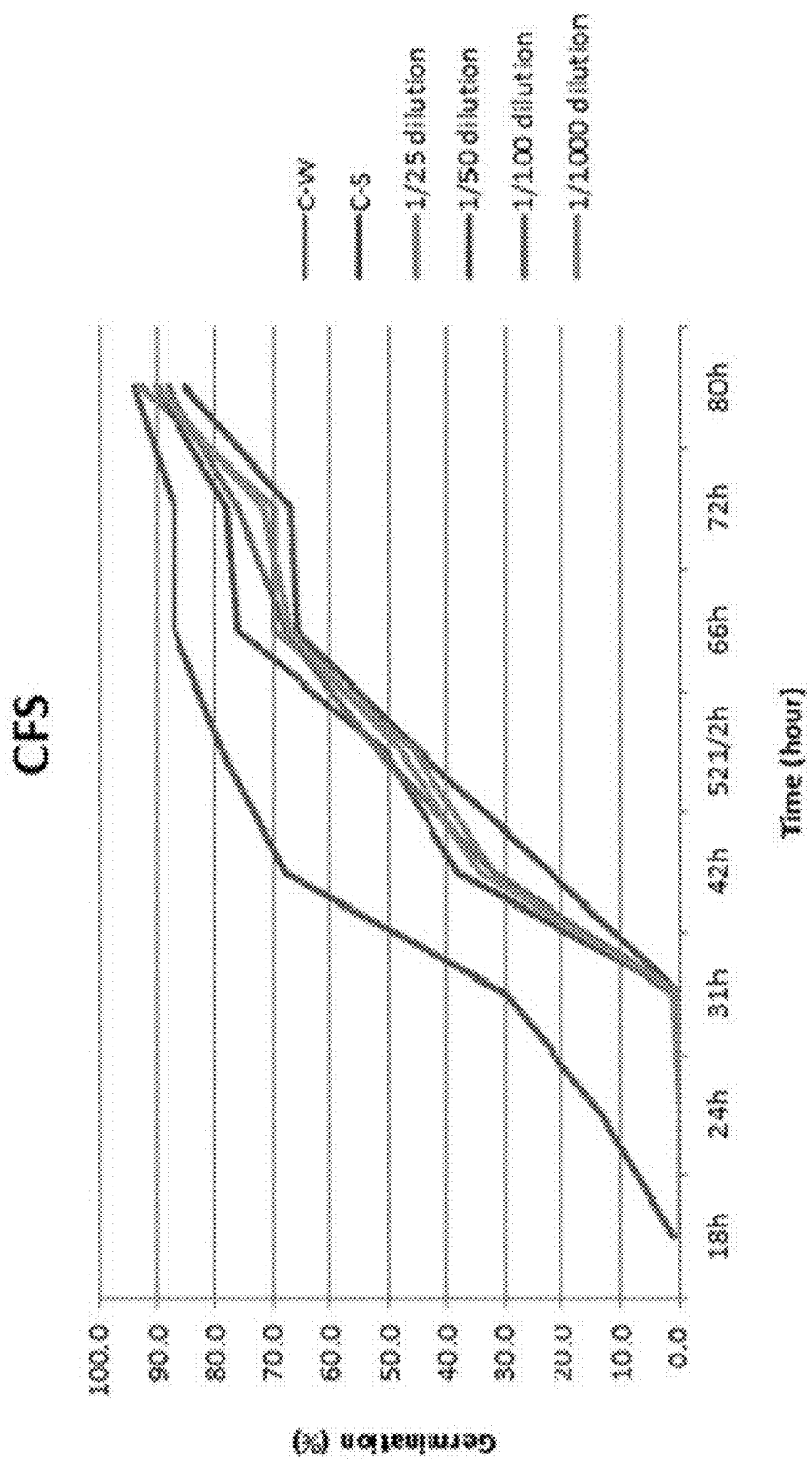
FIG. 20 shows representative data pertaining to the effect of various dilutions of liquid product without microorganisms on soybean seed germination under salt stress conditions.

Under salt stress conditions, stressed seeds treated with IN-M1 or IN-M2 microbial culture derived cell-free culture showed a similar delay in germination rate up to 31 hours (FIG. 20). Thereafter all dilutions of the cell-free supernatant compositions showed an initial increase in germination rate over the Salt Stress Control (red: C-S) which is maintained throughout the experiment; the major difference being seen using a 1:50 dilution similar to the unstressed samples above.

Microbial Culture Composition

No Stress (Optimal) Conditions

Figure 21:
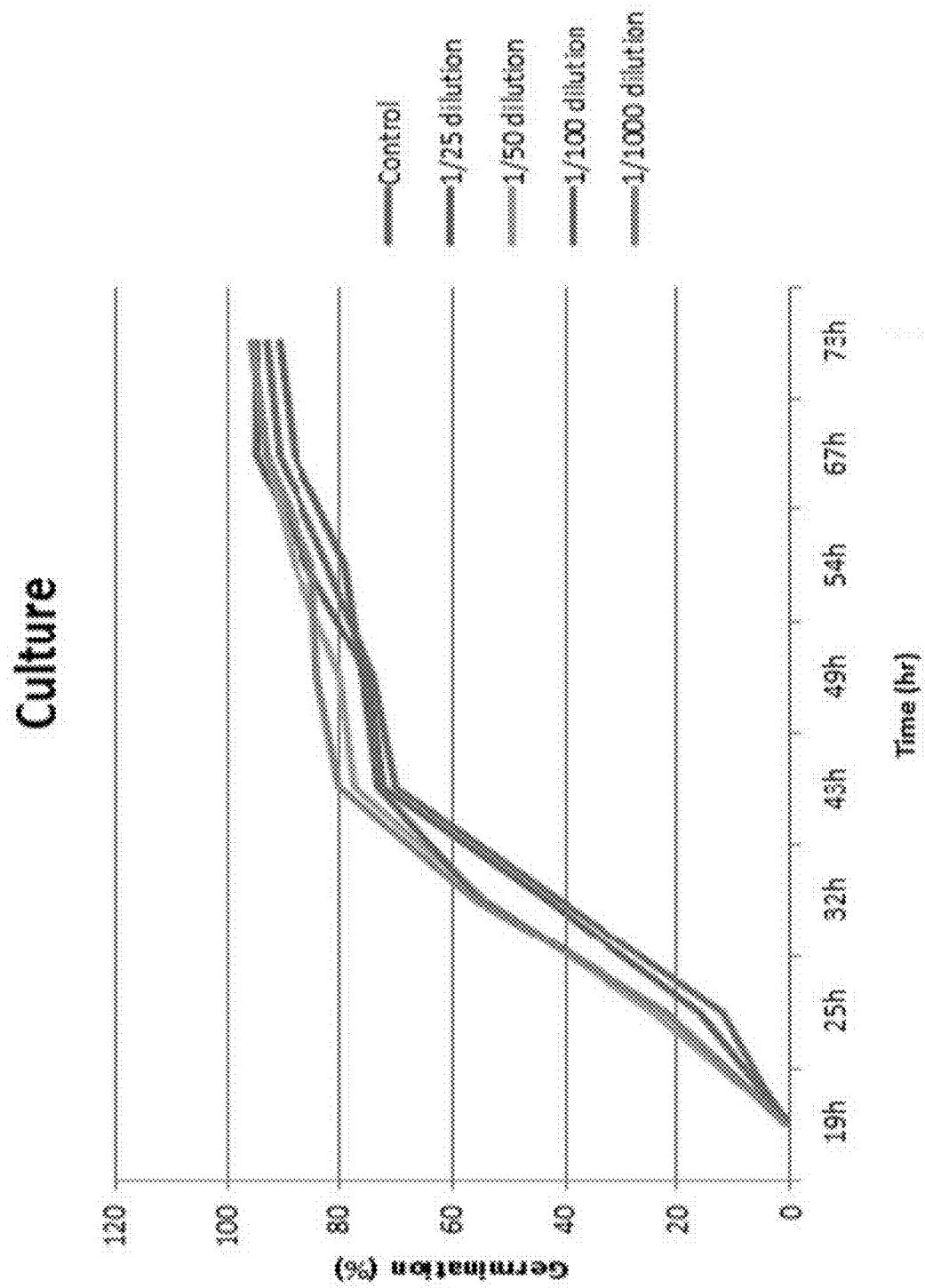
FIG. 21 shows representative data pertaining to the effect of various dilutions of IN-M1 on soybean seed germination under optimal conditions.

1/1000, 1/100, and 1/50 dilution of the microbial culture from IN-M1 or IN-M2 treated seeds show a more rapid germination rate from the beginning of the experiment, reaching approximately a 15% increase at 30 hours (FIG. 21).

Salt Stress Conditions (100 mM NaCl)

Figure 22:
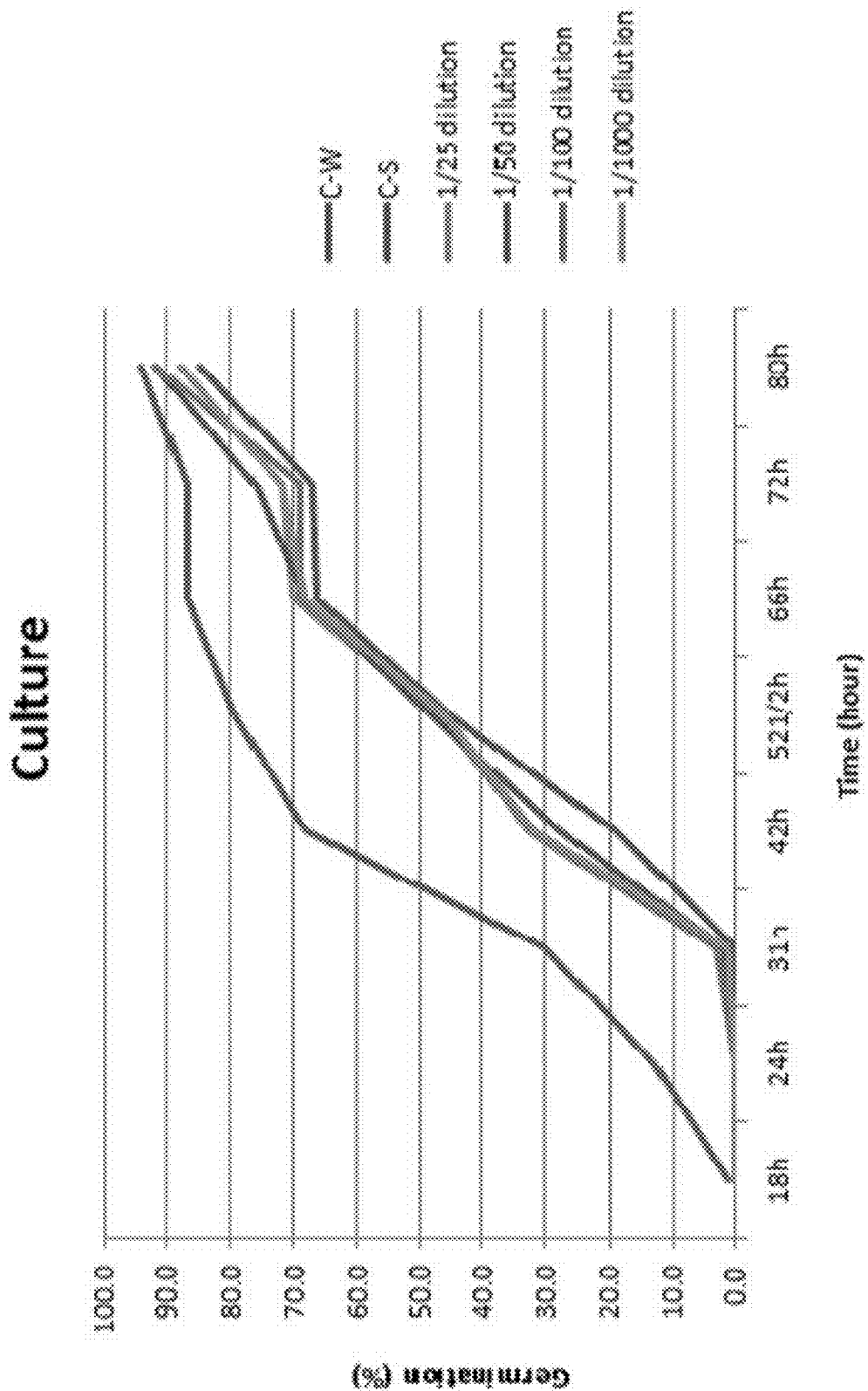
FIG. 22 shows representative data pertaining to the effect of various dilutions of IN-M1 on soybean seed germination under salt stress conditions.

Samples treated with IN-M1 or IN-M2 microbial culture (including microorganisms) showed a similar delay in germination rate up to 31 hours; thereafter all dilutions showed an initial increase in germination rate over the Salt Stress Control (FIG. 22).

In summary, a dose dependent increase of 15-20% was observed in seed germination rate in soybean; this increase was also present under stress conditions. Turf grass seedlings treated once at planting exhibited 20-30% increased early biomass at 3-4 weeks without fertilizer, demonstrating vigor (robustness) in early shoots after germination in soil. A dose dependent effect on germination rate of 15% over 67 hours was observed under induced abiotic stress laboratory conditions in the cell free broth.

The data further show that the biostimulation effect can be associated with discrete time periods of germination activity. For example, these data show that under the conditions examined, there is an initial peak or surges of biostimulation activity on germination at about 24 hours after the initiation of the germination study, and then a second peak or surge of biostimulation activity on germination at about 30-36 hours when the germination study is carried out under optimal conditions. When the germination study is carried out under stress conditions, e.g., 100 mM NaCl, the second peak of germination activity is shifted to about 42-48 hours. The presence of the foregoing peaks or surges of germination activity are observed in a germination study as described herein is correlated with specific outcomes in plants. Thus, a CSF composition was associated with two peaks or surges of germination activity, when germination activity is assayed as described herein, then the following is observed when the CSF composition is utilized with growing plants such as soybean and corn:

1. Increased biomass in plants grown in greenhouse or in a laboratory;
2. Increased leaf area (about 10-15%) in plants grown either in the greenhouse or in field tests; and
3. Increase in dry weight of leaves (about 10-15%), i.e., an increase in cell mass, harvested from plants grown in the greenhouse or in field tests.

Accordingly, the in vitro or petri-dish assay method of germination activity can be used to assess a CSF composition for desired biostimulatory activities as described herein. Specifically, functional activity "peaks" of germination activity that occur at defined times post-application of the CSF from the secondary fermentation to the seeds, e.g., soybean seeds in a test batch of about 100 seeds, are correlated with biostimulatory activities in the plants to which the CSF is applied, e.g., increase in leaf biomass, leaf area, and shoot biomass.

Example 9—Reduction of the Carbon Footprint of Grasses

In urban and suburban environments the functional soil-vegetation system plays a decisive role on both the global and urban climate scales by exchanging greenhouse gases, energy, and particulates with the atmosphere. Field studies on grasses have been carried out on turf on golf courses and residential lawns. Without wishing to be bound by theory, these data suggest that when a cell-free supernatant composition is added to a sustainable turf management program the greens man or landscaper can lower the amount of synthetic fertilizer by as much as 50% over 3 years without sign of nutrient stress. The following experiment was designed in order to verify if it is possible to reduce the carbon footprint of lawns and golf courses without sacrificing seed germination rate or robustness (biomass) of the turf.

Figure 23:
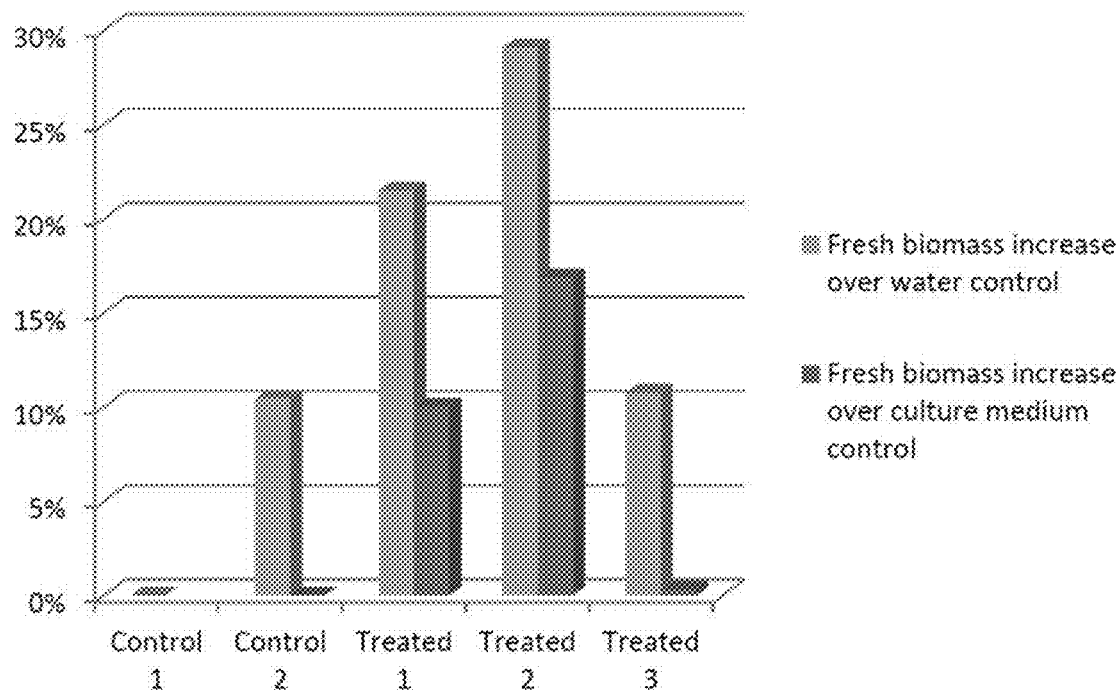
FIG. 23 shows representative data pertaining to the effect of IN-M1 on Agrostide (bent grass) grown in standard garden soil.

Each sample pot was synchronized by cutting to 4 cm and harvested one week later using scissors to cut the grass grown since the 4 cm level. The grass from 10 pots was harvested and weighed and an average wet weight calculated. Table 2 shows Agrostide (bent grass) grown in standard garden soil. A single treatment with a cell-free supernatant composition prepared from a microbial culture comprising IN-M1 increased the 6 week seedlings' wet biomass measured 21% compared to the water control and 10% compared to the culture medium (FIG. 23). Two IN-M1 treatment seedlings demonstrated a decrease in wet biomass compared to seedling sample 2 of 8% compared to the water control and 17% in the culture medium calculation over the 6 week period. Three IN-M1 treatment seedlings maintained an elevated wet biomass of 29% compared to the water control and 17% compared to the culture medium over the 6 week period.

TABLE 2

| Agrostide | Fresh biomass increase over water control (%) | Fresh biomass increase over culture medium control (%) |
|---|---|---|
| Control 1 (water) | 0 | |
| Control 2 (culture medium) | 10 | 0 |
| Treated 1 (one treatment) | 21 | 10 |
| Treated 2 (3 treatments over 6 weeks) | 29 | 17 |
| Treated 3 (2 treatments over 6 weeks) | 11 | 0 |

Figure 24:
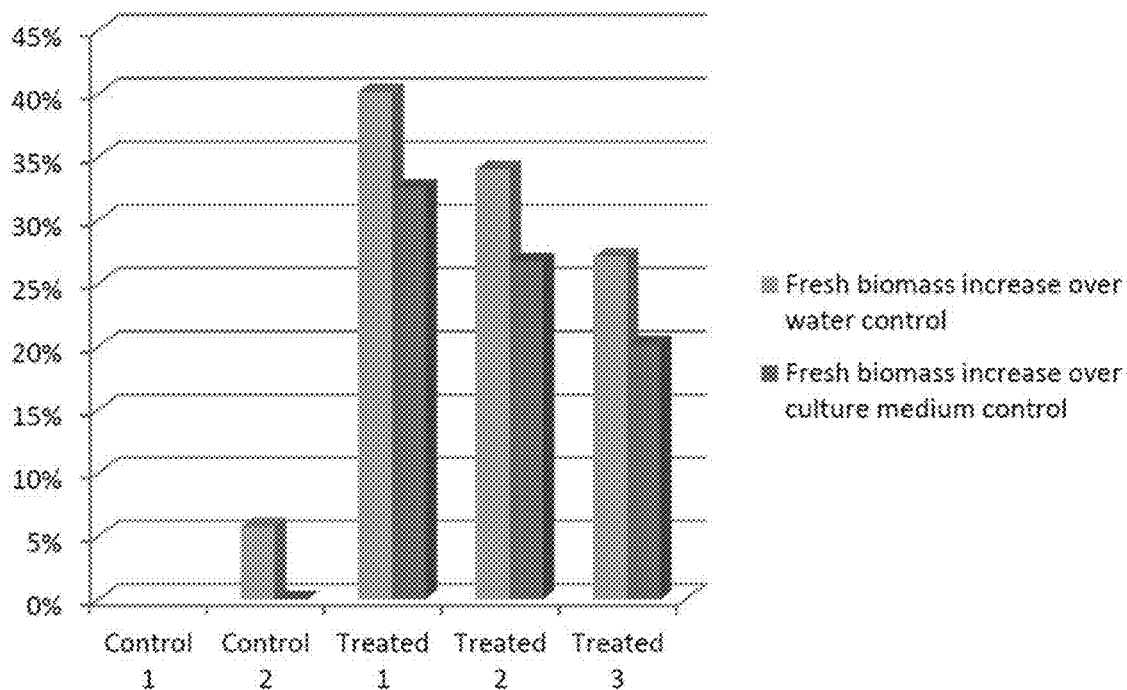
FIG. 24 shows representative data pertaining to the effect of IN-M1 on Agrostide (bent grass) grown in garden soil with additional fertilization of organic matter mixed in the soil.

Table 3 shows Agrostide when grown in garden soil with additional fertilization of organic matter mixed in the soil. A single treatment with a cell-free supernatant composition prepared from a microbial culture comprising IN-M1 increased the 6 week seedlings' wet biomass measured 40% compared to the water control and 33% compared to the culture medium (FIG. 24). Three IN-M1 treatment seedlings demonstrated a decrease in wet biomass of 6% compared to each of the control samples over the 6 week period. Two IN-M1 treatment seedlings demonstrated a decrease in wet biomass compared to seedling sample 2 of 7% compared to each of the control samples over the 6 week period.

TABLE 3

| Agrostide (soil + organic material) | Fresh biomass increase over water control (%) | Fresh biomass increase over culture medium control (%) |
|---|---|---|
| Control 1 (water) | — | — |
| Control 2 (culture medium) | 6 | 0 |
| Treated 1 (one treatment) | 40 | 33 |
| Treated 2 (3 treatments over 6 weeks) | 34 | 27 |
| Treated 3 (2 treatments over 6 weeks) | 27 | 20 |

Figure 25:
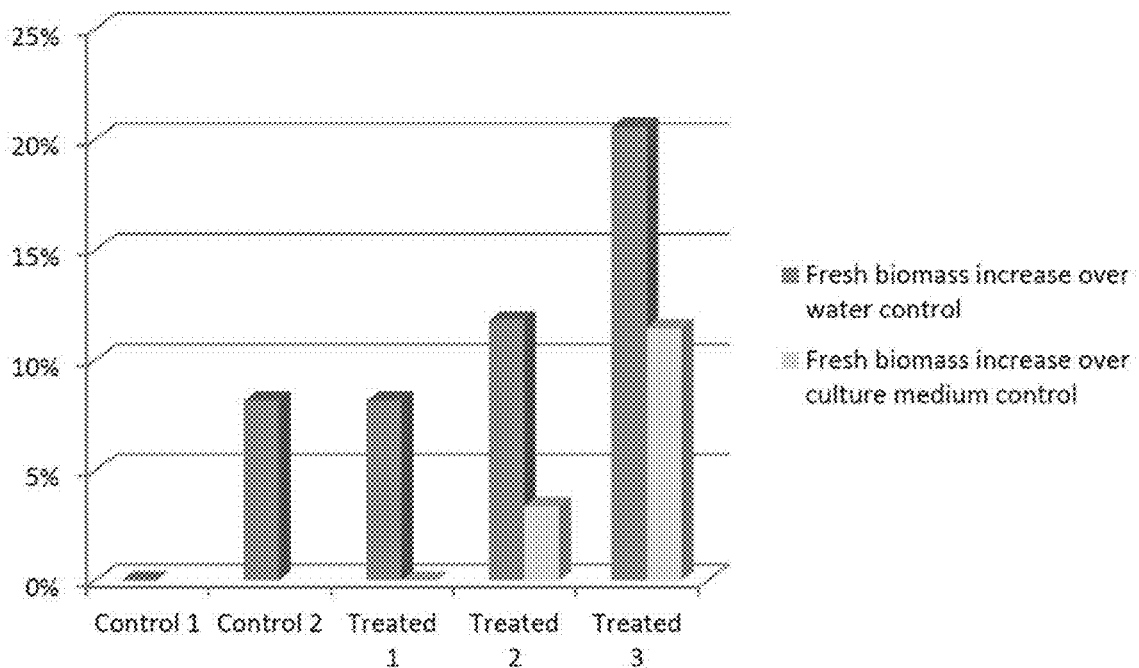
FIG. 25 shows representative data pertaining to the effect of IN-M1 on Poa parturin grown in standard garden soil.

Table 4 shows a second grass species (Poa parturin) grown in standard garden soil in order to observe if the results are similar for two different grass species. A single treatment with a cell-free supernatant composition prepared from a microbial culture comprising IN-M1 showed a wet biomass increase of 8% which is equivalent to the increase observed in Control 2, the culture medium, compared to water only (FIG. 25). Three IN-M1 treatment seedlings demonstrated an elevated wet biomass of 12% compared to the water control and 3% compared to the culture medium over the 6 week period. Two IN-M1 treatment seedlings continued to demonstrated an increase in wet biomass of 9% compared to seedling sample 2 (3 treatments) compared to the water control and 8% in the culture medium calculation over the 6 week period.

TABLE 4

| Parturin | Fresh biomass increase over water control (%) | Fresh biomass increase over culture medium control (%) |
|---|---|---|
| Control 1 (water) | — | — |
| Control 2 (culture medium) | 8 | |

TABLE 4-continued

| Parturin | Fresh biomass increase over water control (%) | Fresh biomass increase over culture medium control (%) |
|---|---|---|
| Treated 1 (one treatment) | 8 | 0 |
| Treated 2 (3 treatments over 6 weeks) | 12 | 3 |
| Treated 3 (2 treatments over 6 weeks) | 21 | 11 |

These studies were on seedlings from seeding to 6 weeks old and therefore reflected treatment with IN-M1 on plants during germination and the first 6 weeks of growth. The results in Table 2 confirmed the original laboratory observation of increase in biomass development in Agrostide (bent grass) when seeded in garden soil without fertilizer but treated with a cell-free supernatant composition prepared from a microbial culture comprising IN-M1.

Biomass development may be species specific (see Tables 2 and 4). Specifically, three treatments during 6 weeks with no synthetic fertilization at this stage of seedling development in Agrostide appear to maintain an increase in biomass development. In Poa parturin (Kentucky Blue Grass), two treatments during 6 weeks with no synthetic fertilization at this stage of seedling development seems to show the most biomass development.

Without wishing to be bound by theory, these data suggest that the early development of seedlings and shoots is robust and not affected by the lack of chemical fertilizers. However, the experiment results (Table 3) indicate that if additional organic fertilizer is added the biomass development is increased and maintained during 6 weeks. These results are in young seedlings and may not verify field results that a decrease (20-50%) in fertilizer does not affect vitality of established mature turf. Without wishing to be bound by theory, these results suggested that grass seedlings from 2 turf grass species grown in standard garden soil mix were able to germinate and demonstrated a robust shoot development without the use of synthetic chemical fertilizers.

Wheat, corn, and rice, all of which are grasses, are major sources of food worldwide. The use of chemicals and pesticides has a considerable impact on carbon emissions. Additionally, switch grass and other biofuel feedstock grasses, including corn, need to be grown with little carbon footprint in order to make the change from fossil fuels meaningful. Without wishing to be bound by theory, these data suggest that despite the lack of chemical fertilizers, a positive effect on the germination and early shoot development of 2 turf grass species.

Example 10—Increase in Biomass Development

A controlled experiment was initiated at the start of the planting season in Summerville, S.C. (Mar. 29, 2013), comparing the effect on Swiss Chard growth utilizing a cell-free supernatant composition prepared from a microbial culture comprising IN-M1. Swiss Chard seeds (25×2) were planted in community pots for germination. The control plants were fertilized with 20-20-20 fertilizer only; the test group was treated with 20-20-20 fertilizer as well as being watered in with IGS.

The seedlings were transplanted to garden soil beds, 6 days after seeding on Apr. 4, 2013. On transplantation the roots of the IGS seedlings were dipped in a 1:50 in water dilution of GS; the planting hole was also treated with the same product dilution. The two groups were planted side by side.

Following transplantation the plants were watered approximately once per week as needed. At this time, the IN-M1 test plants were watered with a spray of IGS at a 1 to 100, product to water ratio.

Five plants were measured an average height and width of the plants was recorded. The a cell-free supernatant composition prepared from a microbial culture comprising IN-M1 treated plants showed significantly more robust growth. Table 5 shows the average measurements taken on the day of transplantation (6 days after seeding), 15 and 40 days after seeding, indicated that while the control group plants measured an average of 12 inches in height and 15 inches in width, the IN-M1 treated plants averaged 20 inches high and 25 inches wide at 40 days after seeding.

TABLE 5

| Date | Treatment Group | Average plant height (inches) | Average plant width (inches) | Average number of leaves | Average leaf measurements (Length × width) |
|---|---|---|---|---|---|
| Apr. 10, 2013 | 20-20-20 | 2.5 | 1 | 2 | |
| Apr. 19, 2013 | | 11 | 7 | 4 | |
| May 14, 2013 | | 12 | 15 | 6 | 6 × 4 |
| Apr. 10, 2013 | IGS + 20-20-20 | 3 | 1.5 | 2 | |
| Apr. 19, 2013 | | 15 | 14 | 8 | |
| May 14, 2013 | | 20 | 25 | 10 | 12 × 9 |

Figure 26:
FIG. 26 shows a representative photograph pertaining to the effect of IN-M1 on Swiss Chard 40 days after seeding.

The Swiss Chard was harvested on day 40 (May 14, 2013). FIG. 26 illustrates improved plant growth indicated by biomass as measured by height, width and number of leaves.

Example 11—Use of the Compositions and Methods to Biostimulate Ornamental Plants The horticulture team at Brookgreen Botanical planted hyacinths in early March 2013. The bulbs were divided into two batches one batch was treated with a cell-free supernatant composition prepared from a microbial culture comprising IN-M1 prior to planting and during growth, whereas the control group was not. Both groups were planted side by side in three locations in the botanical gardens. The treated plants were almost all in bloom 28 days after planting and an average of 6.6 inches high; whereas the untreated group exhibited mainly leaves, very few blooms, with the majority of buds deep in the leaf cluster, and were an average of 3.7 inches high. Without wishing to be bound by theory, these data suggest that a cell-free supernatant composition prepared from a microbial culture comprising IN-M1 may have a bio-stimulant effect on ornamental plants.

Sixty Hyacinth bulbs were planted Mar. 7, 2013. On planting, 30 bulbs were soaked in a cell-free supernatant composition prepared from a microbial culture comprising IN-M1, one part a cell-free supernatant composition prepared from a microbial culture comprising IN-M1 to 100 parts water. The soil where the treated bulbs were planted was soaked to a depth of 4 inches prior to planting. The treated plants were watered with a 1:100 dilution, a cell-free supernatant composition prepared from a microbial culture comprising IN-M1 to water, as needed.

A control group was planted in the same locations as the treated bulbs. The control group soil was watered to a depth of 4 inches and the plants were watered at the same time as the treated group. The progress of both groups of the hyacinth bulbs was monitored regularly; emergence of shoots recorded, and the height of the leaves and frequency of flowering. Ten bulbs were monitored in each location.

The results of the study are illustrated in Table 6 below. The emergence of leaves in the treated group occurred at an average of 6.1 days after planting; whereas in the control group, emergence occurred an average of 7.7 days after planting; 21% acceleration in emergence. The treated plants' leaves continued to exhibit an accelerated growth over the control group during a 28 day period. Flowering in the case of the treated bulbs was accelerated compared to the control group at each location. A significant effect was demonstrated on spring plantings of hyacinth bulbs; both accelerated emergence and height difference was recorded as well as an earlier development of blooms.

TABLE 6

|  | Overall difference in emergence (days) | Average difference in height (inches) at day 28 | Flowering per 10 treated plants at day 28 | Flowering per 10 untreated control plants at day 28 |
| --- | --- | --- | --- | --- |
| Variation | 1.67 | 2.94 |  |  |
| Accelerated emergence | 21% |  |  |  |
| Average difference in height Mar. 4, 2014 |  | 44% |  |  |
| Position 1 |  |  | 10 | 4 |
| Position 2 |  |  | 9 | 3 |
| Position 3 |  |  | 10 | 1 |

Example 12—Effect of Cell-Free Supernatant Composition On Strawberry Plant Growth and Production A study was carried out to test the effect of IN-M1 cell-free supernatant (batch # EA 130129-2) on strawberry growth and production.

Methods: The field consisted of a total area of 522.6 m$^2$ (5,625 square feet) planted with 12 rows each containing 650 plants spaced approximately 15 cm (6 inches) apart. 200 Albion strawberry seedlings per treatment were planted in the middle of the field (rows 4 to 6) on a single row with 50 control plants (pre-treated with water) planted at the end of each row. Nine different treatments were applied in this field trial.

Strawberry seedlings were received from Nova Scotia and kept at 4° C. One day before planting, seedlings were soaked in 6 liters of a 1/40 dilution of IN-M1 cell-free supernatant (batch # EA 130129-2). Seedlings were first completely submerged in the treatment solution and then roots were left soaking for 4 hrs. Control plants were treated with water. Two and a half months after planting, plants were re-treated by drenching each plant with approximately 30 ml of the respective treatment.

Strawberry seedlings were planted by hand on a farm in Lambeth, Ontario, Canada. Soil was fertilized with 4.5 kilos (10 lbs) per week of equal amounts of calcium nitrate and potassium nitrate. Plant growth was monitored at the sixth and eleventh week after planting by measuring chlorophyll content, leaf height and width.

During week 11, the harvest season began and fruits were collected, by the farmer, every two days for approximately two months. After each harvest, fruits per treatment were weighted and the results reported to A & L Biologicals.

Data were analyzed using the SAS program and the General Linear Model (GLM) Procedure. This procedure gives the results of three different statistical tests including T-Tests, Duncan's Multiple Range Test and Tukey's Studentized Range.

Figure 27:
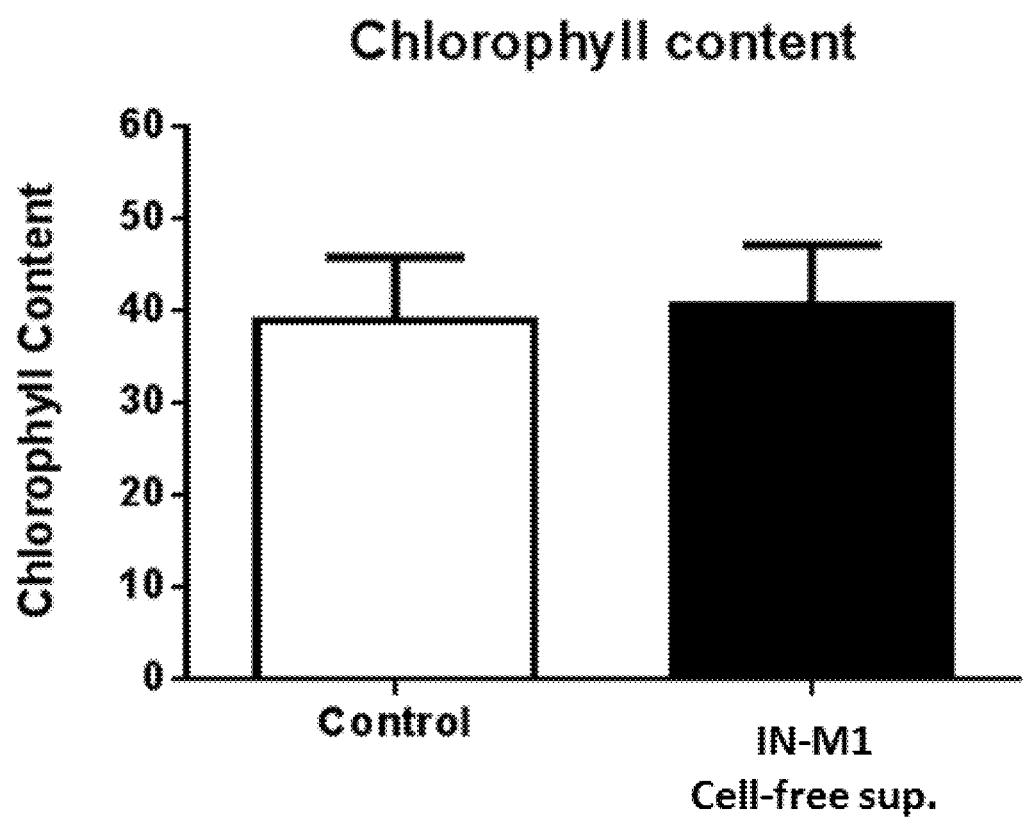
FIG. 27 shows representative chlorophyll content of strawberry plants. The data were obtained from strawberry plants that were treated with IN-M1 cell-free supernatant, as described in the Examples, compared to control plants. Bars and error bars show the mean and standard deviation, respectively, of chlorophyll.

Results: Six weeks after planting, plant growth was monitored and strawberry seedlings treated with IN-M1 supernatant and control seedlings showed similar growth physiology. Chlorophyll content was determined using SPAD 502 chlorophyll meter (area measured=2 mm×3 mm, Konica). The values defined by the SPAD 502 chlorophyll meter indicate the relative amount of chlorophyll present in strawberry plant leaves. Chlorophyll readings were taken from 3 leaves of 40 plants per treatment. Plants were randomly selected. There was no statistically significant difference between control or IN-M1 cell-free supernatant-treated plants (FIG. 27).

Figure 28A:
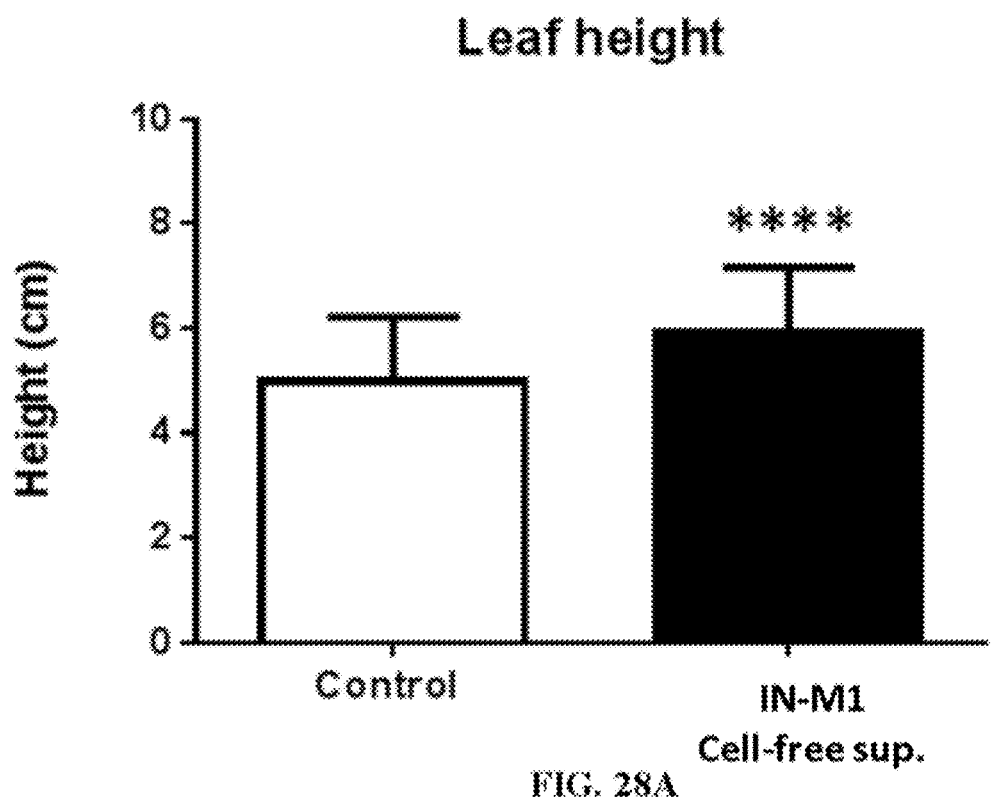
FIGS. 28A and 28B show representative for leaf height and width, respectively, for strawberry plants that were treated with IN-M1 cell-free supernatant, as described in the Examples, compared to control plants. Bars and error bars show the mean and standard deviation, respectively, of height and width of the leaves. ****=statistically significant with a 99.99% confidence level (P<0.0001).
Figure 28B:
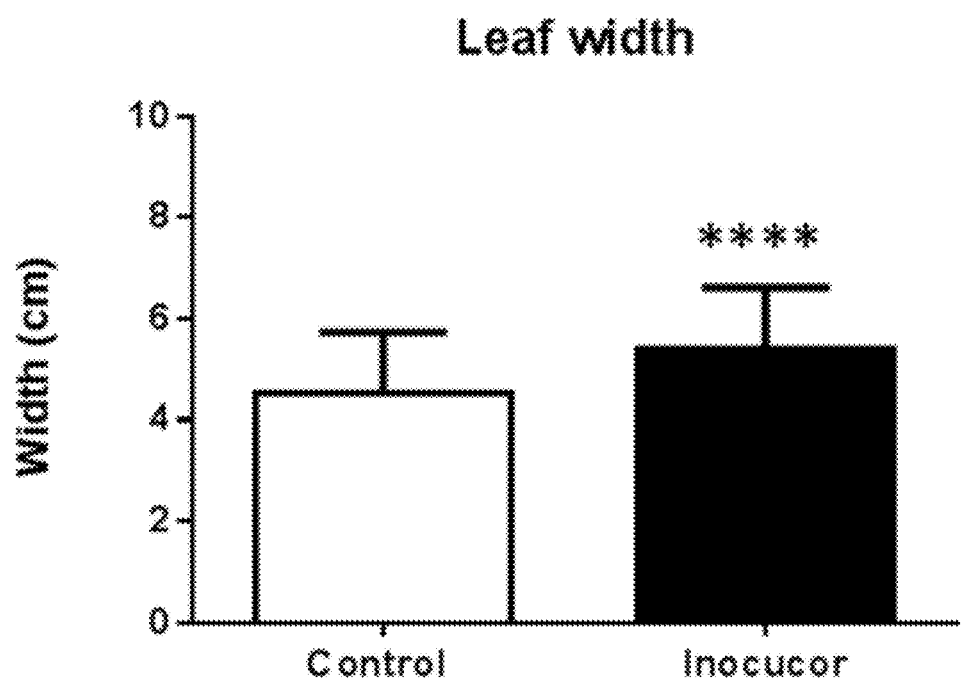

Forty plants from each treatment were randomly selected and leaf width and height was measured for 4 leaves per plant. The data in FIGS. 28A and 28B show that the width and height of leaves, respectively, from plants treated with IN-M1 cell-free supernatant were significantly bigger than control leaves ($p<0.0001$). These results show that IN-M1 cell-free supernatant stimulated plant growth.

Eleven weeks after planting, leaves height and width was measured as described above. However, at this time point, there was no finding of a statistically significant difference between treated and control plants.

Figure 29:
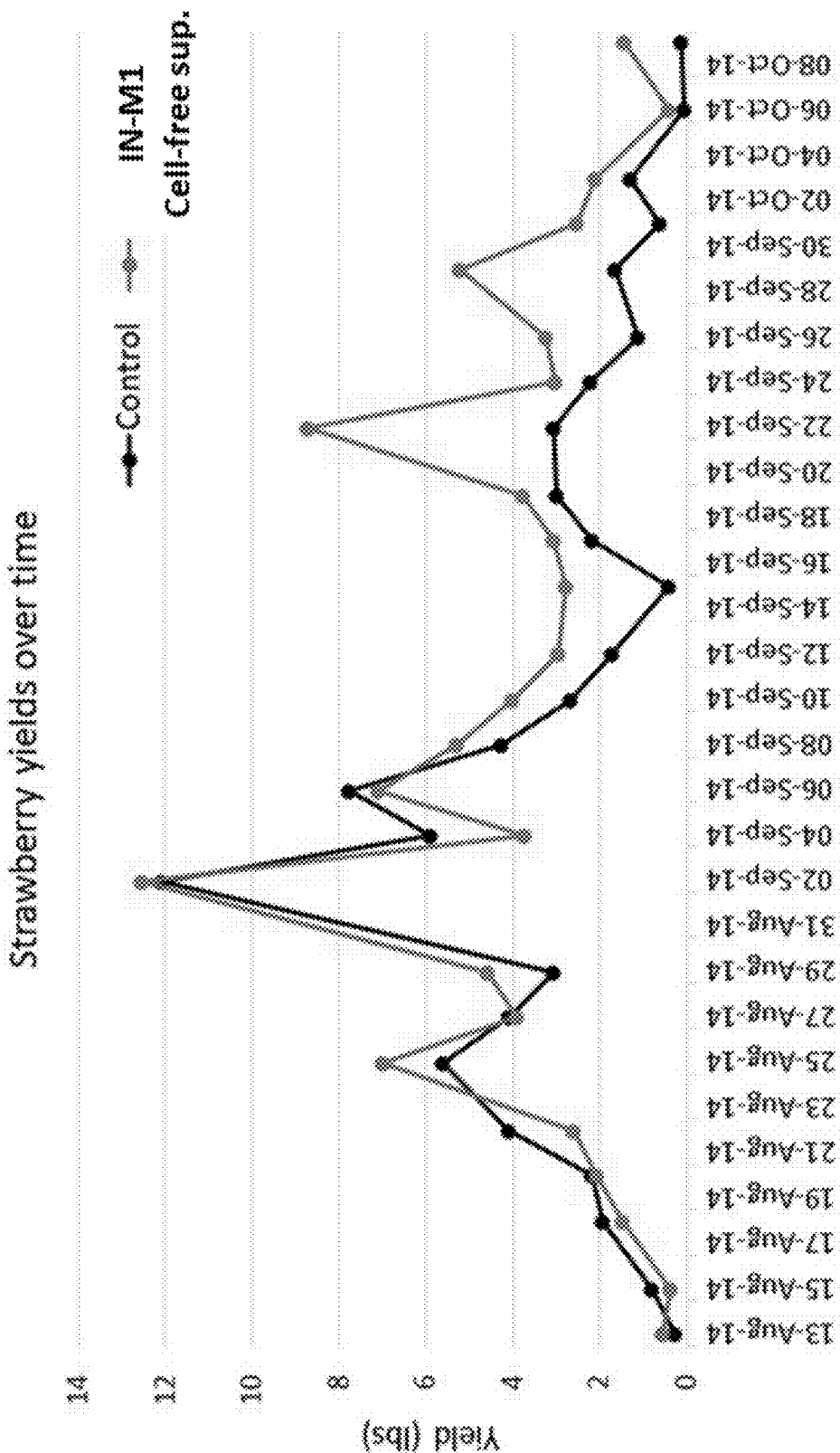
FIG. 29 shows representative data for fruit yield in strawberry plants at week 11 to week 19 post-planting. The data are shown for strawberry plants that were treated with IN-M1 cell-free supernatant, as described in the Examples, compared to control plants. The yield data are shown for the day that fruit was harvested; fruit was harvested every two days beginning during week 11.
Figure 30:
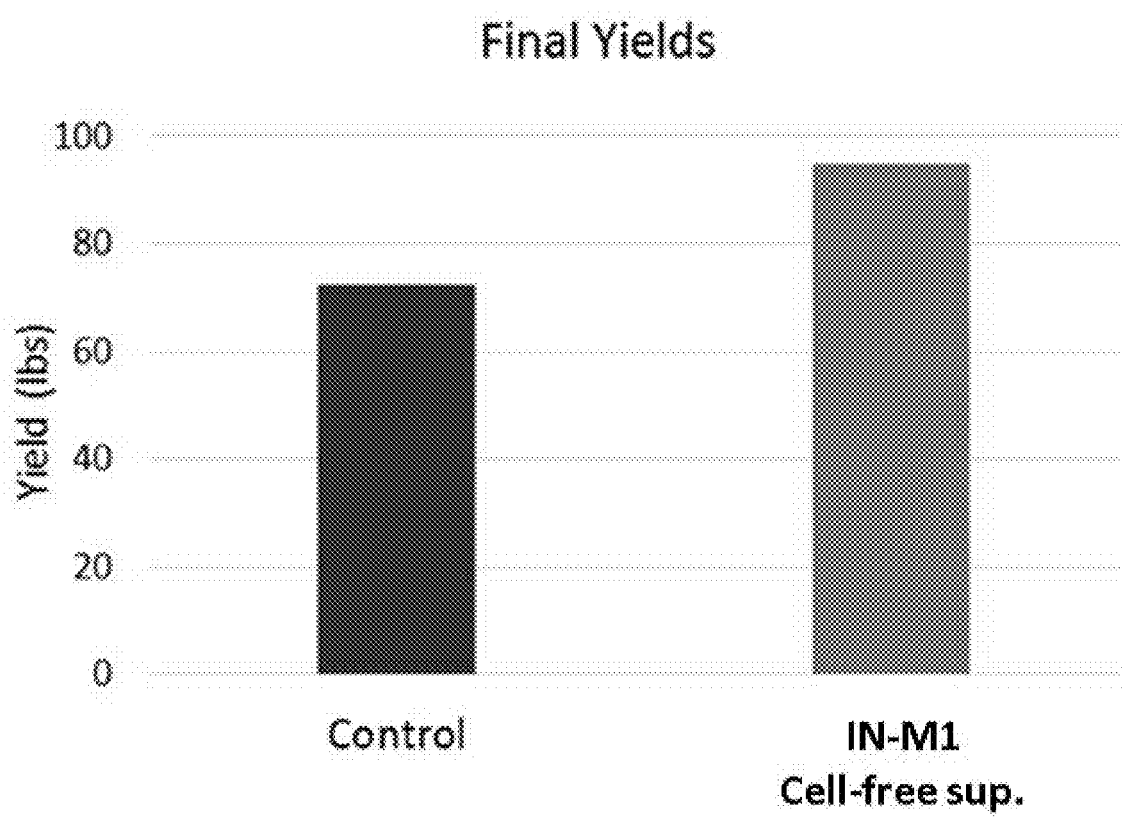
FIG. 30 shows representative data for total fruit yield in strawberry plants that were treated with IN-M1 cell-free supernatant, as described in the Examples, compared to control plants.

During week 11, harvest season began and fruits were collected every two days thereafter. FIG. 29 shows a comparison over time of the fruit production between control and Inocucor treated plants. In general, treated plants produced higher yields than control plants during the whole season and production stayed more uniform over time. Data collected after the final harvest (week 19), showed that IN-M1 cell-free supernatant-treated plants produced 42.9 kilos (94.63 lbs) while control plants produced 32.8 kilos (72.23 lbs) (FIG. 30). This represents a 31% increase in yields.

The data in this study demonstrate that treating strawberry seedlings with IN-M1 cell-free supernatant before planting improved plant growth at early stages and more importantly, increased strawberry production by 31% as compared to control plants. Similar results are expected for treatment with other disclosed compositions, including the IN-M2 cell-free supernatant.

Example 13—Effect of Cell-Free Supernatant Composition on Greenhouse Corn Plant Growth and Production A study was carried out to test the effect of IN-M1 cell-free supernatant on greenhouse corn growth and production.

Methods: The study utilized four corn plants per pot, with four replications of each treatment. The plants were planted in ProMix soil with Hogrens fertilizer (½ strength). The treatments were as follows: Dose 1, 1:100 dilution IN-M1 cell-free supernatant was applied 5 times (dose 1: at the seedling stage); Dose 2, 1 week after first application; Dose 3, 3 weeks after first application; Dose 4, 6 weeks after first application; and Dose 5, 9 weeks after the first application. All the leaves per plant, at final harvest, were used for leaf area measurement.

Results: The data showed that corn plants treated with a 1:100 dilution IN-M1 cell-free supernatant had an average increase of 20% in emergence from soil compared to control plants. In addition, treated plants had an average increase of 17% in plant height compared to control plants at the conclusion of the experiment. Although there was no increase in leaf number per treated plant compared to control plants, there was an increase in the leaf area (11% increase) and dry biomass (12% increase) of treated plants compared to control plants.

Example 14—Effect of Cell-Free Supernatant Composition on Corn Plant Growth and Production Under Field Conditions A study was carried out to test the effect of IN-M1 cell-free supernatant on greenhouse corn growth and production under field conditions.

Methods: Plants were dosed at time of seeding with a 1:100 dilution of the IN-M1 cell-free supernatant and kept moist until transplantation to the field. Upon transplantation to the field, a foliar application of a 1:100 dilution of the IN-M1 cell-free supernatant was carried out once per week.

Figure 31:
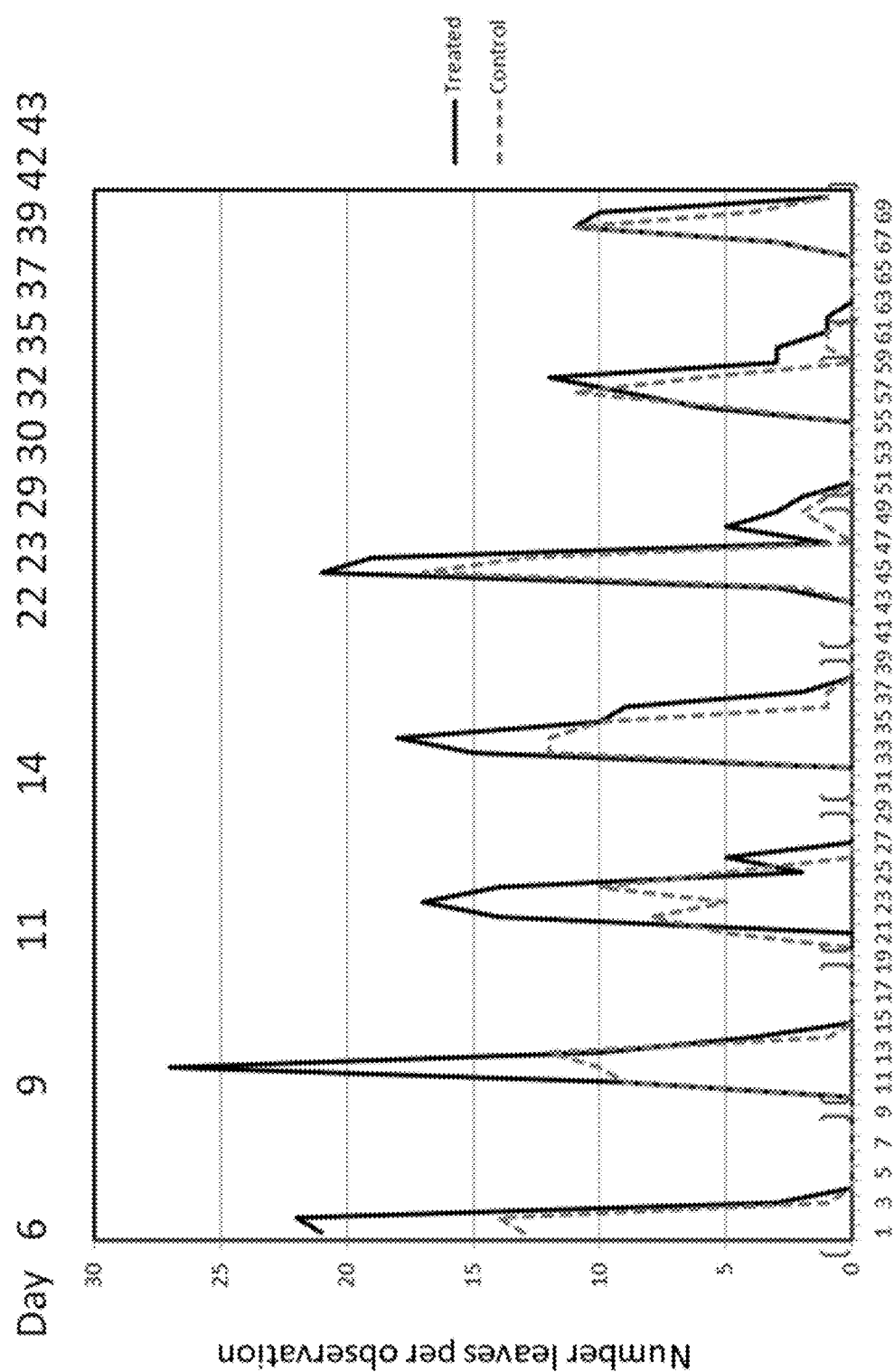
FIG. 31 shows representative data from a field trial for leaf progression development in corn plants treated IN-M1 cell-free supernatant compared to control plants.

Results: The treated plants exhibited a 20% increase in emergence at day 15. In particular, there was a 64% emergence at day 15 for the treated group versus a 44% emergence at day 15 for the control group. The data for progression of leaf development (over the period of day 6-43 post-planting) is shown in FIG. 31. The data show that the leading edge of the curve moving to the next leaf in the progression of leaf development is more rapid for treated plants compared to control.

Example 15—Effect of Cell-Free Supernatant Composition on Soybean Plant Growth and Production Under Field Conditions A study was carried out to test the effect of IN-M2 cell-free supernatant on greenhouse corn growth and production. The study was carried out a Lods Agronomy Research Centre, McGill University, Montreal, Quebec, Canada. The IN-M2 cell-free supernatant was sprayed as a foliar spray at the 3 trifoliate crop stage and the crop yield was assessed at the end of the season. The foliar spray included herbicide (Nufarm Polaris®, Nufarm Agriculture, Inc., Calgary, Alberta, Canada; applied at an effective amount of 2.5 L ha$^{-1}$) and micronutrient formulation (Crop Booster®, Axter Agroscience, Inc., Mont St-Hilaire, Quebec, Canada; applied at an effective amount of 2 L ha$^{-1}$) as indicated in the table below. Yields from two different growing seasons, 2013 and 2104, respectively, are below in Tables 7 and 8.

TABLE 7

| No. | Treatments | Yield* 2013 | Increased yield** |
|---|---|---|---|
| 1 | Herbicide | 5058 | |
| 2 | Herbicide + crop booster | 5481 | |
| 3 | Herbicide + crop booster + IN-M2 (1:25) | 5594 | |
| 4 | Herbicide + crop booster + IN-M2 (1:100) | 5619 | 11.0% |
| 5 | Herbicide + crop booster + IN-M2 (1:1000) | 5244 | |

*kg ha$^{-1}$
**compared to control (% increase)

TABLE 8

| No. | Treatments | Yield* | Increased yield** |
|---|---|---|---|
| 1 | Herbicide | 5033 | |
| 2 | Herbicide + crop booster | 5303 | |
| 3 | Herbicide + crop booster + IN-M2 (1:100) | 5514 | 10.0% |

*kg ha$^{-1}$
**compared to control (% increase)

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A cell-free supernatant composition comprising:
   (i) an isolated cell-free supernatant of a microbial culture, obtained by (1) inoculating an isolated mixed microbial composition comprising isolated microorganisms of IN-M1, ATCC Patent Deposit Designation No. PTA-12383 into a culture medium comprising water, a molasses, a mineral powder, a sea salt, and a wheat bran, (2) incubating the inoculated media for 3-10 weeks at 30-32 or 35-37 or 32-37 degrees Celsius, thereby obtaining the microbial culture, and (3) centrifuging the microbial culture to separate microbial culture cells from a supernatant and filter sterilizing the supernatant to obtain the cell-free supernatant of the microbial culture, wherein the cell free supernatant comprises at least 2500 micrograms potassium per gram of cell-free supernatant, at least 435 micrograms nitrogen per gram of cell-free supernatant, at least 475 micrograms calcium per gram of cell-free supernatant, and at least 200 micrograms magnesium per gram of cell-free supernatant, and
   (ii) diluent water,
   wherein the ratio between the cell-free supernatant of the microbial culture and the diluent water in the cell-free supernatant composition is between 1:25 and 1:1000.

2. The cell-free supernatant composition of claim 1, further comprising a herbicide.

3. The cell-free supernatant composition of claim 1, further comprising a pesticide.

4. The cell-free supernatant composition of claim 1, further comprising a fungicide.

5. The cell-free supernatant composition of claim 1, further comprising a liquid nutrient solution for enabling plant growth and added to the cell free supernatant after centrifugation and sterile filtration.

6. The cell-free supernatant composition of claim 1, wherein said isolated mixed microbial composition further comprises at least one isolated mycorrhizal fungus.

7. A composition comprising an agronomically acceptable carrier and an effective amount of the cell-free supernatant composition of claim 1.

8. The cell-free supernatant composition of claim 1, wherein the molasses is a non-sulphur agricultural molasses, the wheat bran is 0.02-0.05% by volume, and the culture medium further comprises a kelp (0.02-0.05% by volume), a bentonite clay (0.02-0.05% by volume), a fish emulsion, and a soy flour (0.005-0.03% by volume).

9. The cell-free supernatant composition of claim 1, wherein the cell free supernatant comprises 2500 micrograms potassium per gram of cell-free supernatant, 435-600 micrograms nitrogen per gram of cell-free supernatant, 475-660 micrograms calcium per gram of cell-free supernatant, and 200-260 micrograms magnesium per gram of cell-free supernatant.

10. The cell-free supernatant composition of claim 1, wherein the microbial culture is centrifuged at a centrifugal force of at least 14,000×g for at least 10 minutes.

11. The cell-free supernatant composition of claim 1, wherein the supernatant is filter sterilized with a 0.22 micron filter.

12. The cell-free supernatant composition of claim 1, wherein
   the molasses is non-sulphur agricultural molasses, the wheat bran is 0.02-0.05% by volume, and the culture medium further comprises a kelp (0.02-0.05% by volume), a bentonite clay (0.02-0.05% by volume), a fish emulsion, and a soy flour (0.005-0.03% by volume);
   the microbial culture is centrifuged at a centrifugal force of at least 14,000×g for at least 10 minutes;
   the supernatant is filter sterilized with a 0.22 micron filter; and
   the cell free supernatant comprises about 2500 micrograms potassium per gram of cell-free supernatant, 435-600 micrograms nitrogen per gram of cell-free supernatant, 475-660 micrograms calcium per gram of cell-free supernatant, and 200-260 micrograms magnesium per gram of cell-free supernatant.

* * * * *